USOO5700683A

United States Patent [19]
Stover et al.

[11] Patent Number: 5,700,683
[45] Date of Patent: Dec. 23, 1997

[54] VIRULENCE-ATTENUATING GENETIC DELETIONS DELETED FROM MYCOBACTERIUM BCG

[75] Inventors: Charles Kendall Stover, Mercer Island; Gregory G. Mahairas, Seattle, both of Wash.

[73] Assignee: PathoGenesis Corporation, Seattle, Wash.

[21] Appl. No.: 390,878

[22] Filed: Feb. 17, 1995

[51] Int. Cl.[6] .................... C07H 21/02; C07H 21/04; C12N 1/21; C12Q 1/68
[52] U.S. Cl. .................... 435/252.31; 435/240.2; 435/252.1; 435/253.1; 435/91.2; 435/6; 435/320.1; 536/24.31; 536/24.32; 536/24.33; 536/22.1
[58] Field of Search .................... 536/22.1, 24.3, 536/24.33, 24.31, 24.32; 435/320.1, 240.2, 6, 91.2

[56] References Cited

U.S. PATENT DOCUMENTS

| | | | |
|---|---|---|---|
| 4,410,660 | 10/1983 | Straus | 525/54.1 |
| 4,683,202 | 7/1987 | Mullis | 435/91 |
| 5,171,839 | 12/1992 | Patarroyo | 435/6 |
| 5,254,459 | 10/1993 | Patarroyo et al. | 435/6 |

FOREIGN PATENT DOCUMENTS

| | | |
|---|---|---|
| 1-247094 | 10/1989 | Japan. |
| WOA295/17511 | 6/1995 | WIPO. |

OTHER PUBLICATIONS

Infection and Immunity, vol. 59, No. 10, issued Oct. 1991, C. Parra et al., "Isolation, characterization and molecular cloning of a specific mycobacterium tuberculosis antigen gene: identification of a species–specific sequence", pp. 3411–3417.

Abstracts of the 1994 IDSA Annual Meeting, Clin. Infect. Dis., vol. 19, issued Oct. 1994, R. Frothingham et al., "Sequence based strain differentiation in the Mycobacterium tuberculosis complex, including rapid identification of M. bovis BCG", p. 565, see abstract 10.

R. Gherna et al., "American Type Culture Collection: Catalogue of Bacteria and Phages", Eighteenth edition, published 1992, pp. 202 and 211.

Infection and Immunity, vol. 62, No. 4, issued Apr. 1994, L. Pascopella et al., "Use of in vivo complementation in Mycobacterium tuberculosis to identify a genomic fragment associated with virulence", pp. 1313–1319.

Science, vol. 261, issued 10 Sep. 1993, S. Arruda et al., "Cloning of an M. Tuberculosis DNA fragment associated with entry and survival inside cells", pp. 1454–1457.

Nature, vol. 256, issued 07 Aug. 1975, C. Kohler et al., "Continuous cultures of fused cells secreting antibody of predefined specificity", pp. 495–497.

Genomics, vol. 4, issued 1989, D. Wu et al., "The ligation amplification reaction (LAR) amplification of specific DNA sequences using sequential rounds of template directed ligation", pp. 560–569.

Gene, vol. 131, issued 1993, A. Kinger et al., "Identification and cloning of genes differentially expressed in the virulent strain of mycobacterium tuberculosis", pp. 113–117.

Microbiology, vol. 141, issued 1995, J. Rodriguez et al., "Species–specific identification of mycobacterium bovis by PCR", pp. 2131–2138.

(List continued on next page.)

*Primary Examiner*—George C. Elliott
*Assistant Examiner*—Jeffrey Fredman
*Attorney, Agent, or Firm*—Townsend and Townsend and Crew LLP

[57] ABSTRACT

The present invention provides specific genetic deletions that result in an avirulent phenotype of a mycobacterium. These deletions may be used as phenotypic markers of providing a means for distinguishing between disease-producing and non-disease producing mycobacteria.

57 Claims, 63 Drawing Sheets

| ORF | *M. tuberculosis* CODON USAGE | ORF SIZE (BASE PAIRS) | START-STOP (BASE PAIRS) | POSSIBLE RIBOSOME BINDING SITES | ENCODED PROTEIN (MAX.–kDa) | HOMOLOGIES TO PREDICTED ENCODED PROTEIN | P VALUE | HOMOLOGUE ACCESSION # |
|---|---|---|---|---|---|---|---|---|
| 1A | YES | 1542 | 889–2433 | AGGA (10) | 57 | | | |
| 1B | YES | 1071 | 3130–4203<br>3139–4203 | GGA (4)<br>GGA (9) | 36 | *M. leprae* aceA<br>BCG urgA | 1.4e-14<br>3.0e-13 | Z46257<br>U01072 |
| 1C | YES | 969 | 5075–6046 | GAGG (5) | 34 | *M. tuberculosis* esat6 | 2.3e-43 | X79562 |
| 1D | YES | 1657 | 6954–8612 | NONE | 59 | | | |
| 1E | YES | 954 | 10619–9663 | GGA(5) | 34 | | | |
| 1F | YES | 1380 | 13328–11946 | AGGA(9) | 48 | | | |
| 1G | YES | 1386 | 14823–13438<br>14643–13438<br>14541–13438 | NONE<br>GGA(11)<br>AGGAGA (10) | 50 | | | |
| 1H | YES | 1368 | 16190–14820 | GAA (5) | 46 | *B. subtilis* subtilisin SERINE PROTEASES | 3.6e-16 | L29506 |

OTHER PUBLICATIONS

Hybridoma, vol. 13, No. 1, issued 1994, A. Arya et al., "Production and characterization of new murine monoclonal antibodies reactive to mycobacterium tuberculosis", pp. 21–30.

Li et al, "Evidence for absence of MPB64 gene in some substrains of mycobacterium bovis BCG", Inf. Immun. 61(5):1730–1734, May 1993.

Mahairas et al, "Molecular analysis of genetic differences between mycobacterium bovis BCG and virulent M. bovis", J. Bacteriol. 178(5):1274–1282, Mar. 1996.

Andersen, A. et al., *Scand. J. Immunol.* 34:365 (1991).

Haslov, K. et al., *J. Bacteriol.* 63:804 (1995).

Oettinger, T. et al., *Infect. Immun.* 62:2058 (1994).

Strain, S.M. et al., *Biochem. Res. Comm.* 77:449 (1977).

Takayama, K. et al., *Antimicrob. Agents. Chemother.* 2:29 (1972).

FIGURE 1-1

```
GAATTCCTGC GCACCCTGAT CCTGTCGCTG GTGGCAATGA CTCATCCAGA TCAGGTGAAT    60
CTCCTGCTCA CCGACTTCAA AGGTGGTTCA ACCTTCCTGG GAATGAAAAA GCTTCCGCAC   120
ACTGCCGCTG TCGTCACCAA CATGGCCGAG GAAGCCGAGC TCGTCAGCCG GATGGGCGAG   180
GTGTTGACCG GAGAACTCGA TCGGGCGCAG GACAGGCCGG GATGAAAGTC              240
GGCGCGGCCG GAGCCCTGTC CGGGGTGGCC GAATACGAGA AGTACCGCGA ACGCGGTGCC   300
GACCTACCCC CGCTGCCAAC GCTTTTCGTC GTCGTCGACG AGTTCGCCGA GCTGTTGCAG   360
AGTCACCCGG ACTTCATCGG GCTGTTCGAC CGGATCTGCC GCGTCGGGCG GTCGCTGAGG   420
GTCCATCTGC TGCTGGCTAC CCAGTCGCTG CAGACCGGCG GTGTTGCAT CGACAAACTG    480
GAGCCAAAAC TGACATATCG AATCGCATTG CGCACCACCA GCTCTCATGA ATCCAAGGCG   540
GTAATCGGCA CACCGGAGGC GCAGTACATC ACCAACAAGG AGAGCGGTGT CGGGTTTCTC   600
CGGGTCGGCA TGAAGACCC GGTCAAGTTC AGCACCTTCT ACATCAGTGG GCCATACATG    660
CCGCCGGCGG CAGGGCGTCA AACCAATGGT GAAGCCGGAG GGCCCGGTCA ACAGACCACT   720
AGACAAGCCG CGGCCATTCA CAGGTTCACC CGGGCACCGG TTCTCGAGGA GGCGCCGACA   780
```

FIGURE 1-2

```
CCGTGACCCG CGCCGGCGAC GATGCAAAGC GCAGCGATGA GGAGGAGCGG CGCCAACGGC    840
CCGCGCCGGC GACGATGCAA AGCGCAGCGA TGAGGAGGAG CGGCGGCGCAT GACTGCTGAA    900
CCGGAAGTAC GGACGCTGCG CGAGGTTGTG CTGGACCAGC TCGGCACTGC TGAATCGCGT    960
GCGTACAAGA TGTGGCTGCC GCCGTTGACC AATCCGGTCC CGCTCAACGA GCTCATCGCC   1020
CGTGATCGGC GACAACCCCT GCGATTTGCC CTGGGGATCA CAGACGATGG TGGATGAACC   1080
CTACAGGATG TGTGGGGCGT AGACGTTTCC GGGGCCGGCG GCAACATCGG TATTGGGGGC   1140
GCACCTCAAA CCGGGAAGTC GACGCTACTG CAGACGTACTG TGATGTCGGC CGCCGCCACA   1200
CACTCACCGC GCAACGTTCA GTTCTATTGC ATCGACCTAG GTGGGGGCGG GCTGATCTAT   1260
CTCGAAAACC TTCCACACGT CGGTGGGGTA GCCAATCGGT CCGAGCCCGA CAAGGTCAAC   1320
CGGGTGGTCG CAGAGATGCA AGCCGTCATG CGGCAACGGG AAACCACCTT CAAGGAACAC   1380
CGAGTGGGCT CGATCGGGAT GTACCGGCAG CTGCGTGACG ATCCAAGTCA ACCCGTTGCG   1440
TCCGATCCAT ACGGCGACGT CTTTCTGATC ATCGACGGAT GGCCCGGTTT TGTCGGCGAG   1500
TTCCCCGACC TTGAGGGGCA GGTTCAAGAT CTGGCCCGCC AGGGGCTGGG GTTCGGCGTC   1560
```

FIGURE 1-3

```
CACGTCATCA TCTCCACGCC ACGCTGGACA GAGCTGAAGT CGGCGTGTTCG CGACTACCTC    1620
GGCACCAAGA TCGAGTTCCG GCTTGGTGAC GTCAATGAAA CCCAGATCGA CCGGATTACC    1680
CGCGAGATCC CGGCGAATCG TCCGGGTCGG GCAGTGTCGA TGGAAAAGCA CCATCTGATG    1740
ATCGGCGTGC CCAGGTTCGA CGGCGTGCAC AGCGCCGATA ACCTGGTGGA GGCGATCACC    1800
GCGGGGGTGA CGCAGATCGC TTCCCAGCAC CACCTCCGGT GCGGGTCCTG                1860
CCGGAGCGTA TCCACCTGCA CGAACTCGAC CCGAACCCGC CGGGACCAGA GTCCGACTAC    1920
CGCACTCGCT GGGAGATTCC GATCGGCTTG CGGCGAGACGG ACCTGACGCC GGCTCACTGC    1980
CACATGCACA CGAACCCGCA CCTACTGATC TTCGGTGCCGG CCAAATCGGC CAAGACGACC    2040
ATTGCCCACG CGATCGCGCG CGCCATTTGT GCCCGAAACA GTCCCCAGCA GGTGCGGTTC    2100
ATGCTCGCGG ACTACCGCTC GGGCCTGCTC GACGCGGGTGC CGGACACCCA TCTGCTGGGC    2160
GCCGGCGCGA TCAACCGCAA CAGCGCGGTCG CTAGACGAGG CCGCTCAAGC ACTGGCGGTC    2220
AACCTGAAGA AGCGGTTGCC GCCGACCGAC CTGACGACGG CGCAGCTACG CTCGGTTCG    2280
TGGTGGAGCG GATTTGACGT CGTGCTTCTG GTCGACGATT GGCACATGCA GCCGTGGGTG    2340
```

FIGURE 1-4

```
CCGCCGGGGG GATGCCGCCG ATGGCACCGC TGGCCCCGTT ATTGCCGGCG GCGGCAGATA    2400
TCGGGTTGCA CATCATTGTC ACCTGTCAGA TGAGCCAGGC TTACAAGGCA ACCATGGACA    2460
AGTTCGTCGG CGCCGCATTC GGGTCGGGCG CTCCGACAAT GTTCCTTTCG GGCGAGAAGC    2520
AGGAATTCCC ATCCAGTGAG TTCAAGGTCA AGCGGCGCCC CCCTGGCCAG GCATTTCTCG    2580
TCTCGCCAGA CGGCAAAGAG GTCATCCAGG CCCCCTACAT CGAGCCTCCA GAAGAAGTGT    2640
TCGCAGCACC CCCAAGCGCC GGTTAAGATT ATTTCATTGC CGGTGTAGCA GGACCCGAGC    2700
TCAGCCCCGT AATCGAGTTC GGGCAATGCT GACCATGGG TTTGTTTCCG GCTATAACCG    2760
AACGGTTTGT GTACGGGATA CAAATACAGG GAGGGAAGAA GTAGGCAAAT GGAAAAAATG    2820
TCACATGATC CGATCGCTGC CGACATTGGC ACGCAAGTGA GCGACAACGC TCTGCACGGC    2880
GTGACGGCCG GCTCGACGGC GCTGACGTCG GTGACCGGGC TGGTTCCCGC GGGGGCCGAT    2940
GAGGTCTCCG CCCAAGCGGC GACGGCGTTC ACATCGGAGG GCGGGCGAAG GCATCCAATT    3000
AATGCATCGG CCCAAGACCA GCTCCACCGT GCGGGCGAAG CGGTCCAGGA CGTCGCCCGC    3060
ACCTATTCGC AAATCGACGA CGGCGCCGCC GGGTCTTCG CCTAATAGGC CCCAACACA     3120
```

FIGURE 1-5

```
TCGGAGGGAG TGATCACCAT GCTGTGGCAC GCAATGCCAC CGGAGCTAAA TACCGCACGG    3180
CTGATGGCCG GCGCGGGTCC GGCTCCAATG CTTGCGGGCG CCGCGGGATG GCAGACGCTT    3240
TCGGGGCTC  TGGACGCTCA GGCCGTCGAG TTGACCGCGC GCCTGAACTC TCTGGGAGAA    3300
GCCTGACTG  GAGGTGGCAG CGACAAGGCG CTTGCGGCTG CAACGCCGAT GGTGGTCTGG    3360
CTACAAACCG CGTCAACACA GGCCAAGACC CGTGCGATGC AGGCGACGGC GCAAGCCGCG    3420
GCATACACCC AGGCCATGGC CACGACGCCG TCGCTGCCGG AGATCGCCGC CAACCACATC    3480
ACCCAGGCCG TCCTTACGGC CACCAACTTC TTCGGTATCA ACACGATCCC GATCGCGTTG    3540
ACCGAGATGG ATTATTTCAT CCGTATGTGG AACCAGGCAG CCCTGGCAAT GGAGGTCTAC    3600
CAGGCCGAGA CCGGGTTAA  CACGCTTTC  GAGAAGCTCG AGCCGATGGC GTCGATCCTT    3660
GATCCCGGCG CGAGCCAGAG CACGACGAAC CCGATCTTCG GAATGCCCTC CCCTGGCAGC    3720
TCAACACCGG TTGGCCAGTT GCCGCCGGGCG GCTACCCAGA CCCGCTGCAGC ACTGGGTGAG    3780
ATGAGCGGCC CGATGCAGCA CCGTGACCCAG CCGCTGCAGC AGGTGACGTC GTTGTTCAGC    3840
CAGGTGGGCG GCACCGGCGG CGGCAACCCA GCCGACGAGG AAGCCGGGCA GATGGGCCTG    3900
```

FIGURE 1-6

```
CTCGGCACCA GTCCGCTGTC GAACCATCCG CTGGCTGGTG GATCAGGCCC CAGGCGGGC    3960
GCGGGCCTGC TGGCGCGGA GTCGCTACCT GGCGCAGGTG GGTCGTTGAC CCGCACGCCG    4020
CTGATGTCTC AGCTGATCGA AAAGCCGGTT TGCCCCCTCG GTGATGCCGG CGGCTGCTGC    4080
CGGATCGTCG GCGACGGGTG GCGCCGCTCC GGTGGGTGCG GGAGCGATGG GCCAGGGTGC    4140
GCAATCCGGC GGCTCCACCA GGCCGGGTCT GGTCGCGCCG GCACCGCTCG CGCAGGAGCG    4200
TGAAGAAGAC GACGAGGACG ACTGGGACGA AGAGGACGAC TGGTGAGCTC CCGTAATGAC    4260
AACAGACTTC CCGGCCACCC GGGCCCGGAAG ACTTGCCAAC ATTTTGGCGA GGAAGGTAAA    4320
GAGAGAAAGT AGTCCAGCAT GGCAGAGATG AAGACCGATG CCGCTACCCT CGGCAGGAG    4380
GCAGGTAATT TCGAGCGGAT CTCCGGCGAC CTGAAAACCC AGATCGACCA GGTGGAGTCG    4440
ACGGCAGGTT CGTTGCAGGG CCAGTGGCGC GGCGGGGCGG GGACGGCCGC CCAGGCCGCG    4500
GTGGTGCGCT TCCAAGAAGC AGCCAATAAG CAGAAGCAGG AACTCGACGA GATCTCGACG    4560
AATATTCGTC AGGCCGGGCGT CCAATACTCG AGGGCCGACG AGGAGCAGCA GCAGGCGCTG    4620
TCCTCGCAAA TGGGCTTCTG ACCCGCTAAT ACGAAAGAA ACGGAGCAAA AACATGACAG    4680
```

FIGURE 1-7

```
AGCAGCAGTG GAATTTCGCG GGTATCGAGG CCGGGGCAAG CGCAATCCAG GGAAATGTCA    4740
CGTCCATTCA TTCCCTCCTT GACGAGGGGA AGCAGTCCCT GACCAAGCTC GCAGCGGCCT    4800
GGGGCGGTAG CGGTTCGGAG GCGTACCAGG GTGTCCAGCA AAAATGGGAC GCCACGGCTA    4860
CCGAGCTGAA CAACGCGCTG CAGAACCTGG CGCGACGAT CAGGCGAAGCC GGTCAGGCAA    4920
TGGCTTCGAC CGAAGGCAAC GTCACTGGGA TGTTCGCATA GGGCAACGCC GAGTTCGCGT    4980
AGAATAGCGA AACACGGGAT CGGGCGAGTT CGACCTTCCG TCGGTCTCGC CCTTTCTCGT    5040
GTTTATACGT TTGAGCGCAC TCTGAGAGGT TGTCATGGCG GCCGACTACG ACAAGCTCTT    5100
CCGGCCGCAC GAAGGTATGG AAGCTCCGGA CGATATGGCA GCGCAGCCGT TCTTCGACCC    5160
CAGTGCTTCG TTTCCGCCGG CGCCCGCATC GGCAAACCTA CCGAAGCCCA ACGGCCAGAC    5220
TCCGCCCCCG ACGTCCGACG ACCTGTCGGA GCGGTTCGTG TCGGCCCCGC CGCCGCCACC    5280
CCCACCCCCA CCTCCGCCTC CGCCAACTCC GATGCCGATC GCCGCAGGAG AGCCGCCCTC    5340
GCCGGAACCG GCCGCATCTA AACCACCCAC ACCCCCCATG CCCATCGCCG GACCCGAACC    5400
GGCCCCACCC AAACCACCCA CACCCCCCA GCCCCATCGCC GGACCCGAAC CGGCCCCACC    5460
```

FIGURE 1-8

```
CAAACCACCC ACACCTCCGA TGCCCATGCC CGGACCTGCA CCCACCCCAA CCGAATCCCA    5520
GTTGGGCCC  CCCAGACCAC CGACACCACA AACGCCAACC GGAGGCCCGC AGCAACCGGA    5580
ATCACCGGCG CCCCACGTAC CCTCGCACGG GCCACATCAA CCCCGGCGCA CCGCACCAGC    5640
ACCGCCCTGG GCAAAGATGC CAATCGGCGA ACCCCCGCCC GCTCCGTCCA GACCGTCTGC    5700
GTCCCCGGCC GAACCACCGA CCCGGCCTGC CCCCCAACAC TCCCGACGTG CGGCCGGGG    5760
TCACCGCTAT CGCACAGACA CGGAAGCATC CGGCGCGCAG GTAGCAACTG GTCCATCCAT    5820
CCAGGGCGGG CTGCGGGCAG AGGAAGCATC CGGCGCGCAG CTCGCCCCCG GAACGGAGCC    5880
CTCGCCAGCG CCGTTGGGCC AACCGAGATC GTATCTGGCT CCGCCCACCC GCCCCGCC     5940
GACAGAACCT CCCCCCAGCC CCTCGCCCGCA GCGCAACTCC GGTCGGGCGTG CCGAGCGACG   6000
CGTCCGACCC CGATTTAGCC GCCCAACATG CCGCGGGCGCA ACCTGATTCA ATTACGGCCG   6060
CAACCCACTG GCGGTCGTCG CCGCAAGCGT GCAGCGCCGG GATGCTCGAC GCGACACAAG   6120
AAATCCTTAA GGCCGGCGGC CAAGGGGCCG AAGGTGAAGA AGGTGAAGCC CCAGAAACCG   6180
AAGGCCACGA AGCCGCCCAA AGTGGTGTCG CAGCGCGGCT GGCGACATTG GGTGCATGCG   6240
```

FIGURE 1-9

```
TTGACGCGAA TCAACCTGGG CCTGTCACCC GACGAGAAGT ACGAGCTGGA CCTGCACGCT    6300
CGAGTCCGCC GCAATCCCCG CGGGTCGTAT CAGATCGCCG TCGTCGGTCT CAAAGGTGGG    6360
GCTGGCAAAA CCACGCTGAC AGCAGCGTTG GGTCGACGT  TGGCTCAGT  GCGGGCCGAC    6420
CGGATCCTGG CTCTAGACGC GGATCCAGGC GCCGGAAACC TCGCCGATCG GGTAGGGCGA    6480
CAATCGGGCG CGACCATCGC TGATGTGCTT GCAGAAAAAG AGCTGTCGCA CTACAACGAC    6540
ATCCGCGCAC ACACTAGCGT CAATGCGGTC AATCTGGAAG TGCTGCCGGC ACCGGAATAC    6600
AGCTCGGCGC AGCGCGCGCT CAGCGACGCC GACTGGCATT TCATCGCCGA TCCTCGCTCG    6660
AGGTTTTACA ACCTCGTCTT GGCTGATTGT GGGGCCGGCT TCTTCGACCC GCTGACCCGC    6720
GGCGTGCTGT CCACGGTGTC CGGTGTCGTG GTCGTGCAA  GTGTCTCAAT CGACGGCGCA    6780
CAACAGGCGT CGGTCGCGTT GGACTGGTTG CGCAACAACG GTTACCAAGA TTTGGCGAGC    6840
CGCGCATGCG TGGTCATCAA TCACATCATG CCGGGAGAAC CCAATGTCGC AGTTAAAGAC    6900
CTGGTGCGGC ATTTCGAACA GCAAGTTCAA CCCGGCCGGG TCGTGGTCAT GCCGTGGGAC    6960
AGGCACATTG CGGCCGGAAC CGAGATTTCA CTCGACTTGC TCGACCCTAT CTACAAGCGC    7020
```

FIGURE 1-10

```
AAGGTCCTCG AATTGGCCGC AGCGCTATCC GACGATTTCG AGAGGGCTGG ACGTCGTTGA  7080
GCGCACCTGC TGTTGCTGCT GGTCCTACCG CCGGGGGGGC AACCGCTGCG CGGCCTGCCA  7140
CCACCCGGGT GACGATCCTG ACCGGCAGAC GGATGACCGA TTTGGTACTG CCAGCGGCGG  7200
TGCCGATGGA AACTTATATT GACGACACCG TCGCGGTGCT TTCCGAGGTG TTGGAAGACA  7260
CGCCGGCTGA TGTACTCGGC GGCTTCGACT TTACCGCGCA AGTCACTCGA GCGTTCGCTC  7320
GTCCCGGATC GCCGCCGCTG AAGCTCGACC AGTCACTCGA TGACGCCGGG GTGGTCGACG  7380
GGTCACTGCT GACTCTGGTG TCAGTCAGTC GCACCGAGCG CTACCGACCG TTGGTCGAGG  7440
ATGTCATCGA CGCGATCGCC GTGCTTGACG AGTCACCTGA GTTCGACCGC ACGGCATTGA  7500
ATCGCTTTGT GGGGGCGGCG ATCCCGCTTT TGACCGCGCC CGTCATCGGG ATGGCGATGC  7560
GGGCGTGGTG GGAAACTGGG CGTAGCTTGT GGTGGCCGTT GGCGATTGGC ATCCTGGGA  7620
TCGCTGTGCT GGTAGGCAGC TTCGTCGGA ACAGGTTCTA CCAGAGCGGC CACCTGGCCG  7680
AGTGCCTACT GGTCACGACG TATCTGCTGA TCGCAACCGC CGCAGCGCTG GCCGTGCCGT  7740
TGCCGGCGG GGTCAACTCG TTGGGGCGC CACAAGTTGC CGGGCCGCT ACGGCCGTGC  7800
```

FIGURE 1-11

| | | | | | |
|---|---|---|---|---|---|
| TGTTTTTGAC | CTTGATGACG | CGGGGCGGCC | CTCGGAAGCG | TCATGAGTTG | GCGTCGTTTG | 7860
| CCGTGATCAC | CGCTATCGCG | GTCATCGCGG | CCGCCGCTGC | CTTCGGCTAT | GGATACCAGG | 7920
| ACTGGGTCCC | CGCGGGGGGG | ATCGCATTCG | GGCTGTTCAT | TGTGACGAAT | GCGGCCAAGC | 7980
| TGACCGTCGC | ATCGCGCGG | ATCGCGCTGC | CGCCGATTCC | GGTACCCGGC | GAAACCGTGG | 8040
| ACAACGAGGA | GTTGCTCGAT | CCCGTCGCGA | CCCCGGAGGC | TACCAGGCAA | GAAACCCCGA | 8100
| CCTGCAGGC | CATCATCGCG | TCGGTGCCCG | CGTCCGCGGT | CCGGCTCACC | GAGCGCAGCA | 8160
| AACTGGCCAA | GCAACTTCTC | ATCGGATACG | TCACGTCGGG | CACCCTGATT | CTGGCTGCCG | 8220
| GTGCCATCGC | GGTCGTGGTG | CGCGGGCACT | TCTTTGTACA | CAGCCTGGTG | GTCGCGGGTT | 8280
| TGATCACGAC | CGTCTGCGGA | TTTCGCTCGC | GGCTTTACGC | CGAGCGCTGG | TGTGCGTGGG | 8340
| CGTTGCTGGC | GGGCGACGGTC | GCGATTCCGA | CGGGTCTGAC | GGCCAAACTC | ATCATCTGGT | 8400
| ACCCGCACTA | TGCCTGGCTG | TTGTTGAGCG | TCTACCTCAC | GGTAGCCCTG | GTTGCGCTCG | 8460
| TGGTGGTCGG | GTCGATGGCT | CACGTCCGGC | GCGTTTCACC | GGTCGTAAAA | CGAACTCTGG | 8520
| AATTGATCGA | CGGCGCCATG | ATCGCTGCCA | TCATTCCCAT | GCTGCTGTGG | ATCACCGGGG | 8580

FIGURE 1-12

```
TGTACGACAC GGTCCGCAAT ATCCGGTTCT GAGCCGGATC GGCTGATTGG CGGTTCCTGA    8640
CAGAACATCG AGGACACGGC GCAGGTTTGC ATACCTTCGG CGCCCGACAA ATTGCTGCGA    8700
TTGAGCGTGT GGCGGTCCG  GTAAAATTTG CTCGATGGGG AACACGTATA GGAGATCCGG    8760
CAATGGCTGA ACCGTTGGCC GTCGATCCCA CCGGCTTGAG CGCAGCGGCC GCGAAATTGG    8820
CCGGCCTCGT TTTTCCGCAG CCTCCGGCGC CGATCGCGGT CAGCGGAACG GATTCGGTGG    8880
TAGCAGCAAT CAACAAGACC ATGCCAAGCA TCGAATCGCT GGTCAGTGAC GGGCTGCCCG    8940
GCGTGAAAGC CGCCCTGACT CGAACAGCAT CCAACATGAA CGCGGCGGCG GACGTCTATG    9000
CGAAGACCGA TCAGTCACTG GGAACCAGTT TGAGCCAGTA TGCATTCGGC TCGTCGGGCG    9060
AAGGCCTGGC TGGGCGTCGCC TCGGTCGGTG GTCAGCCAAG TCAGGCTACC CAGCTGCTGA    9120
GCACACCCGT GTCACAGGTC ACGACCCAGC TCGGGCGAGAC GGCCGCTGAG CTGGCACCCC    9180
GTGTTGTTGC GACGGTGCCG CAACTCGTTC AGCTGGCTCC GCACGCCGTT CAGATGTCGC    9240
AAAACGCATC CCCCATCGCT CAGACGATCA GTCAAACCGC CCAACAGGCC GCCCAGAGCG    9300
CGCAGGGCGG CAGCGGCCCA ATGCCCGCAC AGCTTGCCAG CGCTGAAAAA CCGGCCACCG    9360
```

FIGURE 1-13

```
AGCAAGCGGA GCCGGTCCAC GAAGTGACAA ACGACGATCA GGGCGACCAG GGCGACGTGC   9420
AGCCGGCCGA GGTCGTTGCC GCGGCACGTG ACGAAGGCGC CGGCGCATCA CCGGGCCAGC   9480
AGCCCCGGCGG AGGCGTTCCC GCGCAAGCCA TGGATACCGG AGCCGGTGCC CGCCCAGCGG   9540
CGAGTCCGCT GGCGGCCCCC GTCGATCCGT CGACTCCGGC ACCCTCAACA ACCACAACGT   9600
TGTAGACCGG GCCTGCCAGC GGCTCCGTCT CGCACGCAGC GCCTGTTGCT GTCCTGGCCT   9660
CGTCAGGATG CGGCGGCCAG GGCCCGGTCG AGCAACCCGG TGACGTATTG CCAGTACAGC   9720
CAGTCCGCGA CGGCCACACG CTGGACGGCC GCGTCAGTCG CAGTGTGCGC TTGGTGCAGG   9780
GCAATCTCCT GTGAGTGGGC AGCGTAGGCC CGGAACGCCC GCAGATGAGC GGCCTCGCGG   9840
CCGGTAGCGG TGCTGGTCAT GGGCTTCATC AGCTCGAACC ACAGCATGTG CCGCTCATCG   9900
CCCGGTGGAT TGACATCCAC CGGCGCCCGGC GGCAACAAGT CGAGCAAACG CTGATCGGTA   9960
GTGTCGGCCA GCTGAGCCGC CGCCGAGCCGC TCCAGCGCCT CCAGCCGCGA CCCGCCCGTC  10020
ATTTGCCGC TCTCCGGAAT GTCATCTGGC TCCAGCACAA TCTTGGCCAC ACCGGGATCC  10080
GAACTGGCCA ACTGCTCCGC GGTACCGATC ACCGCCCGCA GCGTCATGTC GTGAAAGCC  10140
```

FIGURE 1-14

```
GCCCAGGCTT GCACGGCCAA AACCGGGTAG GTGGCACAGC GTGCAATTTC GTCAACCGGG    10200
ATTGCGTGAT CCGCGCTGGC CAAGTACACC TTATTCGGCA ATTCCATCCC GTCGGGTATG    10260
TAGGCCAGCC CATAGCTGTT GGCCACGACG ATGGAACCGT CGGTGGTCAC CGCGGTGATC    10320
CAGAAGAACC CGTAGTCGCC CGGTTGTTG TCGGACGCGT TGAGCGCCGC CGCGATGCGT     10380
CGGCGCCAACC GCAGCGCATC ACCGCGGCCA CGCCGACACC GGGATCATCG TGCAGTGGCG   10440
GCGTCGCGTG CCGCCCGAGC CGCCGACTCG TTTGTCGATG ACACCGGCGT ACCGTCATCT    10500
GCAGACTCGC TGCGATCGGG CCGAGGCCGC TGATCGGTCG ACGGAGGGCG GGCAGGAGGT    10560
GCCGTCCGCG CCGAGGCCGC CCGCGGTGCTC GGTGCCGCCG CCTTGTCCGA GGTAGCCACC   10620
TGCGTCCGCC CAGTGGCAGT ATGCGGACCC CGGAAAAAAA AAACTCGAGT GCGTTCTTCG    10680
GAGGTTTCCA ATTCTTGGAT TCCAGCACCG GCTCAGCGGT CTCGGGACC AGACTGACAT     10740
TGGCCCCATG CGTCGCCGTG ACCAATGAAT TGATGGCGGT ATGGCGCTCA TCAGCATCCA    10800
GGCTAGAGTC ATTCTCCAGG ATATCGATCT CCCGTTGAGC GCCATCCACA TTATTGCCGA    10860
TATCGGATTT AGCTTGCTCA ATCAACCCGG CAATATGCCT GTGCCAGGTA ATCACCGTGG    10920
```

FIGURE 1-15

```
CGAGATAATC CTGCAGCGTC ATCAATTGAT TGATGTTTGC ACCCAGGGCG CCGTTGGCAG   10980
CATTGGCGGC GCCGCCGGAC CATAGGCCGC CTTCGAAGAC GTGGCCTTTC TGCTGGCGGC   11040
AGTGTCCAA TACATCGGTG ACCCTTTGCA AAACCTGGCT ATATTCCTGG GCCCGGTCAT    11100
AGAAAGTGTC TTCATCGGCT TCCACCCAGC CGCCCGGATC CAGCATCTGT CTGGCATAGC   11160
TGCCCGTCGG CCTGGTAATA CTCATCCCCT ACTGCCCTCC CCAAACCGCC AGATCGCCTC   11220
GCGGATCACC GTCCGGTTGG CCTCCGGCAT TTCACGCCGG CTCGGCCGCT GGATCCACCC   11280
CGGCGCCGGTA TTCGCAGTAA CCCGTTGAAT CCGCGCGCAT GATGCACCGC TTGGGCGATC   11340
AGCCGGGTGG TCACCTCGCT TGCGCTGGCC GCGCTGTCGC ACGGGGCGCT CGGTGGTAAC   11400
GGACGTCATA ATTAACCAGC GTAACCGAAC CTAAGACCAG CTAGCTGCGG CAATATTGGC   11460
GACCAGGACT ATGGCGCCCT CCGAACCCGG GCTGAATGAC CGCATTGCGG TCAAAACATT   11520
ACTCACGCCG TGTCGGGCGC GCTGAATGAC CGCATTGCGG CGCTCATTCG GTGCGTAGTC   11580
GCTACCACCG CAACAATGGG CTTAGGCCAT TCCTTCGTTC ATCGGCGGGG ACATGGCCGA   11640
TAACGCAGCG GTCAGCTGCT CGCCCGCCGC GTCGTTATAC GCGGACGCCG CGGCCTGCGC   11700
```

FIGURE 1-16

```
ATTGTGCAGC GCCTCGTTGA CCCGCTGAGC CGCCGCCTCG GCACCCAGCT TCTTCAGCAA    11760
ACCATCTTCG ATGCGCAGGC CGGTGAGCCA CTGGTGCCCA TTGATCGTCA CTTCGACGGT    11820
CTCGGCTTCG TCGGTGGCGC GGAAGGATCC GTTGTTCATC TGATTGAGCG TCCCGTCTAG    11880
GGCCGACTGA AACCGCGCCG CCAGCGTCAA CGCCCGGGCG ACATGCGGGT CCAATTCGTC    11940
CATGCTCACT TCGACTCCTT ACTGTCCCTGG CGCCGACGGT TACCAATGAC GGCCTCGGTC   12000
CATGCCCGAT CCTCGGTGTA GAGCGCCTCG TCTTCCTGCT GAGAACCCTT GGACTTGGCG    12060
CCCCCTTGTC CCTGATGCGC GGCACCCATC GGCATTCCCA TGCCACCGCC GCCAGCGCCG    12120
GCGCCGCCGC CGGCCCTTCC CTGGCCTAAG CCGGCAATGT CACCAGCGCC AGCGGGCCGC    12180
ACCGATTCGG CGCCCCCGAT CGCGGATCCC AACGGGCCCG ACGTCGCCCG GCCGCCTCCA    12240
CCGCCACCGA GCGATGCCGC TTTGACCGCC ACGTCGCCCG ACAGCGCTGC GGCTTCCCGC    12300
CCAGCCGACG TCAGCTGCGC CGCCGTGTCA GCCGGGAGGC CACCACCCGG CGATCCGGTA    12360
GGCGGAACCA TCGGTGCGGC TGGCATCCCG GTACCGGGAG TCACACCGGA GCCGTCAGAC    12420
GGCGGCATCA GAAGCCAGG GATCAAATCCC TGCTCTTGCG GAGGCGGGGC GGGTCGATCT   12480
```

FIGURE 1-17

```
TGATGGCGGG GGGGAGGCTT CGGCGGGTTT ACCGGTTCCA GGGCTGCCTT GTTGTTGTAT   12540
TCGGTCAGCA CCTTCTCCGA CCTCTGCTGA TACTCCGCGT ACACCGGGAG AATTTGGTCG   12600
CGGGCCGAAG GGTTTTCCGC GTAAAGCCGT TCGAGCCCGA CTATGTCTTC ATAAGTCGGA   12660
TGTTCCCGCC TAGCCCACAC GTGCAGCTGC GCGACATATT GAGCCTGCTT GGCCATCGCA   12720
GCGCTCAATT TGGCCATGTG GAGTATCCAT TGCCGGTGTT GATCGAGCGA AGCCTCGCAA   12780
GCGGTAGCCG CATCGCCTTC CCAGTGTCA AACCCCCGGA ACCGCTTGAC GTCGCCTTGC   12840
AGCGTCAGT TGAAAGTGTT CCACCCATCC GCAAAGTGCG CGAGCGATGC GCCTTGGTCG    12900
CCCGTTTCGA GCTTCCTTGC CGCTTCTTTG AGATCCATGA AGTTGGGTTC ACCGGCCGTG   12960
GCCACCCTCG GCGTATCGGT TAGTTCGGCC GAACTGTCCC CTCCGACGGC CCCGGCCCGAT  13020
TCTGCCTGCA CAGTTCCTTC GCCGTCGTTG TCCAGGCGGG TCGCAGCCTC CTCATCAACC   13080
TCGCCATACG CCTTGGCCGC GAGGTCGCCA GACGCTGCCG CTCTTTGGCA             13140
CCGGCCGCCA GGTATTCCCG CATGTGTCG GCGGACAATA CCAGCTGTTG GGCGGGGTTT   13200
TTAGCCGCCG TGAGTTCGCA CGGTGTGATG GGGACATCAG TCGGTGGGTC CGCCATCGGG   13260
```

FIGURE 1-18

```
GCCTCCACCT CGTTGGCCCT GTTCAAAATC TCTTGCTGAT CCACCGTCAC GGTCTGCGAC    13320
TGGGTCATAT CGGATCATCC TCCTTAGTGC TATAGCCATT ATCGTCGCTA AACTGAAAGG    13380
TTCCTGCACT AATTTGATGC CGCCCGTTCA TGCCGGCATC GCGAACGGAT CGCCCTACTT    13440
CGGCAGCGCC ATCTGGTAGC GGCTTTCCTC GGGTGGGGAA ACCCGGCGAA TCGGCAGCTG    13500
CCGATGCCGC GGGGTACCGA TCACATTGTG CCGCAGAATC ACCCGGTCAA TACCGGGATG    13560
CGGGCCCGAGA TAGGTCGTCG CATTCGGCCA CGCCACCTTT ACCTCCTGCC CGATGTGTGC    13620
GCCGATCAAC CGGGCAAATT CCTCGAACTG TGGCCCGACT GTGACCATCG CACCTGCCGC    13680
CGCCGCACGC ACCACGAACT GGGTGAATGT CTGAGCGTCA CCCAGGTTGA GGGCGATGTC    13740
GACATCGTCG AAGGGCATGT AGACCGGGCA TCGGTTCACC GTCTCGCCGA CCAGTACCCC    13800
AGCTGACCCG ATCGGCAGCT GGCAGTGGCG GTTGGCCACC AGATGCTGGC CTTGCAGCGC    13860
GGGCCGCTGC CCGCCAAATA GGCGGGGCAA GCCCCTGGGT GTCTTGGGCT TGTCCGCCGT    13920
GGTCAGCAAC ACCGTGGACT GCGGGGCCAT CCCCGGCGCG ACCCGGACTC TGGTGATGGT    13980
GTGGTCCGCG CGCGCCCGACC ACCATACATC CGGACCTCCG GGCGCCGCGT AGGCGGCAGT    14040
```

FIGURE 1-19

```
GTAGGCATCG CGCCCCTTGA TCATCGACCA TTTCTCCCGC ACAAAGCCGA TGTCGGTGGC    14100
GTGGTCGTAG TCATCGAAGC TGCGGCCACA CACCGCGTCG ACACCATGGC TAGCCAGTCG    14160
ATCGGCAATG CGCGTCGCGG AGCCACCAA  ATACCGGGCC AGTCCTGCGA CGCCTTCATC    14220
GCGGCGCTGC GCCGATTTGC GGGTGCGTTC CGGGTCGGCG CGCAGCACGA TCCAGGTCCG    14280
GCGGTTCGCC GGCGCCGGGT CTGTCCCGAT CACCTGCTGA TACAGACTCA CCACGTCCGG    14340
CGCTGCCGGTA TTGCCGACGC GGTAGCCCGGC TGAGACGATA TCGGCCTCCA AGTCGGGACA    14400
GTGCACCGAC AGGAGCTCCT CCACCAGTCC GGTGTCCAGC ATGTCGTCGG TGTGGGCTTG    14460
CCCGTCGACG ATGACCGTCG GCGTGAATGG AGCTCGATTA CGGCGACCAG    14520
AAACTCGCCT TGCCAGCGCA ATCTCCTGGC TTCACGGTGG CCCCGACCAC    14580
AGGTTCTGAC GAGGAATCCG GCGCCGCCGC AACCACGCGT ACACCGCCGC    14640
CACCCAGCCG GTGATCCGGC GGCCGTAGAA AGTGACCGTG GCCACGATGA CGCCCAACGA    14700
GGCCAGCGCA ATCCCCGCCC ACCAGTAGCG CGTCTCCAAG AATGCGATGA TGCATGGCGG    14760
GGCCAACGCG GAGGCAAGCA AGGGGTGCCC GGTGCTGAAC CGCAGCCCTA AAGGATTTCT    14820
```

FIGURE 1-20

```
CATCGGCGGC TCAGGCCCCG TCTAGCCAGC GCGCCCAGGC CCAGGGCCAA CGTAAGGCCG    14880
ACGGCCACCA ACGCCACAGC CGTAATCGGG CGACGATCGG GACCCGGCTC CACCACCGGG    14940
GGTGGAAGTC GTCTGACGTT GTATGGCGCC GAAGCAGGGC CGGGCGGAAT GTCCCACGTC    15000
AGCGCGGCCA CCGCATCGAT GACGCCGGCG CCGACCAGT CGTCGACCCC GCCCCCGGGG     15060
TGTCTCGCGG TGGCGGTGAT CCGGTGGATG ATCTGCGCCG GCGTCAGGTC GGGGAACCGC    15120
TGCCGAAGCA GGGCCGCCAG ACCCGACACA TATGCCGCGG CAAACGAGGT GCCGGCGATG    15180
GGTACCGGCC CCTCCCGGCC TTGCAACGCA TTCACCGGTT CACCGGTGTC GCCGAGCGCG    15240
ACGATGTTTT CTGCGGGCGC GGCCACGTCC ACCCACGGTC CGTGCATCGA GAACGAGCTG    15300
GGCATCCCCGG TCTGGCCGAT ACCGCCGACG CTTAACACCA GCGGTGCGTA CCACGCCGGG   15360
GTGACAACGG TCTGCACATT GTTCCAGCCG CGTGGGTCGC CGGGTGTGGA CGGGTCCGGC    15420
GCCGGATTCT GTACGCAATC GCCACCGGTG TTGCCGGCCG CGACCACCAC CACCACGCCT    15480
TTGACGTTGA CCGCATAGTC GATGGATGCA CCCAGTGAGG TTTCATCGAT CGGCCTGCTC    15540
ACCTTGTAGC AGGCGGCTTC ACTGATGTTG ATCACACCCA CGCCGAGGTT GGCGGCGTGC    15600
```

FIGURE 1-21

```
ACCACGGCGC GGGCAAGACT GCGGATGGAA CCGGGCGGCCG GGGTGGCGTT GGGGTCATTC    15660
GGGTTGGCTT GTGAGCCGAC CGGTTCGAAG GCCTCAGACG TCTGACGTAG CGAGAGCAGT    15720
CGAGCGTCGG GCGCGACGCC GACGAACCCG TCGGTGGGCG CGGGCCGGCC CGCGATGATG    15780
GATGCTGTGA GAGTCCCATG GGCATCACAG TCAGACAGGC CGTTACCGGC CTGGTCGACG    15840
AAATCGCCGC CAGGTTCCGC CGGGACCCGT GGCGAAGCGT CGACACCGGT GTCGATCACC    15900
GCCACCGTCA CCCCGGCCCC GGTCGCGAAC TTGTGGGCAT CGGCCACGCC CAGATACGTG    15960
TTGCTCCACG GCGGATCGTG GAACCCGGAC CCCGGCAGCG TGGTGGGCGA CGGCACAAA    16020
ACGCGCTGTT CGGTAGGCTG ATCCGGCCCC GCCACGTCGG GCGGCAACGC GCCCGGATCG    16080
ATCGGCGGTG GCGTGATGGC CGATGCGGGC GACGCGGTGA GCAACGCCAG CGCCACCGTG    16140
ATCAGAAAGA TACGGTGCAC TCCCAGAACA CTCCATTCGT TGAGATTCAT TGCGGATTCAT    16200
TGAGCTGCGT TGCTACCTTG GGCCACTTGA CGGACCTGTG TGCATTTTAG ACGTAACGGC    16260
TGGGCAAACA ACGCTGTCAC GCCTGGGCTG GTCCGCCGCG CCGACCAGGG CGCGTAGGCG    16320
CTGTACCTGG ACCACGCCGG GACTCAACGG TTTGCTACC GCACTAGCCG ATATGCGGCT    16380
```

FIGURE 1-22

```
GCTACCAAAC GATCGCGGCC ATGTCTCGGT TGTCTGAGCA CACGCTGCGT ATCGCGGCAT    16440
CGATGTCGGT GGCGGTGATG ATCTGCAGAT CCTGAACCGA TACCGGTTGG CCCGCACGTT    16500
TTTGCGCAAC CACCCGGGTG TCCCGGAACC CTTCGGCGCG TTCGATCACG TTGCGGGCGA    16560
ACCGACCGTT TTGCATAGCG TCGATACCGT GCTGCCCACT AGGGGTGGTG TAGTTACGGA    16620
TGGTGGTGAC CGCGTCGAGG AATACCTCCC GTGCGGCGTC ATCGAGCTGG CTGGCGCGCG    16680
GTGTAGCGTA GCGGTGTCCA ATCTCGACGA TCTCCACCGG CGAATAAGAC TCGAACCGCA    16740
GCTTTCGGTT GAACCGGCCA GCCAAACCCG GGTTCACGGT GAGGAATTCG GTACCCCGGG    16800
TTCGAAATCG ATAACTTGGA TCCGGAGAGC TCCCAACGCG TTGGATGCAT AGCTTGAGTA    16860
TTCTATAGTG TCACCTAAAT ACTTG                                         16885
```

FIGURE 2-1

```
GGATCCTCGG ACTGGCCGCG GTCGTGCTTG TGCACGAGTT CACCGAGGTC ATCGTCATCG    60
CCAACGGGCGT GCGGGCCGGA CGCATCAAAC CACTTGCCCGG GCCACCCAAG ACACCTGATC   120
GGACTATCCC GGGGTAGCGA CGGCGCGGAAT CGTGGAGTGT GTTTGGACCA GCAATAGCGT   180
CACTGTGACG AAACAGCCGC CGTCTTCTGG AAGTTATACC CGGTTATACT ATCTGTATGA   240
AGACAGCTAT TTCTCTGCCG GATGAGACGT TCGATCGGGT ATCGCGGCGT GCGAGTGAGC   300
TCGGCATGAG TCGGTCCGAG TTCTTCACGA AGGCTGCGCA GCGCTACCTG CACGAGCTGG   360
ACGCCCAATT GCTCACGGGC CAGATCGACA GGGCTCTAGA GAGCATCCAT GGCACCGACG   420
AAGCGGAGGC CCTCGCCCGTG GCCAACGCAT ACCGGCGTGCT AGAAACCATG GACGATGAGT   480
GGTGATTAGT CGTGCCGAGA TCTACCTCGGG CCGCCATCAG GCAGTCAGCC   540
GGCGAAGCGC CGCCCGGTGC TCGTAATCCA GTCAGATCCG TACAACGCAA GTCGCCTTGC   600
CACTGTGATC GCAGCGGGTGA TCACGTCCAA TACGGCGCTG GCGGCAATGC CCGGCAACGT   660
GTTCTTGCCC GCGACCACAA CGGACTGCC ACGTGACTCG GTCGTCAACG TCACGGCGAT   720
TGTCACGCTC AACAAGACTG ACCTCACCGA CCGAGTTGGG GAGGTGCCAG CGAGCTTGAT   780
```

FIGURE 2-2

```
GCACGAGGTT GACCGAGGAC TTCGTCGGGT ACTGGACCTT TGACACTGCG CCACGCGACA    840
ATTCGTCACG GTGACGTTCC TGCTTGGTGT AAGCCCCCCC GCCGGGGAA CTACTCGCCG    900
GAGGTGGTGT TGTGGGCAGG CTTGAGGGCA AGTTGCATT CATTACGGGC GTGGCTCGGG    960
GTCAAGGCCG TTCGCATGCG GTCCGCCTAG CCGACGGCCA AGCGCGTGCG CTCGGCAAGG   1020
TCGATGTTGA GGGCATCCGT GCGCTGCGGT GTGAGGTAGA AGTGTGGGGC CGTGACGTGC   1080
GTGACGATCG ACGGGTGTTT GTCGAGAGTC CTGCCGTTTC ACAGAGGGAA CTTGTCGAGC   1140
TCGGCCGTCA GGGCATCCGT GTCGTAGGGC TGCCGTAGGC GTTCGGGCCG TGCCGCCGCG   1200
CCGAAGCCGG GTGCGGGGCG AGGCGCTCGG CTGCTGGCTC CCAGTAGACA TCTAGGCCTG   1260
CGTCGACTGC GGCTGCGGCA GCGTCGTGCT GGTGACGAGT GGCGTTGGTG TCCAGCGTGA   1320
TCGCAGTGGT GCCGGGGTGG TCGCGGGACA GGAAGTCCTC GACCGGTTTG TGATCACCCG   1380
GCCCGAGCCG AAACTGAATG CCCATCGTCG TGAAGTTCCT CTCGCATCGA CGCCTCGGTT   1440
CGTGTCATAA TACATGACAA ATCAATAGAC AAAAGGAAGA CAGGCTGCCC ATGGGAGTAA   1500
ATGTGCTCGC CTCGACCGTG TCGGGTGCGA TCGAGGCGCTT GGGATTGACC TACGAGGAAG   1560
```

FIGURE 2-3

```
TCGGTGACAT CGTCGATGCC TCGCCGCGTT CCGTGGCGCG ATGGACCGCA GGTCAGGTGG    1620
TTCCCCAACG CCTCAACAAG CAACGACTTA TCGAGCTGGC CTATGTCGCC GACGCCCTCG    1680
CGGAAGTGCT GCCGGTGAC CAGGCGAACG TGTGGATGTT TCGCCGAAT CGGTTACTGG      1740
AACACCGCAA GCCTGCCGAC CTCGTGCCGAG ACGGCGAGTA CCAACGCGTG TTGGCGCTCA   1800
TCGACGCGAT GGCGGGAGGA GTGTTCGTGT GAGGCGATGCC CTCGATGAAG GGCTCGTCCA   1860
GCGTATCGAC GCACGCGGAA CAATTGAGTG GTCGGAAACG TGCTACCGGT ATACCGGCGC    1920
GCACCGTGAC GCCTTGTCCG GTGAGGGCGC GCGCAGATTC GGAGGCAGGT GGAATCCGCC    1980
GCTGCTCTTT CGGGCGATCT ATCTTGCTGA TTCCGCCCAA GCCTGCATGG TTGAGGTGGA    2040
ACGGGCGGCG CAAGCGGCTT CAACGACCGC AGAGAAGATG CTCGAGGCGG CCTACCGACT    2100
ACACACGATC GACGTCACGG ACGACATCTA TGGCGACGAC CTCGATCTG ACAACCCCGC AAGCTCGGGA 2160
AGCCGTGGGG CTCGAGAACG ACGACATCTA TGCACATGCA AGGTGTCCTC GTGCCGGCGG   2220
CGGACATGCG GCCTGGTTCT TGCACATGCA AGGTGTCCTC GTGCCGGCGG CGGGGGTGT    2280
CGGCCTCGTT GTCACCGGT ATGAACAGCG AACTGGCCG GGCCAACTAC AACTGCGACA     2340
```

FIGURE 2-4

```
AAGGCGTCGAT CTGACGCCTG CTCTTTACCA AGAACTTCGA GCCACGTAGC TGGCCAGCTT    2400
GGCGCAGAGA AGGATGCCGC TGTGCCATGG TCATCGTAAG GAGCAACTCG CATCACTTAT    2460
AAGCCGATAA GCGACATTAT GTCAAGTGAA GCTGGTCGTA TGGGGTTAGC TGCGCCGTTT    2520
GTGCTAGCGG GCACGCTCCT TGTGCGTGCT GCGGCAGCGA GCGTGTCGTC AAAGGTTGCG    2580
AGGCTTGCCT GGTGATGAAT TGCCACATCC GGCACGCAGC AATCAGGTAG TTTTAGCCCG    2640
CTGCTAGCGC GTAGTTCGGC GAGACGCAGC AGCTCGCCAT CGTCGTACGG CGCAACGACG    2700
CTACCCGCGG AACGCGGATC GTCGAGCATC GATGATCAGG CGCCGCAATA ATTTGGAACG    2760
GGGCTCGCCA GGCCATCGCT GGGCGGCCCG GTCCAATGCC TGAGCTACCT CCGGGGTTTC    2820
GGTTATTTGG TAGCGCGGAC GAGTGGTCGA CATAGAACGA AGTGTGCCAC TTCTAGCAAA    2880
GGTGGTACAC CTACTGGCGG CCGGGGTTT ACCGCCCCTG CCAGTCACCG CACTTCCGGC    2940
GGCGGACGAC GAGCACCGCG GAATCCACAT GCGGCGGGTGG CAGGAACGCG CGCCGTGGCA    3000
GCATGAGGCC GACGGTCAGG GTGAACCTTC GCGCGTTGCG AGAAGCGAAT TTACATACGA    3060
GGGCTCGCTG CAGCACGAGA TCGGCCGCGA CAAGCCCGCT GTTGGGTGCC AGCAGCGTCC    3120
```

FIGURE 2-5

```
GCAGCAGCCG GGACGAAATC CCGTACGGCG GGTTCGCCAC AACCCGGAAC GGCCGGGCCGG    3180
GCAACCCGGAT CGAGGCGGCG TCCGGTGCA CCACGGTAAT GCCAGGGAAT CGCTCGCGGA    3240
GGACACCGAC TCGTCGCGGG TGCAACTCCA CGGCGACCAC CCGGCCCCCC GCTCGCACTA    3300
GATGCGCCGT CAGTGCCCCT TCGCCGGCGC CGATGTCAAA CACGAGCTCA CCGGACCGCA    3360
CTGCGGCCGC GCTGACTACC CGCGCTGCCC ATTCGTCATG GAGCCGGTGC CAGCCCCATG    3420
CCCGTCGCGA CCGTCCGAGG GCGGACACGA CGTACCGTCA CTGCGTAGAT GCCCACGCGC    3480
CCGACCGTAG CCCGCCACCG GCACTGCGAT CAATCCAATT TCTCGGTTCA GGCAACCTTC    3540
TGGTCATCAC CAGCCCCAGG GCTCTGGGCG CGTCCGCATC AACTCCGAGA TGACGTTGGC    3600
CGTGACGACC CACTAGACCC ACCTGGCAGT AGCCGCATTG TCGCAGTCGG CGAGCCTCAG    3660
TGCGCAGTCG CGTCTAGGTG CAAGGATATT GCCCGTTGAG CAGACAACTC GACGGCGGCG    3720
AGTAAGAACC GGTCAGCCCG CCTCTTAGGC CGCCCGTGGC TGAACCACCG GGGGCAATGA    3780
TGCGATTCCA ATTCGCTGGG CTGAGAACGT AGTGGCGTGCC AGATCGTGCA ACGGTGCTAT    3840
TCCATGTGTG CAAGACGGAT TCTCCTGCCG GCAAGTCGAA TTCAAGCTTC CAATCGGTTA    3900
```

FIGURE 2-6

```
GCGGCGCCGT GCTCGAGTTT GTGATGGTGA AGCGGGGGAT GAAACCGGTC TGCCACGTCG    3960
ATGTCACCGA CAACGTCGCC CTGGCCGTCG CCGCACTAGC GACCGGGGTG ATGGCGAGTC    4020
CGAGGATGGC AACTATCAAT GCCGACACGG TTGCCGTGAAG CGCTGTCCGC CAGCGCCTCA    4080
CGTAAATGTT CAGTCCGGCC ATGACAGCCA ACACTAATGC CAATGAGGCG ATATCGGCCG    4140
TCTCCTCGCG AGCAAGCTAC AGCAACTTTG CTCAACCGCA ACCGTGATGA AATTTGGCCT    4200
CGACCCACCC TGAACCAGAT ATCGGCCCGG CCGAACGCGA ACTTGCGGAC GGGGAAGGCC    4260
AGACAGCCTC GACCCCACTC CCCCGATTAG CGCCGTTCAC CGTTCGCGAC CGGTATCAAC    4320
GGGCTACAGC TCCAACACGA TCCGTAGGGC CGCGTCGGCG TGTCAGCTGG CTGGTGGCGC    4380
CGACACGCCC GGGCGAGGCC GCCGTCGGCG TGTCAGCTGG TGACTGAGTT GTGCAGACTG    4440
ACCGGGGCC CTCCTGCCGA ACGGTATGTG CCCATGACG ATCACGTGGT CCAACCCGCG    4500
TGTGCACACG TGCTGTACTA GGTCACGGTC AGCGAGATTC CCAGCGCAAC CATCATGACC    4560
GCGATCAGGC CGTCGAGGAT TCTCCACGAG CCGGGGTTGG TGAACAGCCC GCGCAACCGG    4620
CCGGCTCCGA ACCCGAGGGT GGCGAACCAT ACCGCACTGG CTGTGACCGC GCCGAGGCCG    4680
```

FIGURE 2-7

```
AACAGCCAGC GCTGGTCGCT GTGCTCGTTG GCCAGCGCGC CTAGCAACAC GACGGTGTCG  4740
AGGTAGACGT GTGGGTTGAG GAACGTGAAT GCCGCACAGG TCACCAGGAC CTCGGCTAAG  4800
CGAACCGGCG TGGCGCCAGA GCAACAGGTC GCAACAGGTC GCCACGCCCG CCGGGCCGCA  4860
AGTAGCCCGT AGCCGATTAG GAAGGCGGCG CCGCCAAACT TGACGACATT GAGGCACGC   4920
GGATGTGCGC CGATCAATGC GCCGAACCCC GCGATACCGG CGGCGATCAG CACGATGTCG  4980
GACACCGTGC ACAGCGCCAC CACCGGGCAGC ACGTGCTCAC GCTGGATTCC CTGCCGCAGC  5040
ACGAATGCGT TCTGCGCGCC AATCGGGGCG ATCAGCGGTGA AGCAGGCCAG GAAGCCGACG  5100
ACCAGTGGTG AGTTCACGCA ATCGACACTA GGCAGTTTGT ATGGGTCAGT ATAGCTAATA  5160
ATTCTTCATT TACATTAGCA TTATTAAATGT GCAGTGCGAC GCTCCGCAGA TGGTCTACAC  5220
CTGAGATGGT GGATCCGCAG CTTGACGGTC CACAGCTGGC CGCATTGGCT GCCGTGGTCG  5280
AACTGGGCAG CTTCGATGCG GCCGGGAGC GCCTACATGT CACCCCCTCG GCTGTCAGTC  5340
AGCGCATCAA GTCGTTGGAG CAGCAGGTCG GCCAGTGCT GGTGGTCAGG GAAAAGCCAT   5400
GTCGGGCGAC GACCGCAGGT ATCCCGCTGT TGCGGTTGGC CGGCAAACA GCGTTGCTCG   5460
```

FIGURE 2-8

```
AGTCCGAGGC GCTCGCTGAA ATGGGTGGCA ACGCGTCGCT GAAACGCACG CGGATCACCA    5520
TTGCGGTAAA CGCCGATTCC ATGGCGACAT GGTTTTCGGC CGTGTTCGAC CGTCTCGGCG    5580
ACGTCCTGCT CGACGTTCGG ATCGAGGACC AGGACCATTC CGGCGGGCTG CTACGGGAGG    5640
GTGTGGCGAT GGGCGCGGTG ACCACCGAGC GGAACCCGGT GCCGGGCTGC CGGGTGCACC    5700
CGCTGGGTGA AATGCGCTAC CTACCAGTGG CCAGCAGGCC ATTCGTCCAG CGCCATCTAT    5760
CCGACGGGTT CACTGCCGCC GCGGCGGCTA AAGCTCCGTC ACTGGCGTGG AATCGTGACG    5820
ATGGGCTGCA GGACATGTTG GTGCGTAAGG CCTTTCGTCG CGCCATCACC AGACCGACGC    5880
ACTTTGTCCC GACCACAGAG GGCTTCACCG CCGCAGGCGC CGCCGGGCTG GGATGGGGCA    5940
TGTTCCCCGA GAAGCTGGCA GCATCTCCGC TTGCCGATGG ATCGTTCGTA CGGGTCTGCG    6000
ACATACACCT CGACGTCCCT CTCTATTGGC AATGCTGGAA ACTGGACAGT CCGATCATCG    6060
CGGCGAATTAC CGACACGGTG AGGGGGCGG CAAGCGGTCT GTACCGGGGC CAGCAACGCC    6120
GCCGCCGACC GGGTTGACCG ACGCCAGCAT GTTGTTGTGT CAGCGCGGCT TGGTCTCGAT    6180
GTCCCGGCCT TGCTGGACCC GCTTCCCTCAA ACAGGTTGAA CTTAACGACT CAGACGGAAA    6240
```

FIGURE 2-9

```
CGCTTGAACC GCGACGTCGC TCCGGACACC AATTGACTC GGCTCTTTGG CAATTGAAGG  6300
TGAGCTGCGA GCAGCCGGGT GACCGCATCG TTGGCCTTGC CATCAATCGC CGGCTCGCGG  6360
ACGTAGATAA TCAGCTCACC GTTGGGACCG ACCTCGACCA GGGGTCCTTT GTGACTGCCG  6420
GGCTTGACGC GGACGACCAC AGAGTCGGTC ATCGCCTAAG GCTACCGTTC TGACCTGGGG  6480
CTGCCGTGGGC GCCGACGACG TGAGGCACGT CATGTCTCAG CGGCCCACCG CCACCTCGGT  6540
CGCCGGCAGT ATGTCAGCAT GTGCAGATGA CTCCACGCAG CCTTGTTCGC ATCGTTGGTG  6600
TCGTGGTTGC GACGACCTTG GCGGTCGTT GCGCTGGTGA GCGCACCCGC CGGCGGTCGT GCCGCGCATG  6660
CGGATCCGTG TTCGGACATC CGGGTGAGGCG TCGTCGACT GCTTACCTC CACGCATCAG GCTTCTGGTC  6720
TTGGCGACGT CGGTGAGGCG TTCGTCGACT CGCTTACCTC GCAAGTTGGC GGGCGGTCGA  6780
TTGGGGTCTA CGCGGTGAAC TACCCAGCAA GCGACGACTA CCGGCGGAGC GCGTCAAACG  6840
GTTCCGATGA TGCGAGCGCC CACATCCAGC GCACCGTCGC CAGCTGCCCG AACACCAGGA  6900
TTGTGCTTGG TGGCTATTCG CAGGGTGCGA CGGTCATGA TTTGTCCACC TCGGCGATGC  6960
CGCCCGCGGT GGCAGATCAT GTCGCCGCTG TCGCCCTTTT CGGCGAGCCA TCCAGTGGTT  7020
```

FIGURE 2-10

```
TCTCCAGCAT GTTGTGGGGC GGCGGGTCGT TGCCGACAAT CGGTCCGCTG TATAGCTCTA    7080
AGACCATAAA CTTGTGTGCT CCCGACGATC CAATATGCAC CGGAGGCGGC AATATTATGG    7140
CGCATGTTTC GTATGTTCAG TCGGGGATGA CAAGCCAGGC GGCGACATTC GCGGCGAACA    7200
GGCTCGATCA CGCCGGATGA TCAAAGACTG TTGTCCCTAT ACCGCTGGGG CTGTAGTCGA    7260
TGTACACCGG CTGGAATCTG AAGGGCAAGA ACCCGGTATT CATCAGGCCG GATGAAATGA    7320
CGGTCGGGCG GTAATCGTTT GTGTTGAACG CGTAGAGCCG ATCACCCGCG GGGCTGGTGT    7380
AGACCTCAAT GTTTGTGTTC GCCGGCAGGG TTCCGGATCC GATGACATAT GACGGGATGG    7440
TTCCCGTTAC CCCACGGGAA TCGATGATCG AGGGGACGGG TATGGGAGTC CCACCATCGA    7500
TCTTTACGTA CAGGGTGGTG ATCGGCGATC CGACGACCTC GACGTTGGGC GCAGGTAGCG    7560
GGTTGGGACC GAACACGAGC TCACCTGCGG GTGCGTCGAT GAGCACTCCC TGGTTGAGGT    7620
CACCCGGTAA CGCCATCGTC GGAATGCTGG GGCCTGGTCC CACCGCATTG GACCCAACTC    7680
CCAGAACGCC GTCCACGCCG ACGCACCGA AATAGGCTTC GAACGGGGTT GTTGTCGGAT    7740
CGGCCAGCAA GGCGCTGAAG TAGGTCGAAA TGGCGAAGGG GGACGTTGGG ATGGACAAGA    7800
```

FIGURE 2-11

```
GGACGACATT AACGGTGGTC GGCGCGGTGA CGATGCCATT CCCGAAGTCC ACCGTCGTGG   7860
TATACGTGGC GAAGATGTAG TACAGCCCCC CGCTGTAACC GCTGATGCTC AATCCGGTTG   7920
GGAGGCCCAT GTGAAGCACT CCCAGGATTC CCCCGACATC CTCAGGTGAG ACAACAAGAT   7980
CAGCGGATCC GGTGTCGACC AGAATGGTTG ACGTCGGTCC GCCGTTGACG TTGGCATGTA   8040
CCGTCGGCTC TGTGACATGA ATTATCTCCA GCGGGACGGT TCTGCCGTCG CCGCCTGGCC   8100
CACTGACGCC GTATCCGCCA TACAACAGGC CCGAGGCCGC CGGCTCCGCC CCCGTGCCAC   8160
GATCGACACC GACTCCATCA CCGCCGGCTC CCGTTGCCGA GTTCGCTCCC CAGCCCAAAA   8220
GTCCTGTGGC ACCGCCCGTT CCGTTGCCGG GCAGCCAGCC GCCGGGGATG CTCGACGCGC   8280
CCCCGGGCCC GCCGATCCCG GGCTCCCCCG ACCGTTTGCC GCCGGGCTCC             8340
CCGGGGGCGT TGGGCCCGCC GGCTCCCCCG GCCGGGCCAT TGCCGATCAA CGCCGCGGAA   8400
CCGCCGGCAC CGCCGCCGAC CCCCGCCCCG GCGCGGCCAT AACCGTTGCC GCCGTTGCCG   8460
TACAGCAGCC CACCCGCCCC GCCATTCGGA CTCGTTGCCG TCCCGGGGTGC TCCGTCGCCG   8520
ATTAGCGGAC GCCCAACAA CGTTTCGGTT GGTGCATTGA CCGCCCCAG CAGATCGTGC    8580
```

FIGURE 2-12

```
TGCGCGGTCT GCAACTGTGA CGCGATGGTG GCCTCCGCGG CCGCATACGA TCCTGACGCC   8640
GAGTTCAGCG TCTGCACGAA CTGTTGATGG AAAGCGCTCG CCTGCGCGCT GACCGCTTGA   8700
TATTCCTGAC CGAACCTGGC AAACAGCGCT GCCACCGCCG CCGATACCTC ATCAGCGCCA   8760
GCGGCCGCAA GCGCGGGTGGT CGAGGCGGCA GCCGGGGCAT TCGCCGCGCG CAGTGTGGAA   8820
CCTATGTTCT CCACATCCGC TGCCGCGGAC GTCAAGAACT CGGGAACCAC GACCAGAAAT   8880
GACACGCCGC CCCTCCGCCT CGATCACCAT CCCTGCCGCGC ATACAGCGTA TCCAGACGCT   8940
GCCTTTGACA TCTCGGATTT TCAGTAGCTA CCGCACGGCA CAGCACGCGT TAGGTAGATA   9000
GTGGCTATTT GCTGGTACCA TCTACCTGTG GCGCTGAATA TCAAAGACCC TGAGGTAGAC   9060
CGACTAGCCG CCGAACTCGC TGACCGGCTG CACACCAGCA AGACTGCCGC CATCCGGCAT   9120
GCCCTGTCTG CCCAGCTGGC GTTTTTGGAG TCGCGGCCG GGACCGTGA GGCACAACTT     9180
CTCGACATCT TGCGTACCGA AATCTGGCCC CTGCTTGCCG ACCGCTCCCC CATCACCAAG   9240
CTCGAGCGCG AACAAATCCT CGGCTACGAC CCCGCAACCG GAGTCTGAGC ACCGCAATGA   9300
TCGTGGACAC AAGCGCCGTG GTGCCCCTGG TTCAAGGGCA GCGGCCGCAC GCCACCCTGG   9360
```

FIGURE 2-13

```
TCGCGGCCGC CCTGGCCGGC GCCCATAGCC CCGTCATGTC TGCACCCACC GTCGCCGAAT  9420
GCCTGATTGT CTTGACCGCC CGTTGCGCC  CGTTGCGCG  CACGATCTTC GAACGACTTC  9480
GCAGCGAAAT CGGCTTGAGC GTGTCATCTT TCACCGCCGA GCATGCCGCT GCCACGCAAC  9540
GAGCCTTTCT GCGATACGGC AAGGGGCGCC ACCGCGCGGC TCTCAACTTC GGAGACTGTA  9600
TGACGTACGC GACCGCCCAG CTGGGCCACC AACCACTGCT GGCCGTCGGC AACGACTTCC  9660
CGCAAACCGA CCTTGAGTTC CGCGGGCGTC TCGGCTACTG GCCAGGCGTC GCGTAACCGT  9720
ATGCGCGGTG ATCGCTGTTT GTAATGAGTT CAGCGACACG AAGAATAAAA TATGGGTAGC  9780
CGAAATCACT AAGCTACAGT GCTGGTGCAC GCCATGAAAG ACCGTCAATG ACAAGGAGA   9840
CGGCCGAAAT GCCCAAGGAC CGACTGCCGG ACTTGACGCC CACAGGAGCG TACGCACCGG  9900
CCAACAGCGG CATGACCATG GCAAGGCAGG ACGGCCCTCG ATGACCGGCA AGCGCGTTGA  9960
GCGGGTGCAC GCAATCAATT GGAACCGGTT GCTCGATGCT AAAGATTTGC AGTCTGGGA  10020
ACGTTTGACC GGTAACTTTT GGTTGCCGGA AAAGATTCCG CTCTCCAACG ACCTGCATC  10080
TTGGCAAACG TTGAGTTCCA CCGAGCAGCA GACGACGATC CGGGTGTTCA CCGGCTTGAC  10140
```

FIGURE 2-14

```
CCTGCTCGAC ACCGGCGAGG CGACGGTGGG AGCAGTGGCC ATGATCGACG ACGCGGTCAC  10200
CCCCCACGAA GAGGCGGTCC TGACCAACAT GGCCGTTCATG GAGTCAGTGC ACGCCAAGAG  10260
CTACAGCTCG ATCTTCTCGA CCCTGTGCTC GACCAAGCAG ATCGACGATG CCTTCGACTG  10320
GTCGGAACAG AACCCTTACC TGCAGCGAAA AGCGCAGATC ATCGTCGACT ACTACCGCGG  10380
TGACGACGCG CTCAAGCGCA AAGCATCGTC GGTAATGCTG GAGTCCTTCC TGTTCTACTC  10440
CGGCTTCTAC CTGCCCCATGT ACTGGTCGTC GCGGGGTAAG CTCACCAACA CCGCCGATCT  10500
GATCCGGCTG ATCATCCGAG ATGAAGCCCGT CCACGGCTAC TACATCGGCT ACAAATGTCA  10560
ACGAGGTTTG GCCGACCTGA CCGACGCCGA GCGGGCCGAC CACCGCGAAT ACACCTGCGA  10620
GCTGCTGCAC ACGCTCTACG CGAACGAGAT CGGTTACAAC GCCAACAAGG CACGACGAGTT  10680
GGGCTGGACC GACGACGTTT TGCCCTACAT GCGTTACAAC GCCAACAAGG CGCTAGCCAA  10740
CCTGGGATAC CAGCCTGCAT TCGATCGTGA CACCTGCCAG GTGAACCCGG CCGTGCGCGC  10800
AGCTCTCGAC CCCGGTGCAG GGGAGAACCA CGACTTTTTC TCCGGCTCCG GAAGCTCATA  10860
CGTAATGGGC ACCCACCAAC CCACCACCGA CACCGACTGG GACTTCTAAC CGCCCAGCGC  10920
```

FIGURE 2-15

```
GTCGGGGGCG TCGAGCACCA CGGCGACACCG GGCCCGATCG ATCTGCTAGC TTGAGTCTGG   10980
TCAGGCATCG TCGTCAGCAG CGGCGATGCCC TATGTTTGTC GTCGACTCAG ATATCGCGGC   11040
AATCCAATCT CCCGCCTGCG GCCGGCGGTG CTGCAAACTA CTCCCGGAGG AATTTCGACG   11100
TGCGCATCAA GATCTTCATG CTGGTCACGG CTGTCGTTTT GCTCTGTTGT TCGGGTGTGG   11160
CCACGGCCGC GCCCAAGACC TACTGCGAGG AGTTGAAAGG CACCGATACC GGCCAGGCGT   11220
GCCAGATTCA AATGTCCGAC CCGGCCTACA ACATCAACAT CAGCCTGCCC AGTTACTACC   11280
CCGACCAGAA GTCGCTGGAA AATTACATCG CCCAGACGCG CGACAAGTTC CTCAGCGCGG   11340
CCACATCGTC CACTCCACGC GAAGCCCCCT ACGAATTGAA TATCACCTCG GCCACATACC   11400
AGTCCGCGGAT ACCGCCGGT GGTACGCAGG CCGTGGTGCT CAAGGTCTAC CAGAACGCCG   11460
GCGGCACGCA CCCAACGACC ACGTACAAGG CCTTCGATTG GGACCAGGCC TATCGCAAGC   11520
CAATCACCTA TGACACGCTG TGGCAGGCTG ACACCGATCG GCTGCCAGTC GTCTTCCCCA   11580
TTGTGCAAGG TGAACTGAGC AAGCAGACCG GACAACAGGT ATCGATAGCG CCGAATGCCG   11640
GCTTGGACCC GGTGAATTAT CAGAACTTCG CAGTCACGAA CGACGGGGTG ATTTCTTCT   11700
```

FIGURE 2-16

```
TCAACCCGGG GGAGTTGCTG CCCGAAGCAG CCCGGCCCAAC CCAGGTATTG GTCCCACGTT    11760
CCGCGATCGA CTCGATGCTG GCCTAGACTC GCGAGGACCG CGCGGTGGTC ACTGCGCGGA    11820
TTTGGGGCGG CGGAAGTGAG TGTTCGGTGC GCCCACTGCG GTGACTCACC TGCAGCGCCG    11880
GCATCGACAG GCCGGGAGCT CAAGAATCGT CGCTAGAGAA TCTATGGTGC GTTAGAGGAT    11940
TCCCTGCTAG ACAGCCTTGG TGCGGTGGTC GGCCCGGGGA CGAGAGGATA TGCGATCCAC    12000
AAGCTGGGTT TCTGCAGCGT CGTCATGCTC GGGATCAACT CGATAAATCGG CGCCGGTATC    12060
TTCCTAACTC CAGGTGAGGT GATCGGGCTC GCAGGACCCT TCGCGCCGAT GGCCTATGTT    12120
TTAGCTGGCA TTTTCGCGGG TGTCGTGGCG ATCGTCTTCG CGACGGCGGC AAGGTACGTC    12180
AGAACAAACG GTGCCTCCTA CGCCTACACA ACGGCCGCAT TTGGGCGCCG GATCGGCATC    12240
TATGTCGGTG TCACCCACGC CATTACCGCG TCCATGCTT GGGGGTGTT GGCTTCTTTT      12300
TTCGTCTCGA CGCTGTTGCG AGTGGCCTTC CCCGACAAGG CCTGGGCCGA CGCCGAGCAA    12360
CTGTTCAGTG TGAAGACGCT GACGTTTCTC GGCTTTATCG GCGTGCTGTT GGCCATCAAC    12420
CTCTTCGGCA ACCGGGCGAT CAAGTGGGCC AACGAACGT CAACGGTAGG CAAGGCATTC     12480
```

FIGURE 2-17

```
GCGCTCTCGG CATTCATTGT CGGCGGGCTG TGGATCATCA CCACCCAGCA CGTGAACAAC    12540
TACGCAACGG CGTGGTCGGC ATACAGCGCG ACCCCGTACT CGTTGCTTGG CGTCGCCGAA    12600
ATTGGCAAGG GCACGTTCTC GAGTATGGCG CTGGCCACGA TTGTCGCGTT GTACGCATTC    12660
ACCGGTTTCG AATCGATCGC GAACGCCGCC GAAGAAATGG ACGCGCCGGA CCGGAACCTG    12720
CCGAGAGCTA TACCGATCGC GATCTTCTCG GTTGGCGCGA TCTACTTGCT CACCCTAACG    12780
GTAGCGGATGC TGCTCGGATC GAACAAGATC GCCGGTCGG GCGACACCGT GAAACTGGCC    12840
GCGGCCATCG GAAACGCTAC CTTCCGAACG ATCATCGTCG TCGGAGCCCT GATATCGATG    12900
TTCGGCATCA ATGTCGCGGC CTCGTTCGGT GCACCGCGGC TTTGGACCGC GTTAGCGGAC    12960
AGCGGGGTTC TGCCGACACG CTTGTCACGC AAGAACCAAT ACGACGTGCC GATGGTCTCC    13020
TTCGCAATTA CGGCGTCGTT GGGCTCGCA TTCCCGTTGG CGCTGCGGTT CGACAACCTG    13080
CACCTGACCG GCCTGGCGGT GATCGCCCGA TTCGTCCAGT TCATCATCGT GCCGATCGCT    13140
CTCATCGCAT TGGCGAGGTC TCAGGCAGTA GAACATGCTG CTGTGCGGCG AAATGCGTTC    13200
ACCGACAAGG TGTTACCGCT TGTTGCGATC GTGGTCTCGG TTGGGCTGGC AGTGTCCTAC    13260
```

FIGURE 2-18

```
GACTACCGCT GCATCTTTCT AGTGCGGGGT GGTCCGAACT ACTTCTCGAT TGCTTTGATC    13320
GTGATCACGT TCATCGTGGT ACCGGCGATG GCTTATCTGC ACTACTACCG AATCATTCGC    13380
CGGGTTGGCG ATCGGCCGAG CACTCGCTAG ATTCCGTTGG CGCTGAGCTC GAACGGGAGA    13440
ACACAACGGC GAGCGGATGG GGGAATAGCC TGGTCGGTGC GGGCAAGATT TCAACCTGCA    13500
TTCCCGGATC GGCGGCGCGG GCAAGCGTCT GCAACGCCGA GGGACTGTAG GCACGTAGTG    13560
CGCTGATAAA GCCGTCGTGC ATGCTCGAGC GCATCGACGA CCATGGCAGC AGCAGTAGGT    13620
GGAGCGGCAG TAGCAGCACC GAAGAGAGCG TGAACGACAG CGGTTTCTGC CGTTTGAGGT    13680
CGATGATCAG AAAGCGCTTC CCCACCCGGG TGGCCTCGGC GATCGCTTTG CAGGCGACCG    13740
TAGGCGGCAG GTGGTGAAAT GCCAGCGGCGA AGACCGCCAG GTCATAGCTG TGGTCGTGGC    13800
CGTCGATTGC GGTGGCGTCG ATCACTTGGG TGCCGTGCTCG CGGATGTGTT CCCAGCTCTC    13860
CCGCGGCGAT GTTGGCCACC GAGGTGGGAT CTAGATCGCT GATCGTCACC GTCGCTGTCG    13920
GGTGTAGCTC GAGGATTTTC GCTGAGAGCT TGCCATGGCC CGCACCAAGT TCCAGGATTC    13980
GCGGGTTGGG AATGTCAGAA ACAAGTTTCA GGGCTATCCG GGCGTACTTC TCGTGCAGGT    14040
```

FIGURE 2-19

```
TGGTCAGGGT GCCCACCCGG TCGAGCACCC CGATGATCTT CTGTTTGACC TCATCGGGCA    14100
CATCGTGCGG GTCGAGGTAC TCCAGTGCGT CGGTCTGGAA TCGACGATCC AGCCAAGACG    14160
CGTCGGGGCC ACCCCGTGGC ATCGTGGCGA TCGCCCTGCTC GCGGATGTTC GCCTCACCCA    14220
TGGCAGCTCT TCCCCTCTCG ACGTCCCGTG TTCGCAATGC TATGAGACCG CTGACCGGGC    14280
TCCCCAGCCC GCCGGTCGCG CGTGCTTAGC TACGTAGCAG AGGGGCCGTC ACTTCGAGGG    14340
CTGCCGCCAC TCGGTGATCT TGCGGCCCAA TGAATCGGCC GCGTTCGAGG CTGCCCGTCC    14400
CACGGCTTTG GTTCACGGTG AAGATCGCAC AGCCGGTGCC GGAAAAGTCC GCGGCACCGA    14460
TGTCGGTCAG CAAGACGTTG AAGAGAAACC CCGAGATCAC CGCCCATGGG ATCGTCATCA    14520
ACACCCCAGG CAGCGTCGAC ACCCGGCCA CGAACCAGCA CTGAAGTAGG TATTCACGCC    14580
ACGCGAAAGG CGGCTTGAAC ATGCACACGG ACGTGTCGAG CGTCATCGCG AAGAAATCGC    14640
CCAGCGCGCC CACCGGCCGC AAGACCGGAT CAGGCACCCG ACCGGCCGCC TTGTCGGCCA    14700
CGATTACCAT GGCGGGCGC TTCGATGCTG GGCCGTTGGG TGAGGTGGCG    14760
CACGCTGGCC CCCCGGACAG GTCGACGATC GGTGACATTG GTGAGCGTAC GCGGCAGAGA    14820
```

FIGURE 2-20

```
CCGCTGATGT CCATAGCCAA TACGCGATTG CTTGGACAAC TGATCGGTAA ATAGCAATGC    14880
AAACTGGCAT ATATTGGCTA TGATGTATCT TGCTAGTATC CTATAGCGCG GGGCGATGTG    14940
CTCTGCTGCC TTGGCGGGCCG ACAGGCGCAT CACCGGTCAA GCCGTTGGCT CGAGTCACGC    15000
TGGCGAGGCA CCACGATCAG GCATCAACAG CGCGCCCGAC GGGCGGTGAT CGGATGCCGC    15060
ATCCTGACCG CCTCGATTCG GGCCCGCCGA CCAGAGCCTT CGGCGACCGGC GAGGTTGCCA    15120
CCATGGTCGT CGAAGCAACT TGCTGCTAAC GAGCCTGTAG TTTTGCCAGC CCCCACTCGC    15180
GCTTTGTCTG CAGGTTTTCA CGGCTCAGCGA CGGCTCATGT CGTTGCGCAC GGCGAATTC    15239
```

FIGURE 3-1

```
GAATTCACTT AGCTAACACC AGTTCTAGCA GCTGTCGGCG CGACTTCTTG TCAGTGCCCG   60
ACGTTATGAT TCGAACATGT TAGCGAATAG CCGGGAGGAG CTTGTCGAGG TCTTTGATGC  120
GCTGGATGCC GAGCTGGACC GCTTGGACGA GGTGTCTTTT GAGGTGTTGA CCACCCCGGA  180
ACGGCTGCGG TCTCTGGAAC GTCTGGAATG CTTGGTGCGC CGGCTACCGG CGGTCGGGCA  240
CACGTTGATC AACCAACTCG ACACCCAAGC CAGGCGAGGAA GAACTGGGCG GCACGCTGTG  300
CTGCGCGCTG CCAACCGGT CTCGGACCTC GTCCGAGCAC CAAGCCCGAC GCCGCCCTAC GCATCGCCGA  360
CGCCGCCGAT CTCACCGCCG CCACCGCCCA ACGCCAGGGC CTGATCGGCG ACCGCTAGCC CCACAGTTTG  420
ACCGCCACCG CCACCGCCCA ACGCCAGGGC CTGATCGGCG AAGGCGCACA TCAAAGTGAT  480
TCGCGCCCTT TTTCGGCCCA ACCTGCCCGC CGGGGTGGAT GTGTCCAAAC CCGCCAGGCC  540
GCCGAAGCCC GACCTGGCCG CAAACCGCTC AAATATCGTC CCGACGAGCT GGCCGCTAC  600
GCCCAGGGGG TCATGGACTG GCTACACCCC GACGGCGACC TCACCGACAC CGAACGCGCC  660
CGCAAACGCG GCATCACCCT GAGCAACCAG CAATACGACG GCATGTCACG GCTAAGTGGC  720
TACCTGACCC CCCAAGCGCG GGCCACCTTT GAAGCCGTGC TAGCCAAACT GGCCGCCCCC  780
```

FIGURE 3-2

```
GGCGCGACCA ACCCCGACGA CCACACCCCG GTCATGGACA CCACCCCCGA TGCGGCCGCC   840
ATCGACCGCG ACACCCGCAG CCAAGCCCAA CGCAACCACG ACGGGCTGCT GGCCGGGCTG   900
CGCGCGCTGA TCGCCTCCGG GGAACTGGGC CAACACAACG GTCTTCCCGT CTCGATCGTG   960
GTCACCACCA CCCTGACCGA CCTGCAAACC GGCGCGGGCA AGGGCTTCAC CGGCGGCGGC  1020
ACCCTGCTAC CCATGGCCGA TGTGATCCGC ATGACCAGCC ACGCCCACCA CTACTCCCCC  1080
GCAAGCGGGA GGTACCCCCA GGCGATCTTC GACCACGGCA CACCCCTGGC GCTGTATCAC  1140
ACCAAACGCC TAGCCTCCCC GGCCCAGCGG ATCATGCTGT TCGCCAACGA CCGCGGCTGC  1200
ACCAAACCCG GCTGTGACGC ACCGGCCTAC CACAGCCAAG CCCACCACGT CACCGGCTGG  1260
ACCAGCACCG GACGCACCGA CATCACCGAC CTCACCCTGG CCTGCGACCC CGACAACCGA  1320
CTCGCCGAAA AAGGCTGGAC CACCCGCAAA AACACCCACG GCCACACCGA ATGGCTACCA  1380
CCACCCCACC TCGACCACGG CCAACCGTGG ACCTGTGAGA TACACTACAC CTGTGCGTGC  1440
TGCTGTCTAC CTCCGAATCT CAGAAGACCG CTCGGGCGAA CAGCTCGGGG TGGCCCGCCA  1500
ACGGGAGGAC TGCCTAAAGC TGTGCGGGCA GCGAAAATGG GTGCCCGTCG AGTACCTCGA  1560
```

FIGURE 3-3

```
CAACGACGTC AGCGCATCAA CCGGCAAGCG CCGCCCCGCC TACGAGCAGA TGTTGGCCGA   1620
CATCACCGCC GGCAAGATCG CCGCCCGTGGT GGCCTGGGAC CTGGACCGGC TCCATCGCCG   1680
TCCCATCGAG CTGGAAGCCT TCATGTCATT AGCCGACGAG AAGCGGCTGG CCCTGGCCAC   1740
CGTCGCCGGC GACGTTGACC TGGCGACACC CCAGGGCCGG CTAGTCGCCC GCCTGAAGGG   1800
GTCGGTGGCC GCTCACGAAA CCGAGCACAA GAAGGCACGA CAGCGCCGCG CCGCCCCGCCA   1860
GAAAGCTGAA CGGGCCACC CCAACTGGTC GAAAGCCTTC GGCTACCTGC CGGCCCCAA   1920
CGGTCCCGAA CCCGACCCCC GGACAGCGCC GCTGGTCAAA CAGGCCTACG CCGACATCCT   1980
CGCCGGGGCG TCCCTGGGCG ACGTGTGCCG CCAGTGGAAC GACGCCGGGG CGTTCACCAT   2040
CACCGGCCGC CCGTGGACGA CTACAACGCT GTGCCCGCTA CGGCCCGGTG GACCGGCGACG CCCGCAACGC   2100
CGGACTACGC GCATATAAGG TGGTCGCCGC TGGTGGACGA GGCGACGTTC TGGGCCGCCC AGGCCGTGCT   2160
CAAGGCCCAG TGGTCGCCGC GGCCGCGCCC AAGCGTGCGC CGCCACCTGC TGACCGGGCT   2220
GGACGCCCCC GGCCGCGCCC CCGGCCCGCAA AAGCGTGCGC CGCCACCTGC TGACCGGGCT   2280
GGCAGGCTGC GGCAAATGCG GCAACCACCT GCCGGGCAGC TACCGCACCG ACGGCCAGGT   2340
```

FIGURE 3-4

```
CGTCTACGTG TGCAAGGCGT GCCACGGGGT GGCCATCCTG GCCGACAACA TCGAACCGAT    2400
CCTGTATCAC ATCGTGGCCG AGCGGCTGGC CATGCCCGAC GCCGTTGACT TGTTGCGCCG    2460
GGAGATTCAC GACGCCGCCG AAGCCGAAAC CATCCGCCTG GAACTGGAAA CCCTCTACGG    2520
GAGCTGGACA GGCTCGCCGT CGAACGCGCC GAAGGGCTAC TGACCGGCG CCAGGTGAAG    2580
ATCAGCACCG ACATCGTCAA CGCCAAGATA ACGAAACTTC AGGCCCGCCA ACAGGATCAG    2640
GAACGGCTCC GAGTGTTCGA CGGGATACCG TTGGGAACAC CGCAAGTCGC CGGGATGATA    2700
GCCGAGCTGT CGCCGGACCG GTTCCGCGCC GTCCTCGACG TCCTCGCTGA AGTCGTTGTC    2760
CAGCCGGTCG GCAAGAGCGG CAGGATATTC AATCCCGAAC GGGTGCAGGT GAATTGGCGA    2820
TGAGCCGGCA CCACAACATC GTGATCGTCT GTGACCACGG CCGCAAAGGC GATGCCCGCA    2880
TCGAACACGA GCGCTGCCAT CTTGTCGCGC CGATCATTTG GGTCGACGAG ACCCAGGGCT    2940
GGTTACCGCA GGCGCCAGCG GTGGCAACAT TACTCGACGA CGACAACCAG CCGCGAGCCG    3000
TTATTGGCTT GCCGCCCAAC GAGTCTCGCC TACGACCTGA AATGCGCCGC GACGGGTGGG    3060
TGCGGCTGCA CTGGGAATTC GCCTGCCTGA GGTACGGCGC CGCCGGCGTG CGCACGTGCG    3120
```

FIGURE 3-5

```
AGCAGCGGCC CGTGCGGGTT CGCAACGGCG ACCTGCAAAC ACTGTGCGAG AACGTTCCGC   3180
GGCTACTGAC CGGACTGGCC GGCAACCCCG ACTACGCACC GGGTTTTGCG GTGCAGTCGG   3240
ACGCGGTGGT CGTCGCCATG TGGCTGTGGC GCACGCTCTG CGAAAGCGAC ACGCCGAACA   3300
AACTACGCGC CACCCCAACG CGTGGTAGCT GCTAGACTCC GACGTAGCCG GCTTCGACTC   3360
CGGGGTTTTG GTGTCCCCAA GGAGTCGCAC GTGTCGACCA TCTACCATCA TCGCGGCCGC   3420
GTAGCCGCAC TGTCTCGTTC CCGCGCATCC GACGATCCCG AGTTCATCGC CGGAAAACC   3480
GATCTCGTTG CCGCGAACAT CGGCGACTAC CTCATCCGCA CCCTCGCCGC AGCGCCCCC   3540
CTGACTGACG AGCAGCGCAC CCGGCTGGCC GAGCTGCTGC GCCGCCCGCG GCGGTCAGGC   3600
GGTGCCCGAT GACCGCCGGC GCCGGCGGGT CGCCGCCGAC TCGGCCACGG   3660
AGGACCGGGC ACCCGGCGACA GTCGCCACAC CGTCTAGCGC CGATCCTACC GCGTCACGCG   3720
CCGTGTCGTG GTGGTCGGTG CACGAGCATG TCGCGCCGGT CCTGGATGCT GCCGGGTCGT   3780
GGCCGATGGC CGGCACACCG GCCTGGCGTC AGCTCGACGA CGCCGATCCT CGCAAATGGG   3840
CCGCGATCTG CGACGCAGCC CGGCACTGGG CTCTGAGGGT AGAGACGTGC CAGGAGGCGA   3900
```

FIGURE 3-6

```
TGGGCGCAGGC GTCACGTGAC GTATCTGCGG CCGCCGACTG GCCCGGCATC GCCCGCGAGA    3960
TCGTCCGACG GCGGGGCGTG TACATCCCGC GGGCGGGGGT GGCGTGATGG CCGACATCCC    4020
CTACGGCACC GACTATCCCG ACGCCCCCTG GATCGACCGG GACGGGCACG TGCTCATCGA    4080
CGACGGTGGC AAACCGACGC AAGTTCATCG CGGCCAAGCC CGAATCGCCT ACCGGCTAGC    4140
CGAACGTTAC CAGGACAAGC TGCTGCACGT AGCCAAACGT GGCTGGCACT CCTGGGACGG    4200
CAGACGCTGG GCAGCCGACG ACCGGCGGGA AGCCAAACGT GCAGTGCTGG CAGAGCTGCG    4260
CCAAGCGCTC TCAGACAGCC TCAACGACAA GGAATTACGC GCCGACGTCC GAAAATGCGA    4320
ATCGGCGTCC GGCGTGGCCG GCGTGCTCGA CCTGCCCGCC GCACTGGTAC CATTCGCCGC    4380
GACGCTAGCC GACCTCGACA GCGACCCGCA CTTGCTCAAC GTCGGAATG GGACGCTGGA    4440
CCTGCACACG CTCAAATTGC GGCCCACGC GCCCGCTGAC CGCATCACAA AGATATGCCG    4500
CGGTGCCTAC CAGTCCGACA CCGAATCGCC TCTCTGGCAA GGTTCTTGA CCCGCGTTCT    4560
GCCCGATGAA GGTGTGCGCG GGTTCGTGCA ACGCCTGGCC GGGTCGCGCC TACTAGGCAC    4620
CGTCCGCGAA CATGTCCTGG CGATTCTTAT CGGTGTAGGT GCCAACGAA AATCTGTGTT    4680
```

FIGURE 3-7

```
CGACAAGGCG ATTCGCTATG CCCTTGGCGA TTATGCCTGC ACCGCTGAGC CTGACCTTTT    4740
CATGCACCGG GAAAACGCTC ACCCAACAGG CGAAATGGAC CTCCGGGGCG TGCGATGGGT    4800
AGCGGTATCC GAGAGCGAAA AAGATCGCCG GCTGGCCGAA TCAACGATAA AACGGCTGAC    4860
TGGCGGCGAC GCCATCCGCG CCCGAAAGAT GCGGCAAGAC TTCGTGGAAT TCGAGTGGTG    4920
CCGTTTGAAG TAGTGATTCC TGCCGACGAG CAGGACCGGG AACTGGACGC ACGGTTGCAG    4980
TTGGAGGCCG ACAGCATCCT GTCCTGGGCG GTGGCCTCGC GCAACGTCGA ATTACCGCGA    5040
GGACTATCCC AGCCCGGACGC GGTGCTCGCG GCAACGTCGA ATTACCGCGA GGACTCCGAC    5100
ACGATAAAGA GGTTCATCGA CGACGAATGC GTCACCAGCT CGCCGGTGCT GAAAGCCACT    5160
ACTACGCATC TGTTCGAGGC GTGGCAAAGG TGGCGGGTGC AAGAAGGCGT ACCCGAAATC    5220
TCGCGCAAAG CGTTCGGCCA GTCGCTCGAC ACCCACGGAT ACCCGGTCAC TGACAAGGCC    5280
CGTGATGGTC GTTGGGCGGC CGGAATAGCG GTGAGAGGGG CCGATGATTT CGATGATTAG    5340
CACACCTAAC GTGACGCATG TGACGCATT CCAGGTTCGC CTACGCGCGC GCACGTATGG    5400
CGGTTATACC GCGCAAACGT CACATGCGTC ACGGCCTGCC GTGCCGTTCT GCCCAGGATG    5460
```

FIGURE 3-8

```
CGGTACCTAC CTGGCCGTTC ACGGCCGCCA CCGGGCGGAC TGTACCGCCA AACCAGCAAA   5520
CACCGGGCGT GCCGCATGAC CGCTGTCGCG ATCACCCCGG CATCCGGCGG TCGGCACAGC   5580
GTCCGATTCG CCTACGACTC TGCGATCGTG TCGTTGATCA AGTCCTCGAT CCCCGCCTAT   5640
GCCCGCTCCT GGTCCGGCGA CACCCGCTGC TGGTTCATCG ACGCTGACTG GACCCCACTG   5700
CTGGCCGCCG AGCTGCGCTA CCACGGCCAC ACCGTCACCG GACCCGCCGA CCCGGCGCAA   5760
CAGCAGTGCA CCGACTGGGC CAAAGCGGTTG TTCCGGGCGG TCGGACCCCA GCGGACACCC   5820
GCCGTGTACA GGGCTTTATC CAAAGTGCTG CACCCCGACG CCCCAACCGG ATGCCCGATA   5880
CTGCAACAGC AGCTCAAATGC CGCCAGAACC GCACTTACCA ACCCTGCTTG AAAGGACACA   5940
AGCCATGGCT GAAACCCCCG ACCACGCCGA ACTGCGGGCA CGAATCGCCG ACATGGCTTT   6000
CAACGCCGAT GTCGGTATGG CGACCTGCAA ACGCTGTGGT GACGCCGTGC CGTACATCAT   6060
CCTGCCGAAC CTGCAGACCG GCGAACCCGT CATGGGTGTC GCCGACAACA AATGGAAGCG   6120
CGCGAACTGT CCCGTCGACG TCGGTAAGCC GTGCCCGTTC CTAATCGCCG AGGGTGTCGC   6180
CGACAGTACC GACGACACCA TAGAGGTCGA CCAGTGACCC CGATCAACCG GCCCCTGACC   6240
```

FIGURE 3-9

```
AACGACGAAC GACAACTGAT GCACGAGCTG GCAGTCCAGG TTGTCTGCTC GCAGACGGGT   6300
TGCTCACCCG ATGCGGCGGT CGAAGCACTC GAATCCTTCG CGAAAGACGG AACACTTATC   6360
CTCCGGGCG ACACCGAGAA CGCCTACCTC GAAGCCGGAG GCAATGTTCT TGTCCATGCC    6420
GATCGTGACT GGCTTGCCTT CCACGCGTCG TATCCCGGCA ACGACCCGCT GCGAGACGCC   6480
CGACCTATCG AGCAGGACGA CGACCAGGGG GCGCGCATGC ACGCTCATTA CCTAGACTAA AGGCCCAGCC   6540
CGGACACCGC CACGGTGCCG GCGCGCATGC ACGCTCATTA CCTAGACTAA AAATTGATGG   6600
GAGGACCGAT GCCAAGACCA CCCGGCTCAA ACTGGTTGAG GCCGCTCCC              6660
CCGGCCGCGA TTCCGGGCGC CGGAAAGTCC CCGAGTCGCC GAAGTTTATC CGTCAGGCAC   6720
CGGATGCCCC GGACTGGCTC GACGCCGAGG CGCTGGCCGA ATGGGGCGC GTCGCACCGA    6780
CTTTGGAGCG GCTTGACCTG CTCAAACCTG AGGATCGGGC GCTCCTGTCC GCTACTGCG    6840
AGACCTGGTC CGTCTACGTC GCGGCGGGTTC AGCGGGTCCG CGCCGAAGGC CTCACAATTA  6900
CCTCACCGAA ATCCGGTGTC GTGCACCGGA ACCGGCGGT GACGGTTGCG GAGACGGCGC   6960
GCATGCATCT GCTGCGCTTG GCCTCCGAGT TTGGCCTGAC CCCGGCCGCC GAGCAGCGAC   7020
```

FIGURE 3-10

```
TGGCGGTGGC GCCGGGCGAC GACGGGCGAC GGCTCAACCC GTTTGCCCCG GACCGGTGAT    7080
GACCTTTTGT GTGTGATACA ATCGAGTTTG GCATCTCGGC ATCCGCTGAC GCCGGGCAGT    7140
CGCCGCGGGG CGGCTGGAAC CCGGATAGCG GCCGCCATGC GCCACAAGCG ATTCCGCGCG    7200
TTTCTTGCGT CTGCTAGGTG GTGGCCGAAT TTGAGTAGC ATCCTTTTCC GCATGGCCGA     7260
GCTGCGGTCT GGCGAAGGCC GAACCGTGCA CGGCACCATC GTGCCCTACA ACGAGGCGAC    7320
CACCGTCCGC GACTTCGACG GCGAGTTCCA GGAAATGTTC GCTCCTGGCG CTTTTCGGCG    7380
CTCCATCGCC GAGCGCGGCC ACAAATTGAA GCTGCTGGTC TCTCACGACG CTCGAACCCG    7440
CTACCCGGTG GGCCGGGCCG TTGAGTTGCG GGAGGAGCCT CACGGCTTGT TCGGGGCGTT    7500
CGAGATTGCG GACACCCCGG ACGGCGACGA GGCTTTGGCG AACGTAAAAG CTGGTGTCGT    7560
CGACTCGTTT TCGGTGGGTT TCCGACCGAT CCGGGACCGT CGCGAAGGGG ATGTGCTGGT    7620
GCGGTCGAA GCGGCGCTGT TAGAGGTTTC CCTAACCGGC GTTCCGGCCT ATTCGGGGGC     7680
ACAAATCGCC GGGGTGCGCG CGGAATCGCT TACAGTCGTT TCCCGTTCGA CAGCCGAAGC    7740
CTGGCTGTCC CTACTCGATT GGTGAACAAT CTATGACCGA ATTCGACGAC ATCAAAAACC    7800
```

FIGURE 3-11

| | | | | | |
|---|---|---|---|---|---|
| TCTCTTTACC | TGAAACCCGT | GACGCGGCGA | AGCAGCTCCT | CGACAGTGTC | GCCGTGTGAC | 7860
| CTGACCGGTG | AGGCGGGGCA | GCGTTATTCA | GGCGCTGACG | CGCCACGCCG | AGGAACTGCG | 7920
| GGCGGAGCAG | CGCCGCCGCG | GCCGCGAAGC | CGAGGAGGAG | CTGCGCCGCT | ACCGGGCCGG | 7980
| TGAGCTGAGG | GTGGTGCCCG | GCGCTCCCAC | CGGCGGCGAC | GACGGGCGAC | CGCCGCCGGG | 8040
| CAACTCGTTG | CGGGACACCG | CGTTTCGCAC | ACTGGATTCT | TGTGTGCGAG | ACGGCCTGAT | 8100
| GTCGTCGCGG | GCGGGGAGA | CCGGCGAAAC | CTTGTGCCGC | ACCGGGCCGC | CGCAGTCCAC | 8160
| CTCGTGGGCG | CAGCGCTGGC | TGGCGGCCAC | CGGCAGCCCG | GACTATTTGG | GCGCGTTCGT | 8220
| CAAGCGGGTT | TCCAATCCTG | TTGCGGGGCA | CACGGTTTGG | ACCGACCGGG | AAGCGGCCGC | 8280
| GTGGCGTGAG | GCTGCCGCCG | TGGCCGCCGG | GCAGCGAGCG | ATGGGCCTGG | TGGACACCCA | 8340
| AGGCGGGTT | CTGATCCCGG | CGGCGCTGGA | CCCGGGCGATC | CTGCTGTCGG | GTGATGGGTC | 8400
| GACGAACCCG | ATTCGGCAGG | TGGCGAGGGT | GGTGCAAACG | ACCTCCGAGA | TTTGGCGGGG | 8460
| CGTGACTTCC | GAAGGCGCCG | AAGCTCGTTG | GTACTCCGAA | GCCAGGAGG | TGTCCGACGA | 8520
| TTCGCCAGCG | CGGCCCAGC | CGGCGGTGCC | CGGCGTGCC | AACTACCGT | GGAAGCTGCT | GGATTCCGTT | 8580

FIGURE 3-12

```
CTCCATCGAG CTGGAGGGTG ACGGGCGAG CTTCGTTGGC GAGATCGGCA AGATTCTCGC   8640
GGACAGCGTT GAGCAACTGC AGACCGCGGC GTTCGTCAAC GGCTCCGGCA ACGGCGAGCC   8700
CACCGGGTTC GTCAGCGCGC TAACCGGCAC CTCCGATCAG GTGGTCGTCG GCGCGGGGTC   8760
AGAAGCGATT GTGGCGGGCG ATGTTTACGC GTTGCAGTCG GCGCTGCCGC CAAGGTTCCA   8820
GGCCAGCGCC GCGTTCGCGG CGAACTTGTC CACCATCAAC ACGTTGCGGC AGGCGGAAAC   8880
TTCGAATGGC GCGCTGAAAT TCCCATCGCT GCACGACAGT CCGCCGATGC TAGCCGGGAA   8940
GTCTGTCCTG GAAGTCTCCC ACATGACAC CGTTGATTCG GCGGTGACAG CGACGAATCA   9000
TCCACTGGTG CTTGGCGACT GGAAGCAATT CCTCATCGTC GACAGAGTTG GGTCCATGGT   9060
GGAGTTGGTG CCTCACCTGT TCGGGCCGAA TCGCCGGCCG ACCGGGCAGC GCGGATTCTT   9120
CGCCTGGTTC AGGGTCGGAT CAGATGTGCT GGTGCGCAAC GCGTTTCGAG TTCTGAAGGT   9180
GGAGACTACC GCGTAGGTAG GATAGGGCCA GGCGTGGGCG GCCTCTGCTT AGGGGTGCCG   9240
GGCCGGCCAC GCCCGCCAAC TCCCCTGCGG GTTGCGTTGT CGATTCGTNN NNNNNNNNNN   9300
NNNNNNNNNN NNNNNNNNNN NNNNNNNNNN NNNNNNNNNN NNNNNNNNNN NNNNNNNNNN   9360
```

FIGURE 3-13

```
NNNNNNNNNN NNNNNNNNNN NNNNNNNNNN NNNNNNNNNN NNNNNNNNNN NNNNNNNNNN     9420
NNNNNNNNNN NNNNNNNNNN NNNNNNNNNN NNNNNNNNNN NNNNNNNNNN NNNNNNNNNN     9480
NNNNNNNNCC AAGCCAGAAT ATCGAGCCTG GCGGCCATGG TCGCCGCCTT CCTGTGCCG      9540
CTGCTTGGCT TTCGCCGGTT CCAGCTCGGC GATCCGGCGG CCAGCGGCGC CATTTGTTTC     9600
TCCGCGAACA GGCGGATTTC TTTGTCGTCG CTGCGGGTTG CGTTGTCGAT TCGTTTGAGC     9660
CGCTTGTAGG TGCCGGGCGA GATGCCGAGG GCTGCGCCTA CCTCCTTGTC AGTGTGGCGC     9720
TGAGACGGCT TTGGTTCCAT GGGACCAAAG CCGGCATTGG TGATCGATGC ACCGAGGCGA     9780
CCACCCTCGC GTTGGCGCTC CTTGGCTTTC GGGCGTTCCA GCTCGGCGAT CCGGGCGACCA    9840
GCGGCGCCAT TTGTTTCTCC GCGAACCGGC GGATTTCTTT GTCGTCGCTG TGGGTTGCGT     9900
TGTCGATTCG TTTGAGCCGC CGGTAGGTGC CGGCGGAGAT GCCGAGGGCT GCGCCGATAG     9960
CAGTGTCTGT TTTCGTCGAA TGACGCTCTG ATTCTGGTTT GCCCCTCGCG GGCCCCAAAC    10020
CAGAATATCG AGCCTGGCGG CCATGATCCT GCCCCTCGCG CTGCCGCTGC TTGGCTTTCG    10080
GCCGCTCCAG CTCCGCGATC CGGCGGCCAG CGGCGCCATT TGTTCTCCG  AGATAGCTTC    10140
```

FIGURE 3-14

```
CGGCCCATGG GCCGGAAGCT ATCCATGCCC CGCCCGTGGG ACCGCCCAGC GTCCTGTTGC    10200
CGCGGTGTTC ACCGTCAGCG CTCGTCTTCC GCTGGGCTTC CGCCGCCAAG CCCGATCATC    10260
CGGCTCCACG GCGGGGTGTC GTCGCCGTCG GGCTCGTCGT CGCCGGCGAG TCCGAGTTGC    10320
CGGTTGATGG CGGCTTGTTC CGGCCCGGAG CGGCCCGGCCA GGATCGCCGG GCCGCACTCG   10380
TCGCCGCCGG CGGCGTCGGC GTGCTCGACG CTGATCCGCA GGAACGCTTC GAGCTCGCCG    10440
GTGTGCTCGT GCCGATTCAA CGGGCCTGC AGCCGAACGA GCGCTTCCCT CACCTCCAAG     10500
GGCGGGTCCG GGAACCACGC CCGGATCGTC TCGGCCACCT GGTCGCGGTC GCAGACGGCG    10560
CGGTCACCGG TTTCCAGGTC GGTTACCGTC ACCAAGTGGT TGAAACGTGC TGGTGTGGTG    10620
GTCATGGTTG ATCTCCTGGC GTGGAATGTT CTTCAGCAGT CCACGGCCAA CCCCGCACCA    10680
ACACCTTCCA CCACCACGAG AAGCTGCTAC GCCACAACGA CGAGGACAAC CACGACGATC    10740
CGTGAGAATC GCCGCCCGCG AAGATCTTTG GACATCCCCA CATCGACGTG CGTCCTCGCC    10800
ACCTGGCCAG CACCCGCCCG AACCCGGGAG CTGGCCATTA AGACGAAGTT GCGATCAAAC    10860
CCCTTCGCCA TCAAGCTTTT TGGGCCCGCC TCACCCCAGC AGGTACTCGG CACGGCGTGTT  10920
```

FIGURE 3-15

| | | | | | |
|---|---|---|---|---|---|
| GCCGTCCCAG | CGGCGCAAGC | CGGCGAACCG | ACCGTCAATC | CGGCGACGGCC | GTCCCGCAAT | 10980 |
| GCGCAGCGCC | CGCCCAATT | GGTGACCACC | GACCCGTCGG | GCCAGGGTGA | CATGGGCGGT | 11040 |
| CCACTGACCG | GGCAGGCTGT | TGGCCATCGG | CGCGGGGCGCC | AGGTGCGGGC | CGCAGAGCCG | 11100 |
| GTGCACCTCG | GCATGCAGGG | CCAAAAGCTC | GCTGGTCGGC | ACCACCAGCC | GGGTGAACAC | 11160 |
| GACATTGGCC | CGCCCGAACA | GCACCGGCGC | GCCGATCACG | CAGTCCAGCG | GCAGCCGACG | 11220 |
| GGCAACCGCA | CCCAGCGGCT | CATCGACCTC | CGGGGGCGATC | CGTTCGGCCA | CCGCCAGCGA | 11280 |
| CACGTGCGGA | CGGCTGGCCG | GCGCCTGGCT | GGGTATGCCG | GCGGGGCCA | ACCCCGCCCA | 11340 |
| GATGCGCCGG | ATCGCCGCCT | CGGTATCGCT | GTCGAAGACC | AGCTCGATCG | AATGCACCAT | 11400 |
| CAGCCGACCA | GCCCCGGCAAC | CCAGTTGCGG | TCGAACGCCG | CCGGCTCAT | CGCCGGCGAAG | 11460 |
| TCCCCGGCAT | CCAGCGACGC | GGCCCCGGCG | GGCAGAGCGG | CCCGCACCGT | AGCAATGCGC | 11520 |
| GCCAGCGCGG | ACCGATTCGA | GGCTGCCACC | AACCCGGGCG | GGTCCGGCCA | GCTGCCGATC | 11580 |
| ACCAGCCCTG | CACATGAAAC | CTGTTGTGCA | GCAAGCGCTT | CCAACGTCAA | CTTGGTGTGG | 11640 |
| TTGAGGGTGC | CCAGGTCCGC | GGTGACCACC | ACCAAAGCCG | CGGCGGCCAC | GTCGACGGCG | 11700 |

FIGURE 3-16

```
ACATCGCGCA GCGTGACGCC CGGCTCGGCG AGTTCGACCA GCAGCCCGCC CGCCCCCTCG   11760
ACGAGGGTCA ACCGCCCGGG ACGGTCCAGG TCTGCGATCA GCCGCACGAT CTGATCGCGG   11820
GCGGGCAACG CCATCCCGGC GTGTTCGGCG GGGCGGGCCG GGGCCATCGG CTGCGGATAT   11880
CGGCCAAGC CGGCCAGCTG GGTCACCCCG GCCAACCGGC CGACCTCGGC GAGGTCGTCG    11940
TCACCGCGGG CGGTGCCGGT CTGAACGGGC TTGCACACCG CCACGTCGAT GCCGGCCTGA   12000
CGTGCGGGCCG ACGCCAGCGC CGGCGAGACG ACCGTCTTGC CGACCCCCGT GCCGGTCCCG  12060
GTGACGACCA GGATCGTCAA CGGGCGGCCA CGGCGAGAAC ATCCGTCAGC ACCCGCCGGG   12120
CCAGCTCGAG CTCGCCGGCG TTCAGCGATG CGGCGCGGT CAGCCGCAGC CGCGACGTAC    12180
CCGCGGGCAC CGTCGGCGGC CGGAAGCAGC CCACCTTGAC CCCGGCGTCC AGGCAGGCCG   12240
CCGCGGGCGGC CACTGCCGAC TCCGGCTCGC CCAGGATCAC CCAGGATCAC GCCGAGTCCG  12300
GCACCGCAGC CACACCGCAC ATCCGGCAA GTTCACCAGC GTGGTTGAGC ACCGCCTGCG    12360
ATCGCCACGG CTCGGCCTGC AAGACGCGCA GCGGCCCG TGCGGCACCT TC             12412
```

VIRULENCE-ATTENUATING GENETIC DELETIONS DELETED FROM MYCOBACTERIUM BCG

BACKGROUND OF THE INVENTION

*Mycobacterium tuberculosis* (MTB) infects over ten million people each year and kills over three million, making it the infectious agent causing the greatest mortality worldwide. In an effort to combat *Mycobacterium tuberculosis*, vaccination programs using a viable attenuated strain of *Mycobacterium bovis* called bacille Calmette-Guérin (BCG) have been established in more than 120 countries over the course of the last 5 decades. Although widely used and considered safe enough to administer to infants, the BCG vaccine is controversial for two principle reasons: 1) Efficacy for BCG vaccines against tuberculosis has varied from 0–85% in different clinical trials; and 2) Immunization with BCG sensitizes vaccinees to the tubercular antigens used in the tuberculin skin test, confounding attempts to discriminate between BCG immunization and TB infection. For these two reasons, especially the latter, BCG is not used in the United States where surveillance with the tuberculin test is preferred.

The original Pasteur BCG strain was developed by multiple (230 times) serial passages in liquid culture. BCG has never been shown to revert to virulence in animals indicating that the attenuating mutations in BCG are stable deletions and/or multiple mutations which cannot revert. However, the mutations which arose during serial passage of the original BCG strain have never been identified. Moreover, recent efforts to genetically complement BCG virulence with genomic libraries of virulent tubercle bacilli have also been unsuccessful again suggesting that multiple unlinked mutations are responsible for the attenuation of BCG virulence. The antigenicity of BCG and the characteristics leading to its avirulence are thus poorly understood.

SUMMARY OF THE INVENTION

The present invention provides specific genetic deletions that account for the avirulent phenotype of the bacille Calmette-Guérin (BCG) strain of *Mycobacterium bovis*. These deletions may be used as phenotypic markers of providing a means for distinguishing between disease-producing and non-disease producing mycobacteria.

In a preferred embodiment, this invention provides for nucleic acid sequences that are markers for avirulent or virulent mycobacteria. The sequences uniquely characterize the presence or absence of deletions that result in an avirulent phenotype. More specifically the sequence are either deletion junction sequence or deletion sequences or subsequences within deletion junction sequences or deletion sequences. Thus, this invention provides for a marker for an avirulent mycobacterium comprising a first nucleic acid that hybridizes under stringent conditions with a second nucleic acid or a complement of the second nucleic acid where the second nucleic acid or its complement includes BCGΔ1a, BCGΔ1b, BCGΔ2a, BCGΔ2b, BCGΔ3a, BCGΔ3b, BCGΔ1ab, BCGΔ2ab, BCGΔ3ab, BCGΔ1, BCGΔ2, and BCGΔ3. In a particularly preferred embodiment, the marker specifically hybridizes under stringent conditions to a nucleic acid from BCG, but not to a nucleic acid from *Mycobacterium tuberculosis* or *Mycobacterium bovis*, or alternatively, the marker specifically hybridizes under stringent conditions to a nucleic acid from *Mycobacterium tuberculosis* or *Mycobacterium bovis*, but not to a nucleic acid from BCG. The marker may be the full length BCGΔ1a, BCGΔ1b, BCGΔ2a, BCGΔ2b, BCGΔ3a, BCGΔ3b, BCGΔ1ab, BCGΔ2ab, BCGΔ3ab, BCGΔ1, BCGΔ2, and BCGΔ3 or a subsequence within any of these regions. The marker may also include a nucleic acid having at least 80%, preferably 90%, more preferably 95%, and most preferably 98% percent sequence identity with BCGΔ1a, BCGΔ1b, BCGΔ2a, BCGΔ2b, BCGΔ3a, BCGΔ3b, BCGΔ1ab, BCGΔ2ab, BCGΔ3ab, BCGΔ1, BCGΔ2, or BCGΔ3. The marker may also include a sequence selected from an open reading frame of a the deletion sequences BCGΔ1, BCGΔ2, BCGΔ3. Suitable open reading frames are indicated in FIGS. 4, 5, and 6.

The above described marker may be a probe. The probe may be labeled by a number of means including, but not limited to radioactive, fluorescent, enzymatic, and colorimetric labels.

In another embodiment, this invention provides for polypeptides encoded by a subsequence of the BCGΔ1, BCGΔ2, or BCGΔ3 deletions. In particular, the subsequence may be selected from an open reading frame (ORF) present in one of these deletion sequences. This invention also provides for monoclonal or polyclonal antibodies that specifically bind polypeptides encoded by one or more subsequences of the BCGΔ1, BCGΔ2, or BCGΔ3 deletions.

In still another embodiment, this invention provides for a recombinant cell comprising a first nucleic acid that hybridizes under stringent conditions with a second nucleic acid or a complement of the second nucleic acid where the second nucleic acid or its complement is BCGΔ1a, BCGΔ1b, BCGΔ2a, BCGΔ2b, BCGΔ3a, BCGΔ3b, BCGΔ1ab, BCGΔ2ab, BCGΔ3ab, BCGΔ1, BCGΔ2, or BCGΔ3. The recombinant cell may be a mycobacterium. The recombinant cell may express a polypeptide encoded by any of BCGΔ1a, BCGΔ1b, BCGΔ2a, BCGΔ2b, BCGΔ3a, BCGΔ3b, BCGΔ1ab, BCGΔ2ab, BCGΔ3ab, BCGΔ1, BCGΔ2, and BCGΔ3. More preferably, the recombinant cell expresses a polypeptide encoded by an intact open reading frame present in any of these regions. The cell may also be a mycobacterium having one or more deletions in the BCGΔ1, BCGΔ2, or BCGΔ3 genomic regions where the deletions result in the attenuation of an otherwise virulent strain of mycobacterium and wherein the deletions are present in up to two of the genomic regions.

In still yet another embodiment, this invention provides a method of distinguishing between an attenuated and a virulent mycobacterium. The method involves detecting the presence or absence of a first nucleic acid that hybridizes under stringent conditions with a second nucleic acid or a complement of the second nucleic acid where the second nucleic acid or its complement is BCGΔ1a, BCGΔ1b, BCGΔ2a, BCGΔ2b, BCGΔ3a, BCGΔ3b, BCGΔ1ab, BCGΔ2ab, BCGΔ3ab, BCGΔ1, BCGΔ2, or BCGΔ3. The first nucleic acid may include any of the markers described above. A particularly preferred marker is one that specifically hybridizes under stringent conditions to a nucleic acid from BCG but not to a nucleic acid from *Mycobacterium tuberculosis* or *Mycobacterium bovis*, or alternatively, that specifically hybridizes under stringent conditions to a nucleic acid from *Mycobacterium tuberculosis* or *Mycobacterium bovis*, but not to a nucleic acid from BCG. The method may involve amplifying either the first nucleic acid by any of a number of methods including, for example, polymerase chain reaction. The detection may involve detecting the first nucleic acid, for example, as in a Southern blot, or alternatively, detecting a polypeptide encoded by the first nucleic acid. More specifically, the polypeptide may be a encoded by an open reading frame (ORF) selected from BCGΔ1, BCGΔ2, or BCGΔ3. The polypeptide may be visualized by a number of means well known to those of skill in the art including antibody hybridization such as direct or indirect binding of labeled antibody.

This invention additionally provides a method for determining whether an attenuated or a virulent Mycobacterium is present in a sample. This method involves providing a first nucleic acid that hybridizes under stringent conditions with a second nucleic acid or a complement of the second nucleic acid where the second nucleic acid or its complement is BCGΔ1a, BCGΔ1b, BCGΔ2a, BCGΔ2b, BCGΔ3a, BCGΔ3b, BCGΔ1ab, BCGΔ2ab, BCGΔ3ab, BCGΔ1, BCGΔ2, or BCGΔ3; and hybridizing the first nucleic acid to the biological sample. The first nucleic acid may include any of the markers described above. A particularly preferred marker is one that specifically hybridizes under stringent conditions to a nucleic acid from BCG but not to a nucleic acid from *Mycobacterium tuberculosis* or *Mycobacterium bovis*, or alternatively, that specifically hybridizes under stringent conditions to a nucleic acid from *Mycobacterium tuberculosis* or *Mycobacterium bovis*, but not to a nucleic acid from BCG. The method may involve amplifying either the first nucleic acid by any of a number of methods including, for example, polymerase chain reaction. The detection may involve detecting the first nucleic acid, for example, as in a Southern blot, or alternatively, detecting a polypeptide encoded by the first nucleic acid. More specifically, the polypeptide may be a encoded by an open reading frame (ORF) selected from BCGΔ1, BCGΔ2, or BCGΔ3. The method may also include detecting the hybridized first nucleic acid. This may involve direct detection of a label or additionally involve an amplification step and subsequent detection of the amplified product.

Finally, this invention provides a method of producing an attenuated-virulence mycobacterium. This method involves deleting from the genomic DNA of a virulent mycobacterium a first nucleic acid that specifically hybridizes under stringent conditions with a second nucleic acid or a complement of said second nucleic acid where said second nucleic acid or complement of said second nucleic acid is selected from the group consisting of BCGΔ1, BCGΔ2, and BCGΔ3. The first nucleic acid may be BCGΔ1, BCGΔ2, or BCGΔ3, or alternatively, it may be a promoter, other control element or an open reading frame from BCGΔ1, BCGΔ2, or BCGΔ3.

Definitions

Although any methods and materials similar or equivalent to those described herein can be used in the practice or testing of the present invention, the preferred methods and materials are described. For purposes of the present invention, the following terms are defined below.

The phrase "specifically detect" as used herein refers to the process of determining that a particular subsequence is present in a DNA sample. A DNA sequence may be specifically detected through a number of means known to those of skill in the art. These would include, but are not limited to amplification of the particular target sequence through polymerase chain reaction or ligase chain reaction, hybridization of the sequence to a labeled probe, and binding by labelled ligands or monoclonal antibodies. For a discussion of various means of detection of specific nucleic acid sequences see Perbal, B. *A Practical Guide to Molecular Cloning*, 2nd Ed. John Wiley & Sons, N.Y. (1988) which is incorporated herein by reference.

The phrase "select subsequence" is used herein to refer to a particular DNA subsequence that is of interest. It is often a predetermined or known sequence of nucleic acid bases. A select subsequence is typically chosen because of a unique sequence identity. Typically a select subsequence is targeted for DNA amplification and often is useful as a specific marker for the presence of a particular gene or a deletion of a particular nucleic acid sequence.

The term "oligonucleotide" refers to a molecule comprised of two or more deoxyribonucleotides or ribonucleotides. Oligonucleotides may include, but are not limited to, primers, probes, nucleic acid fragments to be detected, and nucleic acid controls. Oligonucleotides include naturally occurring nucleotides, chemically modified naturally occurring nucleotides and synthetic nucleotides. The exact size of an oligonucleotide depends on many factors and the ultimate function or use of the oligonucleotide.

The term "primer" refers to an oligonucleotide, whether natural or synthetic, capable of acting as a point of initiation of DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature. A primer is preferably a single-stranded oligodeoxyribonucleotide. The appropriate length of a primer depends on the intended use of the primer but typically ranges from 15 to 25 nucleotides. Short primer molecules generally require cooler temperatures to form sufficiently stable hybrid complexes with the template. A primer need not reflect the exact sequence of the template but must be sufficiently complementary to hybridize with a template.

The phrase "PCR primers competent to amplify" as used herein refers to a pair of PCR primers whose sequences are complementary to DNA subsequences immediately flanking the DNA subsequence (target sequence) which it is desired to amplify. The primers are chosen to bind specifically those particular flanking subsequences and no other sequences present in the sample. The PCR primers are thus preferably chosen to amplify the unique target sequence and no other. Alternatively, the PCR primers may be selected to bind to sequences other than the target sequence where the amplification products can be subsequently distinguished (e.g. where the desired amplified sequence is different in size than other amplified sequences).

"Amplifying" or "amplification", which typically refer to an "exponential" increase in target nucleic acid, are used herein to describe both linear and exponential increases in the number of a select target sequence of nucleic acid.

The term "antisense orientation" refers to the orientation of nucleic acid sequence from a structural gene that is inserted in an expression cassette in an inverted manner with respect to its naturally occurring orientation. When the sequence is double stranded, the strand that is the template strand in the naturally occurring orientation becomes the coding strand, and vice versa.

The term "deletion" refers to a region of a nucleic acid which is not present in an organism, but which is present in another related organism. In the context of mycobacteria, a deletion refers, e.g., to a region of nucleic acid which is not present in one strain of mycobacteria, but which is present in another related strain. For instance, an avirulent mycobacterial strain can have a deletion in its genome relative to the genome of a related virulent mycobacterial strain.

The term "deletion junction" refers to the region of a nucleic acid spanning the insertion point of a deletion. Thus, where a region of a nucleic acid sequence is deleted (i.e. a deletion is present), the deletion junction spans the nucleotides that are immediately adjacent to the deletion. Conversely, where a region of a nucleic acid sequence is not deleted (i.e. the deletion is absent), two deletion junctions are present, each spanning respectively one end of the deletion sequence and its flanking sequence.

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, such as a polynucleotide sequence of FIGS. 1, 2, or 3, or may comprise a complete cDNA or gene sequence.

Generally, a reference sequence is at least 10 nucleotides in length, frequently at least 20 to 25 nucleotides in length, and often at least 50 nucleotides in length. Sequence comparisons between two (or more) polynucleotides are typically performed by comparing sequences of the two polynucleotides over a "comparison window" to identify and compare local regions of sequence similarity. A "comparison window", as used herein, refers to a segment of at least 10 contiguous nucleotide positions wherein a polynucleotide sequence may be compared to a reference sequence of at least 10 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences.

Optimal alignment of sequences for aligning a comparison window may be conducted by the local homology algorithm of Smith and Waterman *Adv. Appl. Math.* 2: 482 (1981), by the homology alignment algorithm of Needleman and Wunsch *J. Mol. Biol.* 48: 443 (1970); by the search for similarity method of Pearson and Lipman *Proc. Natl. Acad. Sci. (USA)* 85: 2444 (1988), or by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of sequence similarity over the comparison window) generated by the various methods is selected.

The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The term "identical" in the context of two nucleic acid or polypeptide sequences refers to the residues in the two sequences which are the same when aligned for maximum correspondence.

The terms "isolated" or "biologically pure" refer to material which is substantially or essentially free from components which normally accompany it as found in its native state. The isolated nucleic acid probes of this invention do not contain materials normally associated with their in situ environment, in particular nuclear, cytosolic or membrane associated proteins or nucleic acids other than those nucleic acids intended to comprise the nucleic acid probe itself.

The term "marker" refers to a characteristic which distinguishes one class of cells or compositions from a second class of cells or compositions. For instance, the deletions and deletion junctions described herein can be used to distinguish between strains (e.g., virulent and avirulent strains) of mycobacteria. While markers are indicators of associated features or properties, as used herein, markers may also be used for purposes other than indicating the associated feature or property. Thus, for example, a nucleic acid marker of virulence identifies a particular nucleic acid which may be used in a variety of contexts other than simply indicating virulence.

The term "nucleic acid" refers to a deoxyribonucleotide or ribonucleotide polymer in either single- or double-stranded form, and unless otherwise limited, encompassing known analogues of natural nucleotides that can function in a similar manner as naturally occurring nucleotides. Unless otherwise indicated, a particular nucleic acid sequence includes the complementary sequence thereof.

The term "operably linked" refers to functional linkage between a promoter and a second sequence, wherein the promoter sequence initiates transcription of RNA corresponding to the second sequence.

The term "peptide" or "polypeptide" refers to an amino acid polymer which is encoded by a nucleic acid. The peptide or polypeptide may include naturally occurring or modified amino acids.

The terms "probe" or "nucleic acid probe" refer to a molecule that binds to a specific sequence or subsequence of a nucleic acid. A probe is preferably a nucleic acid which binds through complementary base pairing to the full sequence or to a subsequence of a target nucleic acid. It will be understood by one of skill in the art that probes may bind target sequences lacking complete complementarily with the probe sequence depending upon the stringency of the hybridization conditions. The probes are preferably directly labelled as with isotopes, chromophores, lumiphores, chromogens, or indirectly labelled such with, e.g., biotin to which a streptavidin complex may later bind. By assaying for the presence or absence of the probe, one can detect the presence or absence of the selected sequence or subsequence.

The term "labeled nucleic acid probe" refers to a nucleic acid probe that is bound, either covalently, through a linker, or through ionic, van der Waals or hydrogen "bonds" to a label such that the presence of the probe may be detected by detecting the presence of the label bound to the probe.

The term "recombinant" when used with reference to a cell indicates that the cell replicates or expresses a nucleic acid, or expresses a peptide or protein encoded by DNA whose origin is exogenous to the cell. Recombinant cells can express genes that are not found within the native (non-recombinant) form of the cell. Recombinant cells can also express genes found in the native form of the cell wherein the genes are re-introduced into the cell by artificial means.

The term "sample" refers to a material with which bacteria may be associated. Frequently the sample will be a "clinical sample" which is a sample derived from a patient. Such samples include, but are not limited to, sputum, blood, blood cells (e.g., white cells), tissue or fine needle biopsy samples, urine, peritoneal fluid, and pleural fluid, or cells therefrom. It will be recognized that the term "sample" also includes supernatant from eukaryotic cell cultures (which may contain free bacteria), cells from cell or tissue culture, and other media in which it may be desirable to detect mycobacteria (e.g., food and water).

The term "subsequence" in the context of a particular nucleic acid sequence refers to a region of the nucleic acid equal to or smaller than the specified nucleic acid.

The term "substantial identity" or "substantial similarity" indicates that a nucleic acid or polypeptide comprises a sequence that has at least 90% sequence identity to a reference sequence, or preferably 95%, or more preferably 98% sequence identity to the reference sequence, over a comparison window of at least about 10 to about 100 nucleotides or amino acid residues. An indication that two polypeptide sequences are substantially identical is that one protein is immunologically reactive with antibodies raised against the second protein. An indication that two nucleic acid sequences are substantially identical is that the polypeptides which the first nucleic acids encodes is immunologically cross reactive with the polypeptide encoded by the second nucleic acid.

Another indication that two nucleic acid sequences are substantially identical is that the two molecules hybridize to each other under stringent conditions. Stringent conditions are sequence-dependent and will be different with different environmental parameters. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typically, stringent conditions will be those in which the salt concentration is at least about 0.2 molar at pH 7 and the temperature is at least about 60° C.

The term "uninterrupted reading frame" or "open reading frame" refers to a DNA sequence (e.g., cDNA) lacking a stop codon or other intervening, untranslated sequence. An intact open reading frame refers to a full length uninterrupted reading frame or minor variations thereof.

The term "virulent" in the context of mycobacteria refers to a bacterium or strain of bacteria that replicates within a host cell or animal at a rate that is detrimental to the cell or animal within its host range. More particularly virulent mycobacteria persist longer in a host than avirulent mycobacteria. Virulent mycobacteria are typically disease producing and infection leads to various disease states including fulminant disease in the lung, disseminated systemic miliary tuberculosis, tuberculosis meningitis, and tuberculosis abscesses of various tissues. Infection by virulent mycobacteria often results in death of the host organism. Typically, infection of guinea pigs is used as an assay for mycobacterial virulence. In contrast, the term "avirulent" refers to a bacterium or strain of bacteria that either does not replicate within a host cell or animal within its host range, or replicates at a rate that is not significantly detrimental to the cell or animal.

The term BCG-like avirulence, as used herein refers to an attenuated virulence brought about by one of the deletions of the present invention.

BRIEF DESCRIPTION OF THE DRAWINGS

FIG. 1 shows the complete sequence listing of the BCG deletion region 1 including flanking sequences. (SEQ ID NO.: 16). The deletion, designated BCGΔ1, is located between nucleotide 2327 and nucleotide 11126.

FIG. 2 shows the complete sequence listing of the BCG deletion region 2 including flanking sequences. (SEQ ID NO.: 17). The deletion, designated BCGΔ2, is located between nucleotide 3382 and nucleotide 14071.

FIG. 3 shows the complete sequence listing of the BCG deletion region 3 including flanking sequences. (SEQ ID NO.: 18). The deletion, designated BCGΔ3, is located between nucleotide 1406 and nucleotide 10673. "N" represents "A", "C", "G", or "T".

DETAILED DESCRIPTION

Figure 4:
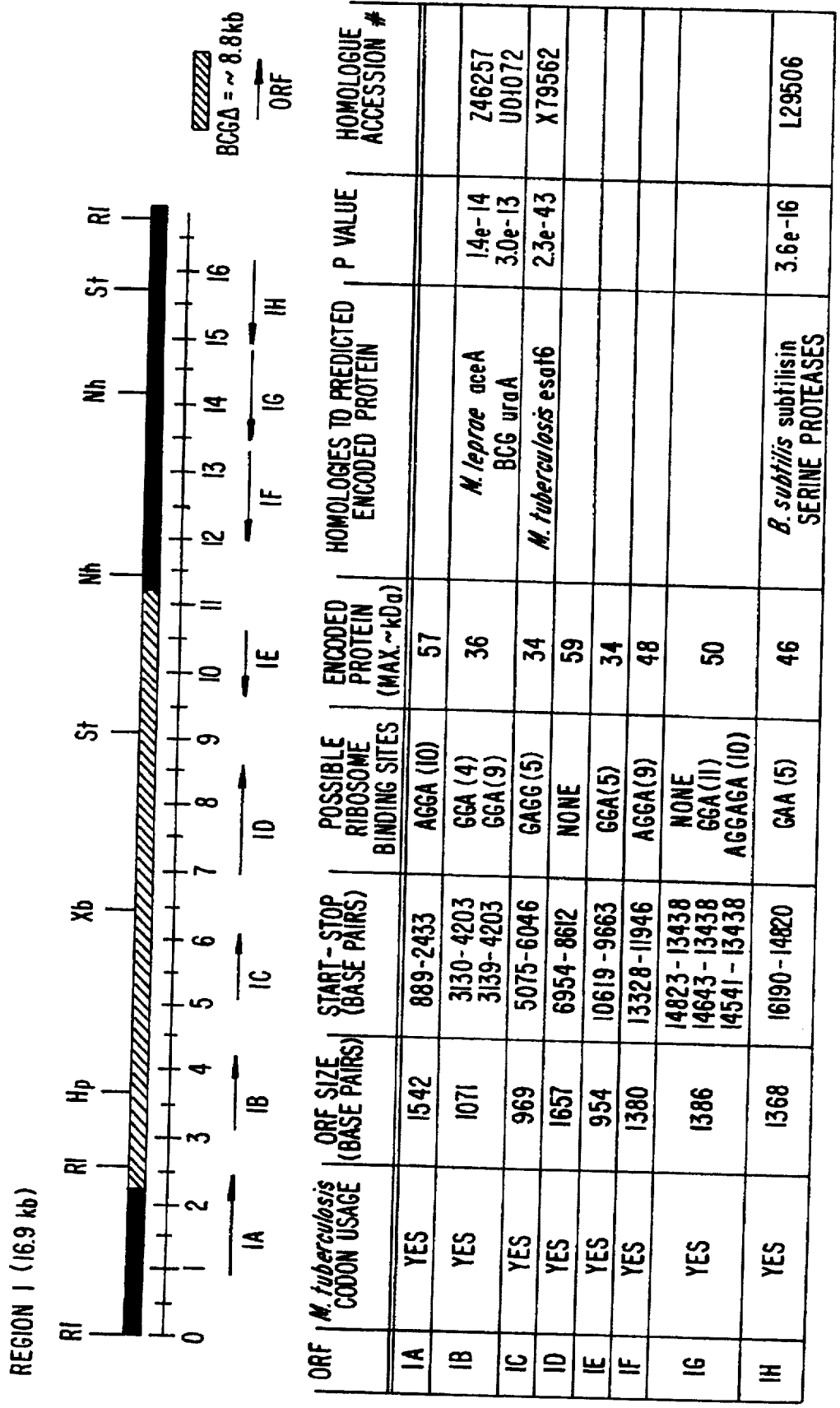
FIG. 4 shows a map of the deletion sequence BCGΔ1. This map identifies the various open reading frames (ORFs) and indicates their location within the deletion sequence. Ribozome binding sites and homologies to the predicted encoded proteins are shown.
Figure 5:
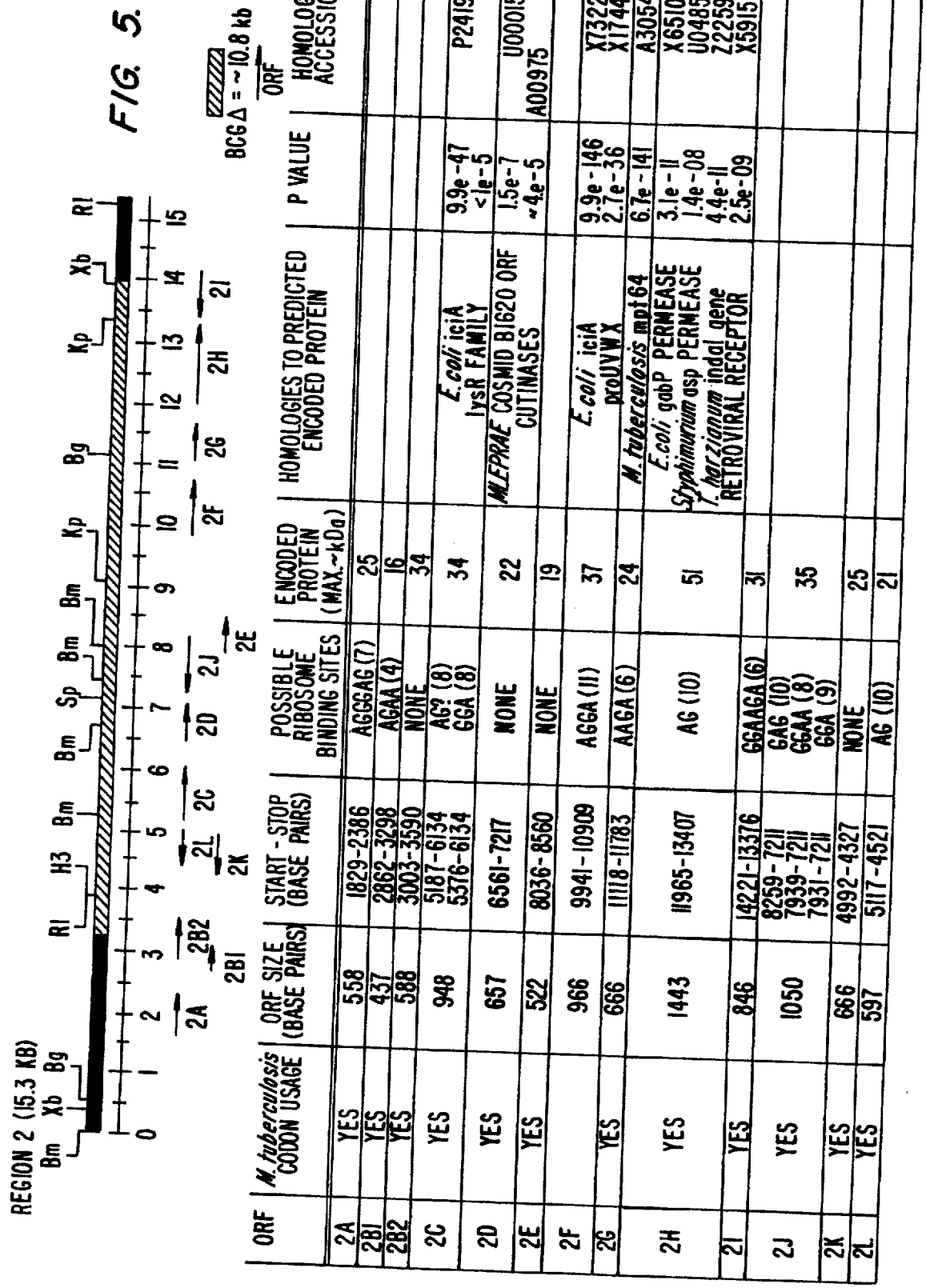
FIG. 5 shows a map of the deletion sequence BCGΔ2. This map identifies the various open reading frames (ORFs) and indicates their location within the deletion sequence. Ribozomal binding sites and homologies to the predicted encoded proteins are shown.

This invention reflects the discovery of genetic deletions in mycobacteria that result in an avirulent genotype such as is exhibited by the bacille Calmette-Guérin (BCG) mycobacterium. The original Pasteur bacille Calmette-Guérin (BCG) strain was developed by multiple (230 times) serial passages in liquid culture. BCG has never been shown to revert to virulence in animals indicating that the attenuating mutations in BCG are stable deletions and/or multiple mutations that cannot revert. The mutations that arose during serial passage of the original BCG strain were not previously known. Recent efforts to genetically complement BCG virulence with genomic libraries of virulent tubercle bacilli were unsuccessful, again suggesting that multiple unlinked mutations are responsible for the attenuation of BCG virulence.

The genetic deletions leading to the avirulent phenotype of BCG were identified by genomic subtractions between Connaught strain of BCG and MBV/MTB. The subtracted probe resulting from the genomic subtraction between BCG and the H37 Rv strain of *M. tuberculosis* was subsequently used to identify and clone three regions from a cosmid library of *Mycobacterium bovis* genomic DNA. Southern blot mapping and DNA sequence comparisons between BCG and *M. bovis* showed that three regions, designated regions 1–3, contained DNA segments of approximately 9 kb, 11 kb and 9 kb respectively, which are deleted in the Connaught strain of BCG. Precise deletion junctions were identified for each region by comparisons of BCG and corresponding virulent MBV sequences. The respective deletions, designated BCGΔ1, BCGΔ2 and BCGΔ3 are illustrated in FIGS. 1–3.

One of skill in the art will appreciate that the deletions encompassed by BCGΔ1, BCGΔ2 and BCGΔ3 may be utilized in a variety of contexts. For example, the deletions may be utilized to distinguish between avirulent and virulent strains of mycobacteria thereby providing early detection of patients at risk for tuberculosis. This is of particular importance where mycobacteria are identified in a sample from a patient that has been previously vaccinated with BCG. In this context it may be critical to determine whether mycobacteria identified in a biological sample from such a patient are pathogenic.

In another embodiment, the preparation of mycobacteria containing the deletions of the present invention may provide superior vaccines to BCG which has long been known to have marginal efficacy. Thus, for example, a *Mycobacterium tuberculosis* may contain a full BCGΔ1 deletion or a smaller deletion within BCGΔ1 (e.g. one or more open reading frames) rendering it avirulent. An avirulent MTB will provide a more efficient vaccine because it is antigenically more similar to MTB than is BCG. Moreover, an MTB rendered avirulent by the production of smaller deletions within the deletion regions identified in this invention will present more antigenic determinants.

Since the loss of virulence is due to the loss of gene products expressed by the nucleic acid sequences comprising the deletion regions, the BCGΔ1, BCGΔ2 and BCGΔ3 deletion sequences and proteins encoded within these deletion sequences provide suitable targets for drug screening. Thus, the use of deleted sequences as targets to screen for drugs that inhibit or interfere with transcription, translation, or post-translational processing of proteins encoded by the deletion sequences, or with the deletion encoded polypeptides themselves, provides an assay for anti-mycobacterial agents. In particular, the use of reporter genes such as firefly luciferase (FFlux), β-galactosidase (BGal), and the like, under the control of promoters present in the deletion sequence provide a rapid assay for drugs regulating activity originating in this region. Conversely, since the protein products of the deletion sequences are presumably expressed in virulent mycobacterial species, proteins expressed by deletion sequences may make good antigens for antimycobacterial vaccines.

Finally, as the viability of BCG demonstrates, deletion regions BCGΔ1, BCGΔ2 and BCGΔ3 are not required for mycobacterial growth and reproduction. Thus, these deletion regions provide good insertion points for the expression of heterologous DNA. The heterologous DNA sequences may be under the control of endogenous inducible or constitutive promoters typically found in the deletion sequences, or alternatively, they may be under the control of introduced promoters, either constitutive or inducible, exogenous to mycobacteria.

I. Detection of Deletions

As indicated above, the deletions identified in the present invention provide useful markers for the identification of an avirulent (or conversely a virulent) mycobacterial phenotype. Specifically, determination of avirulence simply requires the detection of the presence or absence of the deletion (either BCG-Δ1, BCGΔ2, or BCGΔ3, or deletions within these regions). Where the deletion is present in the bacterial DNA, the bacterium expresses a BCG-like avirulent phenotype. Conversely, where the deletion is absent in the bacterial DNA, the bacterium does not express a BCG-like avirulence. While this may indicate that the bacterium is virulent, one of skill will appreciate that the bacterium may still be avirulent due to the presence of other mutations or deletions. Nevertheless, screening for the presence of the deletion provides a means of detecting a BCG-like avirulent mycobacterium.

Means of detecting deletions are well known to those of skill in the art. Generally, the deletions may be detected either by detecting the presence or absence of deletion junctions, or, alternatively, by detecting the presence or absence of the sequences contained within the deletion (deletion sequences). Where a nucleic acid sequence is deleted (i.e., a deletion is present), the sequences that previously flanked the deleted sequence are juxtaposed, thereby forming a new deletion junction that spans the deletion. Detection of the presence of such a "spanning" deletion junction indicates the presence of the deletion and thus the avirulent phenotype.

Figure 7:
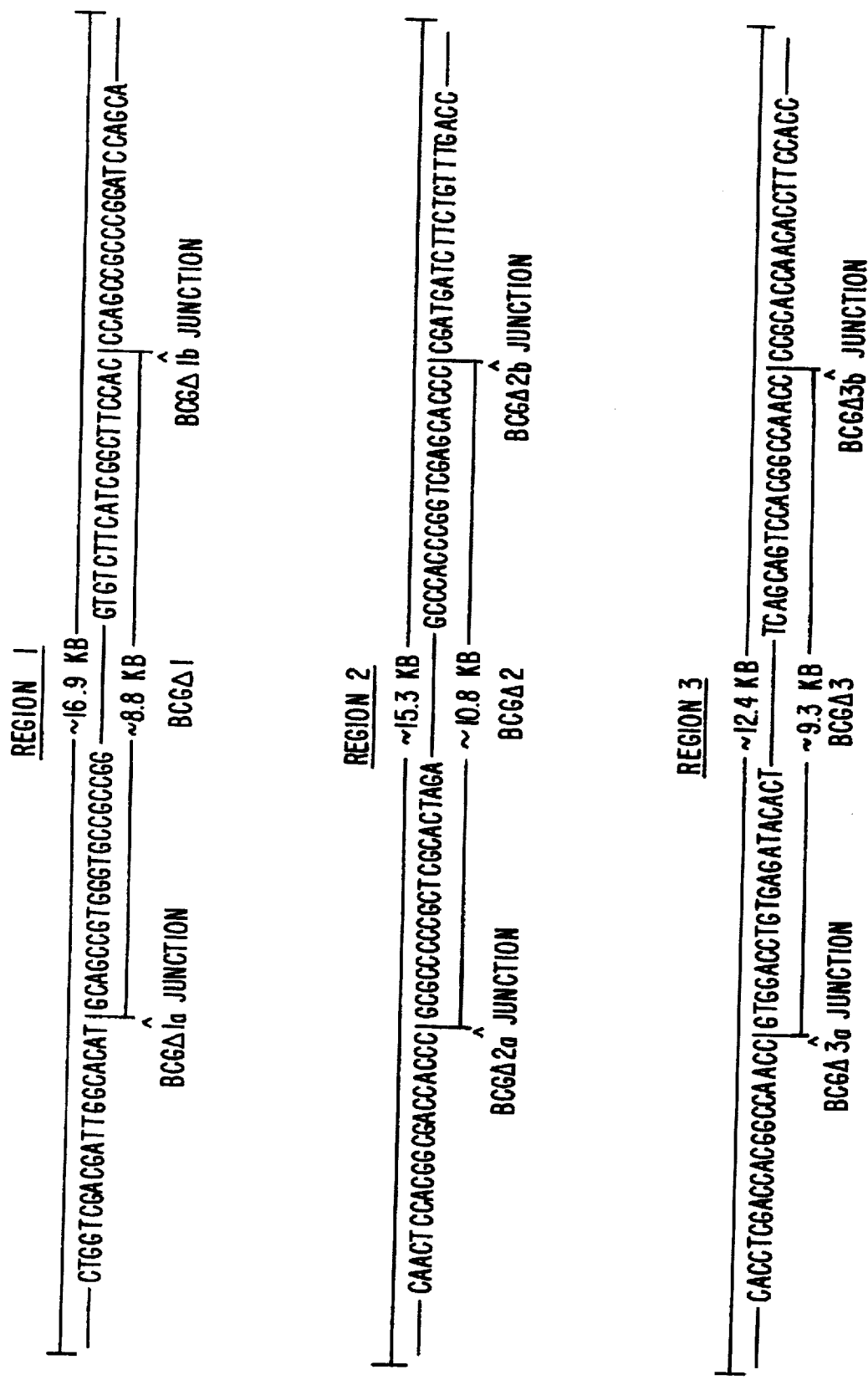
FIG. 7 illustrates the deletion junction regions of BCGΔ1, BCGΔ2, and BCGΔ3. The "terminal" deletion junction regions formed by the flanking sequences and the terminal regions of the deletion sequences are identified as BCGΔ1a, BCGΔ1b, BCGΔ2a, BCGΔ2b, and BCGΔ3a, and BCGΔ3b. When the deletion is present (the deletion sequences are missing) the respective "a" and "b" sequences will be juxtaposed, thereby forming deletion "spanning" junction sequences designated BCGΔ1ab, BCGΔ2ab, and BCGΔ3ab, respectively.

Conversely, where the nucleic acid sequence is not deleted (the deletion is not present) the spanning junction sequence will be absent (See, e.g. FIG. 7). The "terminal" deletion junction sequences flanking each endpoint of the deletion region are present and detection of these terminal deletion junctions indicates the absence of a deletion. Spanning deletion junction regions and terminal deletion junctions suitable for detecting the deletions of the present invention are illustrated in FIG. 7 and in Table 1.

TALBE 1

Nucleic acid sequences comprising deletion junctions. The symbol "l" indicates the insertion point of the deletion sequence. Deletion sequence bases are represented in lower case letters.

| Junction | Nucleotide Sequence | Seq. ID |
|---|---|---|
| BCGAΔ1a | CTGGTCGACGATTGGCACATlgcagccgtgggtgccgccgg | 1 |
| BCGΔ1b | gtgtcttcatcggcttccaclCCAGCCGCCCGGATCCAGCA | 2 |
| BCGΔ2a | CAACTCCACGGCGACCACCClgcgcccccgctcgcactaga | 3 |
| BCGΔ2b | gcccacccggtcgagcacclCGATGATCTTCTGTTTGACC | 4 |
| BCGΔ3a | CACCTCGACCACGGCCAACClgtggacctgtgagatacact | 5 |
| BCGΔ3b | tcagcagtccacggccaacclCCGCACCAACACCTTCCACC | 6 |
| BCGΔ1ab | CTGGTCGACGATTGGCACATICCAGCCGCCCGGATCCAGCA | 7 |
| BCGΔ2ab | CAACTCCACGGCGACCACCClCGATGATCTTCTGTTTGACC | 8 |
| BCGΔ3ab | CACCTCGACCACGGCCAACClCCGCACCAACACCTTCCACC | 9 |

Where a deletion is detected by determining the presence or absence of sequences contained within the deletion (deletion sequences), the absence of deletion sequences indicates the presence of a deletion and thus an avirulent phenotype. Conversely, the presence of deletion sequences indicates the absence of a deletion. Deletion sequences that provide suitable targets for detecting the deletions of the present invention are provided in FIGS. 1, 2 and 3.

A) Isolation of DNA for Detection of Mycobacterium Genomic Deletions

In a preferred embodiment, DNA is obtained from mycobacteria. As used herein, the term "mycobacteria" refers to any bacteria of the family Mycobacteriaceae (order Actinomycetales) and includes, but is not limited to, *Mycobacterium tuberculosis*, *Mycobacterium avium complex*, *Mycobacterium kansasii*, *Mycobacterium scrofulaceum*, *Mycobacterium bovis* and *Mycobacterium leprae*. These species and groups and others are described in Baron, S., ed. *Medical Microbiology*, 3rd Ed. (1991) Churchill Livingstone, N.Y., which is incorporated herein by reference.

The identification of deletions using a DNA marker requires that the DNA sequence be accessible to the particular probes used or to the components of the amplification system if the DNA sequence is to be amplified. In general, this accessibility is ensured by isolating the nucleic acids from the sample.

A variety of techniques for extracting nucleic acids from biological samples are known in the art. For example, see those described by Sambrook et al., *Molecular Cloning—A Laboratory Manual*, Cold Spring Harbor Laboratory, Cold Spring Harbor, N.Y., (1985), by Han, et al. *Biochemistry*, 26:1617–1625 (1987) and by Du, et al. *Bio/Technology*, 10:176–181 (1992), which are incorporated herein by reference.

Alternatively, if the sample is readily disruptable, the nucleic acid need not be purified prior to amplification by the PCR technique, i.e., if the sample is comprised of cells, particularly peripheral blood lymphocytes or monocytes, lysis and dispersion of the intracellular components may be accomplished merely by suspending the cells in hypotonic buffer or boiling them in a low concentration of alkali (i.e. 10 mM NaOH).

In a preferred embodiment, DNA is extracted from mycobacteria as described in Example 1.

B) Detection of Deletions Using Hybridization Probes

In one embodiment the avirulence deletions are detected by contacting DNA obtained from the mycobacterium with a probe that specifically binds an entire deletion junction region or a subsequence of that region and does not specifically bind to any other DNA sequences in the sample. Alternatively, a probe that specifically binds the entire deleted region or subsequence of that region and does not specifically bind to any other sequences in the sample is also suitable. While such probes may be proteins, oligonucleotide probes are preferred. Typically, the sequence of the oligonucleotide probe is chosen to be complementary to a select subsequence unique to the deletion junction or the deletion sequence, whose presence or absence is to be detected. Under stringent conditions the probe will hybridize with the select subsequence forming a stable duplex.

The probe is typically labeled. Detection of the label in association with the target DNA indicates either the presence or absence of the deletion. The probe may be used to detect the deletion junction or deletion sequences directly in a DNA sample without amplification of the deletion subsequences. In one embodiment, unamplified DNA sequences are probed using a Southern blot. The DNA of the sample is immobilized, on a solid substrate, typically a nitrocellulose filter or a nylon membrane. The substrate-bound DNA is then hybridized with the labeled probe under stringent conditions and non-specifically hybridized probe is washed away. Labeled probe detected in association with the immobilized mycobacterial sequences (e.g. bound to the substrate) indicates the presence of deletion sequences (e.g. BCGΔ1, BCGΔ2, or BCGΔ3) and therefore the absence of the deletion. Means for detecting specific DNA sequences are well known to those of skill in the art. Protocols for Southern blots as well as other detection methods are provided in Maniatis, et al. *Molecular Cloning: A Laboratory Manual*. Cold Spring Harbor Laboratory Press, NY (1982), which is incorporated herein by reference.

In another embodiment, the mycobacterial DNA subsequences are themselves labeled. They are then hybridized, under stringent conditions, with a probe immobilized on a solid substrate. Detection of the label in association with the immobilized probe indicates the presence or absence of the deletion.

In a preferred embodiment, the deletion junction sequences or subsequences or the deletion sequences or subsequences may be amplified by a variety of DNA amplification techniques (for example via cloning, polymerase chain reaction, ligase chain reaction, transcription amplification, etc.) prior to detection using a probe. Because the copy number of mycobacterial sequences bearing the virulence-attenuating deletions is low, the use of unamplified mycobacterial DNA results in an assay of low sensitivity. Amplification of mycobacterial DNA increases sensitivity of the assay by providing more copies of possible target subsequences. In addition, by using labeled primers in the amplification process, the mycobacterial DNA sequences are labeled as they are amplified.

C) Selection of Probes for Detection of the Deletion Junction Sequences or the Deletion Sequences Full length sequences are provided for the deletions BCGΔ1, BCGΔ2, and BCGΔ3 in FIGS. 1, 2 and 3 respectively. Using these sequence listings, one of skill in the art may easily determine appropriate probes or primers for the detection of the presence or absence of the deletion junctions or the deletion sequences. Generally speaking, a probe will be selected that hybridizes to the target junction sequences or deletion sequences, but not to other mycobacterial nucleic acid sequences under stringent conditions. The design of hybridization probes is well known in the art. See, for example, Sambrook et al, *Molecular Cloning—A Laboratory Manual*, Cold Spring Harbor Laboratory, Cold Spring Harbor, N.Y., (1989), which is incorporated herein by reference.

In a preferred embodiment, the probe is an oligonucleotide sequence complementary to a subsequence comprising a deletion junction (e.g. BCGΔ1a, BCGΔ1b, BCGΔ2a, BCGΔ2b, BCGΔ3a, BCGΔ3b, BCGΔ1ab, BCGΔ2ab, and BCGΔ3ab) or a sequence complementary to a subsequence of a deletion sequence (e.g. BCGΔ1, BCGΔ2, and BCGΔ3). The probe preferably has destabilizing mismatches with subsequences from other regions of the mycobacterial genome.

The exact length of the probe depends on many factors including the length of conserved regions around the deletions, the degree of sequence specificity desired, and the amount of internal complementarity within the probe. Such probes are preferably 17 to 25 bases in length. One of skill will recognize that longer probes specifically hybridize at higher temperatures. Generally, stringent conditions are selected to be about 5° C. to 20° C., more preferably about 10° C., lower than the thermal melting point ($T_m$) for the specific sequence at a defined ionic strength and pH. Under stringent conditions, the probe will specifically hybridize to a nucleic acid sequence from an avirulent mycobacterium such as BCG, but not to a nucleic acid sequence from a virulent mycobacterium such as MTB or MBV. Alternatively, Under stringent conditions, the probe will specifically hybridize to a nucleic acid sequence from a avirulent mycobacterium such as MTB or MBV, but not to a nucleic acid sequence from an avirulent mycobacterium such as BCG.

Oligonucleotide probes can be prepared by any suitable method, including, for example, cloning and restriction of appropriate sequences and direct chemical synthesis by a method such as the phosphotriester method of Narang et al. *Meth. Enzymol,* 68:90–99 (1979); the phosphodiester method of Brown et al., *Meth. Enzymol.* 68:109–151 (1979); the diethylphosphoramidite method of Beaucage et al., *Tetra. Lea.,* 22:1859–1862 (1981); and the solid support method of U.S. Pat. No. 4,458,066.

Probe detectability may be increased by the attachment of a label. As used herein, a label is any composition detectable by spectroscopic, photochemical, biochemical, immunochemical, electrical, optical or chemical means. Useful labels in the present invention include magnetic beads (e.g. DynabeadsT™), fluorescent dyes (e.g., fluorescein isothiocyanate, texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g. polystyrene, polypropylene, latex, etc.) beads.

Methods for attaching labels to probes, primers, and antibodies are well known to those of skill in the art. For example, the probe can be labeled at the 5'-end with $^{32}$P by incubating the probe with $^{32}$P-ATP and polynucleotide kinase (see Perbal, *A Practical Guide to Molecular Cloning,* 2nd ed. John Wiley, N.Y. (1988)). Other labels may be joined to the probe directly or through linkers. They may be located at the ends of the probe or internally. Methods of attaching labels may be found in Connell, et al., *Bio/Techniques* 5:342 (1987), U.S. Pat. Nos. 4,914,210, 4,391,904 and 4,962,029, which are incorporated herein by reference. In addition, kits for labelling oligonucleotides are widely available. See, for example, Boehringer Mannheim Biochemicals (Indianapolis, Ind.) for "Genius" labeling kits based on dioxigenin technology and Clonetech (South San Francisco, Calif.) for a variety of direct and indirect oligonucleotide labeling reagents.

D) Detection of Deletions Conferring Avirulence Through Amplification of Unique Subsequences Deletions are particularly amenable to detection without the use of a hybridization probe. In a preferred embodiment, subsequences are amplified that include a deletion junction. The amplified deletion junction may be a "spanning" deletion junction in which case where the deletion is present (i.e. the deletion sequences are absent), the amplification product is a specific DNA incorporating the deletion junction sequence spanning the deletion (e.g. incorporating flanking sequences from both sides of the deleted sequence). Where the deletion is absent (i.e. deletion sequences are present) and primers are selected so that there are no priming sites within the deletion sequences, amplification is non-existent or alternatively provides a complex mixture of non-specifically amplified fragments. Alternatively, amplification primers may be selected that specifically hybridize to deletion sequences, as long as they are selected to amplify sequences that are distinguishable from the sequence amplified when the deletion is present.

Alternatively, the amplification product may be subsequence of a "terminal" deletion junction in which case absence of the deletion (i.e. the deletion sequences are present) will result in the amplification of the specifically targeted nucleic acid. Conversely, where the deletions are present (i.e. the deletion sequences are absent) there will be no specific amplification of a terminal deletion junction.

Amplification products may be separated by size for characterization. Size separation may be accomplished by a variety of means known to those of skill in the art. These methods include, but are not limited to electrophoresis, density gradient centrifugation, liquid chromatography, and capillary electrophoresis. In a preferred embodiment, the fragments are separated by agarose gel electrophoresis. The bands are then stained with a marker to visualize them such as ethidium bromide and the gel is visualized, e.g., using ultraviolet light.

As described above, an agarose gel typically shows 1 band if the deletion is present, reflecting amplification of the deletion-spanning sequence. Where the deletion is absent, amplification results in either no bands, where there are no sequences within the deletion to which the amplification primers may hybridize, or a smear where there is non-specific amplification, or a series of discrete bands distinguishable from the band representing the deletion-spanning sequence where primers are chosen that hybridize to deletion sequences.

E) Selection of Primers for Amplification of Avirulence Deletions

Amplification of deletion junction sequences or subsequences or deletion sequences or subsequences may be accomplished by methods well known in the art, which include, but are not limited to polymerase chain reaction (PCR) (Innis, et al., *PCR Protocols. A guide to Methods and Application.* Academic Press, Inc. San Diego, (1990), which is incorporated herein by reference), ligase chain reaction (LCR) (see Wu and Wallace, *Genomics*, 4:560 (1989), Landegren, et al., *Science*, 241:1077 (1988) and Barringer, et al., *Gene*, 89:117 (1990), which are incorporated herein by reference), transcription amplification (see Kwoh, et al., *Proc. Natl. Acad. Sci.* (*U.S.A.*), 86:1173 (1989) which is incorporated herein by reference), and self-sustained sequence replication (see Guatelli, et al., *Proc. Nat. Acad. Sci.* (*U.S.A.*), 87:1874 (1990) which is incorporated herein by reference), each of which provides sufficient amplification so that the target sequence can be detected by nucleic acid hybridization to a probe or by electrophoretic separation. Alternatively, methods that amplify the hybridization probe to detectable levels can be used, such as Qβ-replicase amplification. See, for example, Kramer, et al. *Nature*, 339:401 (1989), Lizardi, et al. *Bio/Technology*, 6:1197 (1988), and Lomell, et al., *Clin. Chem.* 35:1826 (1989) which are incorporated herein by reference.

In a preferred embodiment, amplification is by polymerase chain reaction using a pair of primers that flank and thereby amplify a selected deletion junction subsequence. Selection of primers is readily apparent to one of skill in the art using the sequence listings of the present invention. For example, a pair of PCR primers 5'-TCGACGATTGGCACAT-3' (SEQ ID NO.: 10, $T_m$=55° C.) and 5'-TCCCTCCCTGTATTTGTAT-3' (SEQ ID NO.: 11, $T_m$=56° C.) will amplify a 469 base pair sequence including the BCGΔ1a deletion junction, while 5'-CGTTCTTCGGAGGTTTC-3' (SEQ ID NO.: 12, $T_m$=56° C.) and 5'-GGCGGCTGGGTGGA-3' (SEQ ID NO.: 13, $T_m$=60° C.) will amplify a 471 base pair sequence including the BCGΔ1b deletion junction.

F) Detection Of Deletions through Detection of Expression Products of Deletion Sequences In addition to the detection of deletions by the detection of either the deletion junction sequences or the deletion sequences, one may detect the absence of the deletion by detecting the expression products of the deletion sequences. Thus, for example, where the deletion sequences express a protein, the presence of that protein indicates the absence of the deletion and thus is indicative of a virulent (non BCG-like) phenotype. Such proteins are referred to herein as "deletion polypeptides".

Means of determining proteins expressed by particular nucleic acid sequences are well known to those of skill in the art. Typically this involves determining the longest open reading frame. This may be aided by the identification of initiation sites (e.g. ribozome binding sites). The protein encoded by the largest open reading frame is determined using codon preferences for the specific organism from which the nucleic acid is obtained. The polypeptide sequence listing may then be compared against a sequence database, e.g. GenBank, to determine other sequences sharing substantial sequence identity with the calculated sequence. The expression of the protein may be verified by isolating and then sequencing proteins having the predicted length and charge characteristics.

Once deletion polypeptides are identified they may be detected by routine methods well known to those of skill in the art. Typically this involves isolating and then detecting the polypeptide. The polypeptide may be isolated by a number of means well known to those of skill in the art. This includes typical methods of protein purification such as high performance liquid chromatography (HPLC), electrophoresis, capillary electrophoresis, hyperdiffusion chromatography, thin layer chromatography, and the like. Methods of purifying and detecting proteins are well known to those of skill in the art (see, e.g., *Methods in Enzymology Vol.* 182: *Guide to Protein Purification*, M. Deutscher, ed. Vol. 182 (1990), which is incorporated herein by reference).

Alternatively, deletion polypeptides sequences may be detected using immunoassays utilizing antibodies specific for the deletion polypeptides. The production of such antibodies and their use in immunoassays is detailed below.

G) Antibodies to Deletion Polypeptides

Antibodies can be raised to the polypeptides encoded by the nucleic acids corresponding to the open reading frames present in the deletion regions of the present invention (deletion polypeptides). As used herein "antibodies" include immunoglobulin or a population of immunoglobins which specifically bind to an antigen. Thus an antibody may be monoclonal or polyclonal including individual, allelic, strain, or species variants, and fragments thereof, both in their naturally occurring (full-length) forms and in recombinant forms. Additionally, antibodies can be raised to these polypeptides in either their native configurations or in non-native configurations. Anti-idiotypic antibodies may also be used.

1) Antibody Production

A number of immunogens may be used to produce antibodies specifically reactive with deletion polypeptides. Recombinant polypeptides are the preferred immunogen for the production of monoclonal or polyclonal antibodies. Naturally occurring polypeptides may also be used either in pure or impure form. Synthetic peptides made using sequences described herein may also used as immunogens for the production of antibodies.

Recombinant polypeptides are expressed in eukaryotic or prokaryotic cells and purified using standard techniques. The polypeptide is injected into an animal capable of producing antibodies. Either monoclonal or polyclonal antibodies may be generated for subsequent use in immunoassays to measure the presence and quantity of the polypeptide.

Methods of producing polyclonal antibodies are known to those of skill in the art. In brief, an immunogen, preferably a purified deletion polypeptide is mixed with an adjuvant and animals are immunized with the mixture. The animal's immune response to the immunogen preparation is monitored by taking test bleeds and determining the titer of reactivity to the polypeptide of interest. When appropriately high titers of antibody to the immunogen are obtained, blood is collected from the animal and antisera are prepared. Further fractionation of the antisera to enrich for antibodies reactive to the polypeptide is performed where desired. See, e.g., Coligan (1991) *Current Protocols in Immunology* Wiley/Greene, NY; and Harlow and Lane (1989) *Antibodies: A Laboratory Manual* Cold Spring Harbor Press, NY, which are incorporated herein by reference.

Monoclonal antibodies may be obtained by various techniques familiar to those skilled in the art. Description of techniques for preparing such monoclonal antibodies may be found in, e.g., Stiles et al. (eds.) *Basic and Clinical Immunology* (4th ed.) Lange Medical Publications, Los Altos, Calif., and references cited therein; Harlow and Lane (1988) *Antibodies: A Laboratory Manual* CSH Press; Goding (1986) *Monoclonal Antibodies: Principles and Practice* (2d ed.) Academic Press, New York, N.Y.; and particularly in Kohler and Milstein (1975) *Nature* 256: 495–497, which discusses one method of generating monoclonal antibodies.

Summarized briefly, this method involves injecting an animal with an immunogen. The animal is then sacrificed and cells taken from its spleen, which are then fused with myeloma cells (See, Kohler and Milstein (1976) *Eur. J. Immunol.* 6: 511–519, incorporated herein by reference). The result is a hybrid cell or "hybridoma" that is capable of reproducing in vitro.

Colonies arising from single immortalized cells are screened for production of antibodies of the desired specificity and affinity for the antigen, and yield of the monoclonal antibodies produced by such cells is enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al. (1989) *Science* 246: 1275–1281. In this manner, the individual antibody species obtained are the products of immortalized and cloned single B cells from the immune animal generated in response to a specific site recognized on the immunogenic substance.

Other suitable techniques involve selection of libraries of antibodies in phage or similar vectors. See, Huse et al. *Science* 246:1275–1281 (1989); and Ward, et al. *Nature* 341:544–546 (1989). The polypeptides and antibodies of the present invention are used with or without modification, including chimeric antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced. See, Cabilly, U.S. Pat. No. 4,816,567; and Queen et al. *Proc. Nat'l Acad. Sci. USA* 86:10029–10033 (1989).

Antibodies, including binding fragments and single chain versions, against predetermined fragments of deletion polypeptides can be raised by immunization of animals with conjugates of the fragments with carrier proteins as described above. Monoclonal antibodies are prepared from cells secreting the desired antibody. These antibodies can be screened for binding to normal or defective polypeptides, or screened for agonistic or antagonistic activity, e.g., mediated through a receptor. These monoclonal antibodies will usually bind with at least a $K_D$ of about 1 mM, more usually at least about 300 µM, and most preferably at least about 0.1 µM or better.

The antibodies of this invention can also be used for affinity chromatography in isolating deletion polypeptides. Columns can be prepared where the antibodies are linked to a solid support, e.g., particles, such as agarose, Sephadex, or the like, where a bacterial lysate, or recombinant cell lysate is passed through the column, washed, and treated with increasing concentrations of a mild denaturant, whereby purified deletion polypeptides are released.

The antibodies can be used to screen expression libraries for particular expression products. Usually the antibodies in such a procedure will be labeled with a moiety allowing easy detection of presence of antigen by antibody binding.

In a preferred embodiment, antibodies to deletion polypeptides are used for the identification of cell populations expressing the polypeptides. By assaying the expression products of cells expressing the polypeptides it is possible to diagnose bacterial infections.

Antibodies raised against each polypeptide are useful to raise anti-idiotypic antibodies. These will be useful in detecting or diagnosing various immunological conditions related to the presence of the respective antigens.

2) Immunoassays

A particular deletion polypeptide can be measured by a variety of immunoassay methods. For a review of immunological and immunoassay procedures in general, see Stiles and Terr (eds.) 1991 *Basic and Clinical Immunology* (7th ed.). Moreover, the immunoassays of the present invention can be performed in any of several configurations, e.g., those reviewed in Maggio (ed.) (1980) *Enzyme Immunoassay* CRC Press, Boca Raton, Fla.; Tijan (1985) "Practice and Theory of Enzyme Immunoassays," *Laboratory Techniques in Biochemistry and Molecular Biology*, Elsevier Science Publishers B.V., Amsterdam; and Harlow and Lane *Antibodies, A Laboratory Manual*, supra, each of which is incorporated herein by reference. See also Chan (ed.) (1987) *Immunoassay: A Practical Guide Academic Press*, Orlando, Fla.; Price and Newman (eds.) (1991) *Principles and Practice of Immunoassays* Stockton Press, NY; and Ngo (ed.) (1988) *Non-isotopic Immunoassays* Plenum Press, NY.

Immunoassays for measurement of deletion polypeptides can be performed by a variety of methods known to those skilled in the art. In brief, immunoassays to measure the protein can be, e.g., competitive or noncompetitive binding assays. In competitive binding assays, the sample to be analyzed competes with a labeled analyte for specific binding sites on a capture agent bound to a solid surface. Preferably the capture agent is an antibody specifically reactive with a deletion polypeptide produced as described above. The concentration of labeled analyte bound to the capture agent is inversely proportional to the amount of free analyte present in the sample.

In a competitive binding immunoassay, the deletion polypeptide present in the sample competes with labelled protein for binding to a specific binding agent, for example, an antibody specifically reactive with a particular deletion polypeptide. The binding agent is, e.g., bound to a solid surface to produce separation of bound labelled polypeptide from the unbound labelled polypeptide. Alternately, the competitive binding assay may be conducted in liquid phase and any of a variety of techniques known in the art may be used to separate the bound labelled protein from the unbound labelled protein. Following separation, the amount of bound labeled protein is determined. The amount of polypeptide present in the sample is inversely proportional to the amount of labelled polypeptide binding.

Alternatively, a homogenous immunoassay may be performed in which a separation step is not needed. In these immunoassays, the label on the protein is altered by the binding of the protein to its specific binding agent. This alteration in the labelled protein results in a decrease or increase in the signal emitted by label, so that measurement of the label at the end of the immunoassay allows for detection or quantitation of the polypeptide.

Deletion polypeptides may also be detected by a variety of noncompetitive immunoassay methods. For example, a two-site, solid phase sandwich immunoassay may be used. In this type of assay, a binding agent for the protein, for example an antibody, is attached to a solid support. A second protein binding agent, which is also an antibody, and which binds the protein at a different site, is labelled. After binding at both sites on the protein, the unbound labelled binding agent is removed and the labelled binding agent bound to the solid phase is measured. The amount of labelled binding agent bound is directly proportional to the amount of polypeptide in the sample.

Western blot analysis can be used to determine the presence of a deletion polypeptide in a sample. Electrophoresis is carried out, for example, on a bacterial sample suspected of containing the deletion polypeptide. Following electrophoresis to separate the proteins, and transfer of the proteins to a suitable solid support such as a nitrocellulose filter, the solid support is incubated with an antibody reactive with the protein. This antibody is labelled, or alternatively may be it is detected by subsequent incubation with a second labelled antibody that binds the primary antibody.

The immunoassay formats described above employ labelled assay components. The label can be in a variety of forms as described above. The choice of label depends on sensitivity required, ease of conjugation with the compound, stability requirements, and available instrumentation. For a review of various labelling or signal producing systems which may be used, see U.S. Pat. No. 4,391,904, which is incorporated herein by reference.

Antibodies reactive with a particular protein can also be measured by a variety of immunoassay methods. For a review of immunological and immunoassay procedures applicable to the measurement of antibodies by immunoassay techniques, see Stites and Terr (eds.) *Basic and Clinical Immunology* (7th ed.) supra; Maggio (ed.) *Enzyme Immunoassay*, supra; and Harlow and Lane *Antibodies, A Laboratory Manual*, supra.

In brief, immunoassays to measure antisera reactive with polypeptides include competitive and noncompetitive binding assays. In competitive binding assays, the sample analyte competes with a labeled analyte for specific binding sites on a capture agent bound to a solid surface. Preferably the capture agent is a purified recombinant deletion polypeptide as described above. Other sources of polypeptides, including isolated or partially purified naturally occurring protein, can also be used. Noncompetitive assays are typically sandwich assays, in which the sample analyte is bound between two analyte-specific binding reagents. One of the binding agents is used as a capture agent and is bound to a solid surface. The second binding agent is labelled and is used to measure or detect the resultant complex by visual or instrument means. A number of combinations of capture agent and labelled binding agent can be used. A variety of different immunoassay formats, separation techniques and labels can be also be used similar to those described above for the measurement of deletion polypeptides.

II. Preparation of Deletion-Containing Mycobacteria

Mycobacteria containing specific deletions may be prepared by using methods of homologous recombination well known to those of skill in the art. In brief, homologous recombination is a natural cellular process which results in the scission of two nucleic acid molecules having identical or substantially similar (i.e. "homologous") sequences, and the ligation of the two molecules such that one region of each initially present molecule is now ligated to a region of the other initially present molecule (Sedivy, *Bio/Technol.*, 6:1192–1196 (1988).

Homologous recombination is exploited by a number of various methods of "gene targeting" well known to those of skill in the art. (see, for example, Mansour et al. *Nature*, 336:348–352 (1988); Capecchi *Trends Genet.* 5:70–76 (1989); Capecchi *Science* 244:1288—1292 (1989); Capecchi et al. pages 45–52 In: *Current Communications in Molecular Biology*, Capecchi, M. R. (ed.), Cold Spring Harbor Press, Cold Spring Harbor, N.Y. (1989); Frohman et al. *Cell* 56:145–147 (1989)). Some approaches focus on increasing the frequency of recombination between two DNA molecules by treating the introduced DNA with agents which stimulate recombination (e.g. trimethylpsoralen, UV light, etc.), however, most approaches utilize various combinations of selectable markers to facilitate isolation of the transformed cells.

One such selection method is termed positive/negative selection (PNS) (Thomas and Cappechi *Cell* 51:503–512 (1987)). This method involves the use of two selectable markers: one a positive selection marker such as the bacterial gene for neomycin resistance ($neo^r$); the other a negative selection marker such as the herpes virus thymidine kinase (tk) gene. $Neo^r$ confers resistance to the drug G-418, while herpes tk renders cells sensitive to the nucleoside analog gangcyclovir (GANC) or 1-(2-deoxy-2-fluoro-b-d-arabinofuranosyl)-5-iodouracil (FIAU). The DNA encoding the positive selection marker in the transgene (e.g. $neo^R$) is generally linked to an expression regulation sequence that allows for its independent transcription in mycobacteria. It is flanked by first and second sequence portions of at least a part of the deletion or deletion flanking sequences.

These first and second sequence portions target the transgene to a specific nucleotide sequence. A second independent expression unit capable of producing the expression product for a negative selection marker, e.g. for herpes virus tk is positioned adjacent to or in close proximity to the distal end of the first or second portions of the first DNA sequence. Upon transfection, some of the mycobacteria incorporate the transgene by random integration, others by homologous recombination between the endogenous allele and sequences in the transgene. As a result, one copy of the targeted nucleic acid is disrupted by homologous recombination with the-transgene with simultaneous loss of the sequence encoding herpes tk gene. Random integrants, which occur via the ends of the transgene, contain herpes tk and remain sensitive to GANC or FIAU. Therefore, selection, either sequentially or simultaneously with G418 and GANC enriches for transfected mycobacteria containing the transgene integrated into the genome by homologous recombination.

Methods of homologous recombination in mycobacteria are described in greater detail by Ganjam et al. *Proc. Natl. Acad. Sci. USA*, 88:5433–5437 (1991) and Aldovini et al., *J. Bacteriol.*, 175:7282–7289 (1993) which are incorporated herein by reference.

III. Screening for Drug Susceptibility/Therapeutics

The expression products of the open reading frames in the BCGΔ1, BCGΔ2, and BCGΔ3 deletions of the present invention are targets for anti-mycobacterial drugs. To determine particularly suitable drug targets, open reading frames and surrounding expression control sequences are introduced into avirulent strains of mycobacteria, alone or in combination with other open reading frame regions to determine which regions are critical for virulence. Once particular genes are identified as critical for virulence, anti-mycobacterial agents are designed to inhibit expression of the critical genes, or to attack the critical gene products. For instance, antibodies are generated against the critical gene products and used as prophylactic or therapeutic agents. Alternatively, small molecules can be screened for the ability to selectively inhibit expression of the critical gene products, e.g., using recombinant expression systems which include the gene's endogenous promoter. These small molecules are then used as therapeutics, or prophylactic agents to inhibit mycobacterial virulence.

In another embodiment, anti-mycobacterial agents which render a virulent mycobacterium avirulent can be operably linked to expression control sequences and used to transform a virulent mycobacterium. Such anti-mycobacterial agents inhibit the replication of a specified mycobacterium upon transcription or translation of the agent in the mycobacterium.

Such transformed mycobacteria are useful as vaccine components, and as components of immunological infectivity assays. For instance, an animal's blood can be monitored for the presence of anti-mycobacterial antibodies using the procedures described herein, using transformed avirulent mycobacterial components in various immunological assays. Anti-mycobacterial agents useful in this invention include, without limitation, antisense genes, ribozymes, decoy genes, transdominant proteins and suicide genes.

An antisense nucleic acid is a nucleic acid that, upon expression, hybridizes to a particular mRNA molecule, to a transcriptional promoter or to the sense strand of a gene. By hybridizing, the antisense nucleic acid interferes with the transcription of a complementary DNA, the translation of an mRNA, or the function of a catalytic RNA. Antisense molecules useful in this invention include those that hybridize to gene transcripts in the region of the deletions of the invention, particularly deletion region 1.

A ribozyme is a catalytic RNA molecule that cleaves other RNA molecules having particular nucleic acid sequences. Ribozymes useful in this invention are those that cleave deletion gene transcripts. Examples include hairpin and hammerhead ribozymes.

A decoy nucleic acid is a nucleic acid having a sequence recognized by a regulatory DNA binding protein (i.e., a transcription factor). Upon expression, the transcription factor binds to the decoy nucleic acid, rather than to its natural target in the genome. Useful decoy nucleic acid sequences include any sequence to which a transcription factor binds in the deletion regions of the present invention.

A transdominant protein is a protein whose phenotype, when supplied by transcomplementation, will overcome the effect of the native form of the protein. For instance, an avirulent mycobacterium can be rendered virulent by introducing transdominant proteins from deletion region 1.

A suicide gene produces a product which is cytotoxic. In the vectors of the present invention, a suicide gene is operably linked to an inducible expression control sequences which is stimulated upon infection of a cell by a mycobacterium.

IV. Use Of Expressed "Deletion Proteins" in a Vaccine

The deletion polypeptides encoded by the open reading frames in BCGΔ1, BCGΔ2, and BCGΔ3 may be recombinantly expressed and used as components of immunological assays as described above or in vaccines. Expression of polypeptides encoded by the open reading frames of the BCGΔ1, BCGΔ2, or BCGΔ3 deletions may be accomplished by means well known to those of skill in the art.

In brief, the expression of natural or synthetic nucleic acids encoding deletion polypeptides will typically be achieved by operably linking the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of polynucleotide sequence encoding deletion polypeptides.

To obtain high level expression of a cloned gene, such as those polynucleotide sequences encoding deletion polypeptides, it is desirable to construct expression plasmids which contain, at the minimum, a promoter to direct transcription, a ribosome binding site for translational initiation, and a transcription/translation terminator. The expression vectors may also comprise generic expression cassettes containing at least one independent terminator sequence, sequences permitting replication of the plasmid in both eukaryotes and prokaryotes, i.e., shuttle vectors, and selection markers for both prokaryotic and eukaryotic systems. For detailed techniques employed in the recombinant expression of deletion proteins see, for example, Sambrook, et al., *Molecular Cloning: A Laboratory Manual* (2nd Ed., Vols. 1-3, Cold Spring Harbor Laboratory (1989)), *Methods in Enzymology*, Vol. 152: *Guide to Molecular Cloning Techniques* (Berger and Kimmel (eds.), San Diego: Academic Press, Inc. (1987)), or *Current Protocols in Molecular Biology*, (Ausubel, et al. (eds.), Greene Publishing and Wiley-Interscience, New York (1987), all of which are incorporated herein by reference.

The expressed deletion polypeptides may be used in a variety of assays. For example, the deletion polypeptides can be used as reagents in immunoblot assays to test whether a patient was previously exposed to virulent mycobacteria (i.e., to test whether the patient has antibodies to the deletion polypeptide). These assays have the advantage of discriminating between previous exposure to an avirulent mycobacterium (e.g., one used in a vaccine) and exposure to a virulent mycobacterium. Thus, vaccinated individuals can be tested for antibodies to the virulent mycobacterium without regard to whether the patient has been vaccinated with an avirulent mycobacterium.

The deletion polypeptides can also be used as antigenic vaccine components to direct antibodies to elements which are critical for virulence. These polypeptides can be added to existing vaccines (e.g., those based upon avirulent mycobacteria and which lack the deletion polypeptide) to supplement the range of antigenicity conferred by the vaccine, or they may be used apart from other mycobacterial antigens. The vaccines of the invention contain as an active ingredient an immunogenically effective amount of a deletion polypeptide or of a recombinant vector which includes the deletion polypeptide. The immune response can include the generation of antibodies; activation of cytotoxic T lymphocytes (CTL) against cells presenting peptides derived from the polypeptides or other mechanisms well known in the art. See e.g. Paul *Fundamental Immunology Third Edition* published by Raven press New York (incorporated herein by reference) for a description of immune response. Useful carriers are well known in the art, and include, for example, thyroglobulin, albumins such as human serum albumin, tetanus toxoid, and polyamino acids such as poly(D-lysine:D-glutamic acid). The vaccines can also contain a physiologically tolerable (acceptable) diluent such as water, phosphate buffered saline, and further typically include an adjuvant. Adjuvants such as incomplete Freund's adjuvant, aluminum phosphate, aluminum hydroxide, or alum are materials well known in the art.

The compositions are suitable for single administrations or a series of administrations. When given as a series, inoculations subsequent to the initial administration are given to boost the immune response and are typically referred to as booster inoculations.

The vaccine compositions of the invention are intended for parenteral, topical, oral or local administration. Preferably, the pharmaceutical compositions are administered parenterally, e.g., intravenously, subcutaneously, intradermally, or intramuscularly. Thus, the invention provides compositions for parenteral administration that comprise a solution of the agents described above dissolved or suspended in an acceptable carrier, preferably an aqueous carrier. A variety of aqueous carriers may be used, e.g., water, buffered water, 0.4% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient and more preferably at a concentration of 25%-75%.

For aerosol administration, the polypeptides are preferably supplied in finely divided form along with a surfactant and propellant. The surfactant should be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery.

The amount of vaccine administered to the patient will vary depending upon the composition being administered, the physiological state of the patient and the manner of administration.

Live attenuated recombinant viruses which include the deletion polypeptide, such as recombinant vaccinia or adenovirus vectors, are convenient alternatives as vaccines because they are inexpensive to produce and are easily transported and administered. Vaccinia vectors and methods useful in immunization protocols are described, for example, in U.S. Pat. No. 4,722,848, incorporated herein by reference.

Deletion sequences and subsequences of this invention may also be used in methods of genetic immunization. Briefly, genetic immunization involves transfecting cells in vivo with nucleic acids encoding pathogen specific antigens. The transformed host cells then express the antigen thereby stimulating the host immune system.

In the present invention, antigen-encoding deletion region sequences are used to transform mammalian host cells thereby resulting in the expression of the antigen by the host. This provokes an immune response by the host against the expressed antigen thereby conferring immunity on the host. Methods of genetic immunization are well known to those of skill in the art (see, e.g., Wang et al. *Proc. Natl. Acad. Sci. USA*, 90:4156–4160 (1993); Ulmer et al., *Science*, 259:1745–1749 (1993); Fynan et al. *DNA Cell Biol.*, 12:785–789 (1993); Fynan et al. *Proc. Natl. Acad. Sci. USA*, 90: 11478–11482 (1993); Robinson et al. *Vaccine*, 11:957–960 (1993); and Martinon et al. *Eur. J. Immunol.*, 23:1719–1722 (1993), which are incorporated herein by reference.

VI. Use of Promoters within Deletion Sequences for Expression Recombinant Proteins Bacille Calmette-Guérin (BCG) contains all three deletions (BCGΔ1, BCGΔ2, and BCGΔ3) and yet is able to grow and reproduce indicating that the sequences contained within the deletion are not essential for bacterial viability. These deletion regions therefore make good target sites for the insertion of heterologous DNA as mycobacteria are tolerant of disruption of the native genome in these regions. The BCGΔ1, BCGΔ2, and BCGΔ3 deletion regions therefore provide suitable target sites for the incorporation of expression cassettes and the subsequent expression of exogenous gene products. The expression cassettes typically comprise a nucleic acid sequence under the control of a promoter. The promoter may be either constitutive or inducible. The cassette may additionally comprise a selectable marker such as an antibiotic resistance gene, a gene encoding a fluorescent marker (e.g. green fluorescent protein), or a gene encoding an enzymatic marker (e.g. β-galactosidase).

Alternatively, genes under the control of endogenous promoters may be used as well. In one embodiment, reporter genes under the control of endogenous promoters found within the deletion sequences may be inserted at the deletion sites. These reporter genes may be utilized as an assay for antimycobacterial compounds that act by inhibiting transcription or translation of deletion sequences. Assaying for the reporter gene product in the presence of an antimycobacterial compound provides a measure of efficacy of that compound in upregulating or downregulating deletion sequence genes. Methods of use of mycobacterial reporter gene assays to screen for drug activity are described by Cooksey et at., *Antimicrob. Agents Chemother.*, 37: 1348–1352 (1993), and Jacobs et al., *Science*, 260:819–822 (1993) which are incorporated herein by reference.

EXAMPLES

The following examples are offered by way of illustration, not by way of limitation.

Example 1

Identification of Virulence-Attenuating Deletions

Bacterial Culture

All strains of Mycobacteria used in this study were maintained in 7H9 (Difco, Detroit Mich., USA) media supplemented with OADC (BBL) or were grown on 7H11 agar supplemented with oleic acid albumin dextrose complex (OADC). *Escherichia coli* (strain DH5α or NM554) was used as a host for all recombinant plasmids and cosmids. *E. coli* was maintained in LB medium with or without agar. Carbenicillin (100 μg/ml) was used in place of ampicillin for the selection of all *E. coli* plasmids.

Extraction of High Molecular Weight DNA

High molecular weight chromosomal DNA was prepared by diluting a late log phase culture of the respective mycobacterium 1:10 into a liter of 7H9 medium containing 1.5% glycine and continuing growth for 4 to 5 days. The cells were then harvested by centrifugation, washed once in TE (pH 8.0) and resuspended in 4 ml of 25% sucrose in 10X TE. 100 μg of lysozyme was added and the preparation was incubated at 37° C. for 2 hr followed by the addition of 100 μg of proteinase K and sarkosyl to a concentration of 1% weight/volume. Following overnight incubation at 65° C. the mixture was extracted 4 times with chloroform isoamyl alcohol 24:1, once with phenol/chloroform (1:1), and twice again with chloroform isoamyl alcohol. The resulting high molecular weight DNA was then run on a CsCl gradient as described by Hull et al. *Infect. Immun.*, 33:933–938 (1981), which is incorporated herein by reference, and subsequently dialyzed against 4 changes of TE. BCG DNA was physically sheared by passage through a 22 gauge needle until an average size of 3–10 kb was obtained (20–25 passages). This DNA was then biotinylated using photobiotin (Clonetech, Palo Alto, Calif., USA) according to the method of Straus and Ausubel, *Proc. Natl. Acad. Sci. USA*, 87:1889–1893 (1990), which is incorporated herein by reference.

DNA Subtraction

DNA subtraction was carried out between virulent *M. tuberculosis* H37Rv and avirulent BCG. H37R chromosomal DNA was selected because it was the most readily available chromosomal DNA from a virulent strain. In addition, *M. bovis* and *M tuberculosis* H37Rv are highly homologous.

*M. bovis/M. tuberculosis* specific probes were generated by the method of Straus and Ausubel, supra. with the following modifications. Sheared and biotinylated BCG DNA was used in a 10:1 excess for each round of subtraction. Wild type *M. tuberculosis* H37Rv DNA was digested with Sau3A to an average size of 1 kb. Hybridization conditions were 1M NaCl and 65° C. for 18 hours. Following five cycles (successive denaturation and reassociations) of subtraction, Sau3A1 adaptors (GACACTCTCGAGACATCACCGTCC (SEQ ID NO.: 14) and GATCGGACGGTGATGTCTCGAGAGTG (SEQ ID NO.: 15) were ligated to the subtraction product and amplified in a PCR reaction for 35 cycles (30 sec at 95° C., 30 sec at 55° C., and 3 min at 72° C.). The *M. tuberculosis/M. bovis* specific probes were radiolabeled by using one strand of the adaptor (GACACTCTCGAGACATCACCGTCC, SEQ ID NO.: 14) as a primer and labeling with $^{32}$P dCTP using the Klenow fragment of DNA polymerase.

An *M. bovis* cosmid library was constructed in the BamH1 site of sCOS (Stratagene, La Jolla Calif., USA) with subsequent in vitro packaging and infection of *E. coli* strain NM554 (Stratagene). 600 colonies were picked to Nytran circular membranes and the membranes prepared according to the method of Grunstein and Hogness, *Proc. Natl. Acad. Sci. USA*, 72:3961 (1975), which is incorporated herein by reference. These filters were then probed using the BCG subtracted probe and positive clones selected for further analysis. Cosmid DNA was prepared from selected clones by the method of Birnboim and Doly, *Nucleic Acids. Res.*, 7:1513 (1973) which is incorporated herein by reference. Restriction fragments that hybridize with the MTB/MBV specific probe were further subcloned into pGEM7z or pGEM5z (Promega, Madison, Wis., USA) for deletion analysis.

Plasmid DNA for DNA sequencing was prepared using Qiagen minicolumns (Qiagen Inc. Chatsworth Calif., USA) and sequenced by the method of Henikoff, *Gene*, 28:351–359 (1984), which is incorporated herein by reference, using the Erase A Base System (Promega). DNA sequencing reactions were run using a Perkin Elmer 9600 thermocycler and analyzed on an automated ABI sequencer. Analysis and assembly of contiguous DNA sequence was done using the ABI analysis software and SeQuencher sequence analysis software by Gene Clones Corp (Ann Arbor, Mich., USA).

Deletion Region 1 (BCGΔ1)

Sequence analysis of over 16 kb of MBV region 1 and homologous regions in BCG revealed the precise junctions for the deletion in BCG. Eight open reading frames were identified with codon usage biases matching that of known MTB and MBV genes (see map FIG. 4). The potential start and stop codons and predicted maximum protein coding capacity are listed in FIG. 4. Consensus ribosomal binding site sequences were found near potential start codons for seven of eight open reading frames. TBLASTN and FASTA sequence homology analysis with each potential ORF-encoded protein revealed significant homologies for 3 of 8 open reading frames in region 1.

Most notable is the ORF1C homology to an unpublished and uncharacterized sequence listed in Genbank as *M. tuberculosis* antigen esat6. A 65 base pair repeated overlapping (repeated ~2½ times) sequence was also recognized within the ORF1C (esat6) open reading frame. Also noteworthy are the significant homologies identified between ORF1H and bacterial serine proteases including *B. subtilus* subtilisin. Of the eight recognized open reading frames, four (ORFs 1B, 1C, 1D, and 1E) are located entirely within the 9 kb region deleted in BCG. One ORF traverses the BCG deletion junction in virulent *M. bovis*.

DNA probes from the 9 kb deletion in region 1 demonstrated that this region is absent in all BCG substrains and present in all virulent MBV and MTB strains tested. Furthermore, restriction fragment patterns observed in Southern blot analysis with region 1 probes are non-polymorphic and identical in virulent MBV and MTB. This region has far fewer direct and indirect repeats than the regions 2 (BCGΔ2) and 3 (BCGΔ3) characterized below.

The sequence of a small region, estimated to be less than 20 bp between basepair coordinates 10654 and 10664 in region 1 has been recalcitrant to automated sequencing. Therefore, pending sequence confirmation, the base pair coordinates given in the region 1 map (FIG. 4) are approximations. The precise sequence determination is likely to effect the Orf1E open reading frame.

Deletion Region 2 (BCGΔ2)

Sequence analysis of over 15 kb of MBV region 2 and homologous regions in BCG revealed the precise junctions for an 11 kb deletion in BCG. Thirteen open reading frames were identified with codon usage biases matching that of known MTB and MBV genes (see map FIG. 5). The potential start and stop codons and predicted maximum protein coding capacity are also shown in FIG. 5. Candidate consensus sequences resembling ribosomal binding sites were found near potential start codons for eight open reading frames. Of the thirteen open reading frames recognized in BCGΔ2, nine are located entirely within the 11 kb region deleted in most BCG strains while ORF2B2 and ORF2I traverse the deletion junctions.

TBLASTN and FASTA sequence homology analysis with each potential ORF-encoded protein revealed significant homologies for five open reading frames in BCGΔ2. A protein encoded by ORF2C exhibits striking similarity to the *E. coli* iciA protein which is thought to play a role in inhibiting and regulating the initiation of chromosomal replication. The iciA protein product is a member of the large LysR family of transcriptional regulatory proteins. Orf2F is highly homologous to an *S. typhimurium* ribonucleotide diphosphate reductase and a region of the *E. coli* and *S. typhimurium* proUVWX operon. Orf2H was found to have significant homology to *E. coli* and *S. typhimurium* permeases involved in aromatic amino acid transport and a eukaryotic cell retroviral receptor.

The Orf2G encoded protein was identical to the MTB mpt64 gene previously thought to encode a secreted antigen which is specifically expressed by MTB and not BCG strains. Recent analysis of mpt64 expression revealed that three BCG substrains do express mpt64 (Moreau, Tokyo, Russian). Probes specific for mpt64 or other non-repetitive parts of region 2 hybridized to all MTB strains tested and the same three BCG substrains shown to express mpt64. Of interest is the finding that these three BCG substrains are derived from the original Pasteur strain prior to 1925. The current Pasteur strain and all strains derived from the original Pasteur strain after 1925, including the Connaught strain used in the subtractive analysis in this study, are deleted in the 11 kb DNA segment contained within BCGΔ2. These data indicate that an additional mutational event deleting the 11 kb segment of region 2, occurred in the BCG Pasteur strain sometime after 1925.

Southern blot analysis with probes from different segments of region 2 revealed a repetitive element located within a 2 kb segment (8–10 kb) of region 2. This repetitive element is ubiquitous in all tubercle bacilli tested. This element provides a marker suitable for RFLP analysis of mycobacterial strains.

Deletion Region 3 (BCGΔ3)

Sequence analysis of the almost 11 kb region 3 sequence and comparison to a homologous region in BCG precisely identified the deletion junctions for BCG. Twelve potential open reading frames were recognized in the region 3 sequence, seven of which are entirely located within the 9 kb region deleted in BCG. At least 9 ORFs in BCGΔ3 exhibit codon usage preferences comparable to that of the tubercle bacilli. Sequence homology analysis of presumptive protein sequences encoded by six open reading frames in region 3 revealed highly significant homology to listed sequences. Orfs3B, 3D, and 3E exhibit homology to phage sequences, suggesting a phage derivation for 4 or more kb of DNA in region 3. Homology to putative open reading frames in two *M. leprae* cosmids was also observed including homology to a putative bid gene encoding a protein involved in biotin synthesis. Also of interest was homology between ORF3A and an MTB sequence (mce) associated with cell invasion and intracellular survival.

Southern blot analysis with segments of region 3 deleted in BCG revealed that prototype lab strains of virulent MBV and MTB all carry deletion region 3 DNA. However, clinical isolates from PHRI are highly polymorphic or deleted in region 3. This region contains many large direct and indirect repeats and, as mentioned above, at least 2 ORFs are homologous to phage sequences including homology to DNA invertases or recombinases. The repetitive nature of this region and the possible presence of a DNA recombinase could explain the polymorphisms observed in this region.

Figure 6:
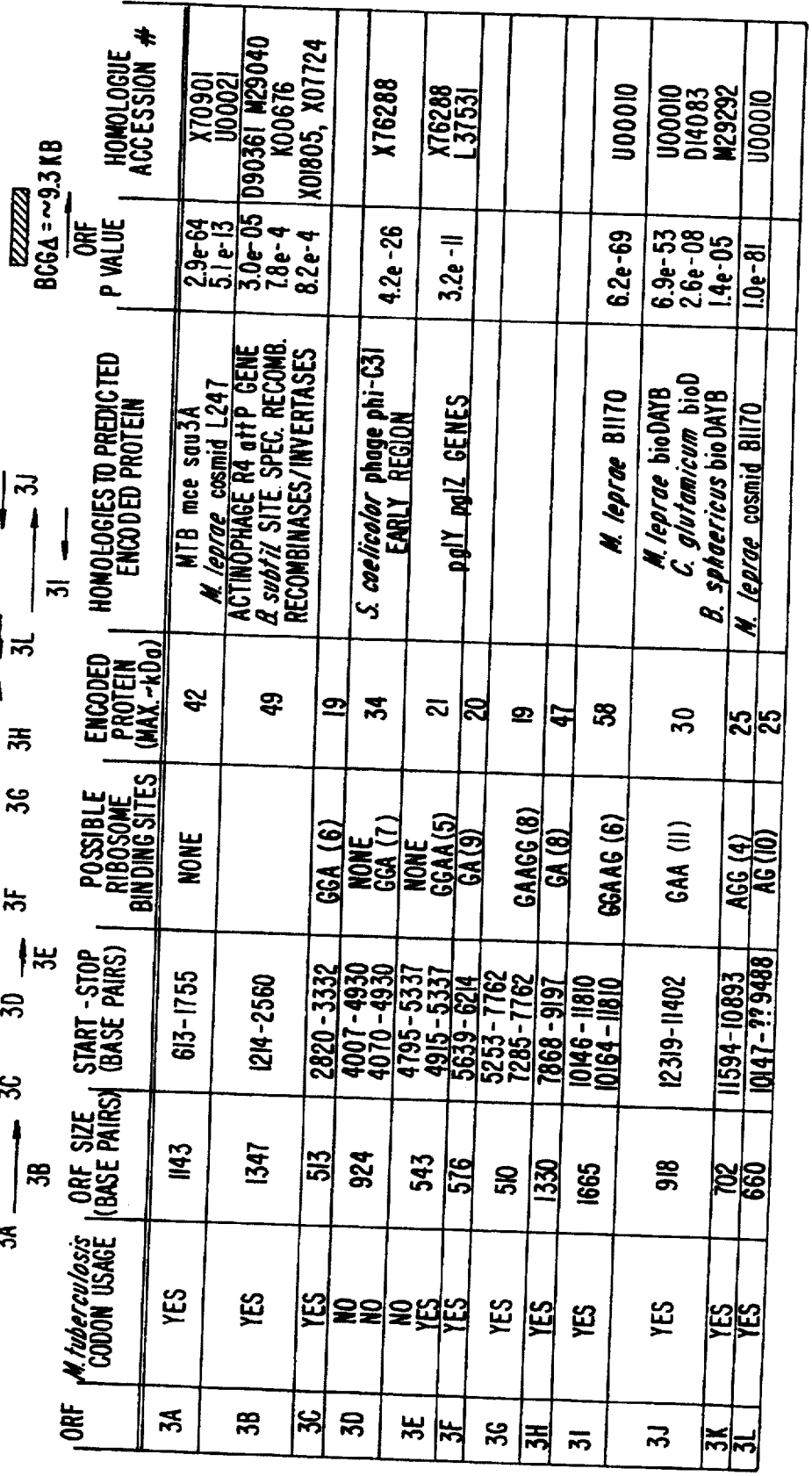
FIG. 6 shows a map of the deletion sequence BCGΔ3. This map identifies the various open reading frames (ORFs) and indicates their location within the deletion sequence. Ribozome binding sites and homologies to the predicted encoded proteins are shown. The sequence of a small region, estimated to be much less than 200 bp and located close to 9400 bp in FIG. 3, remains to be determined. Therefore, the base pair coordinates given in the region 3 map 3' to the 9 kb marker are approximations. The precise sequence determination of this region is likely to effect the length of open reading frames 3H and 3L.

The sequence of a small region, estimated to be much less than 200 bp and located close to 9400 bp in FIG. 3, was recalcitrant to automated sequencing and remains to be determined. Therefore, the base pair coordinates given in the region 3 map (FIG. 6) 3' to the 9 kb marker are approximations. The precise sequence determination of region is likely to effect the length of open reading frames 3H and 3L.

The foregoing subtractive analysis identified 3 regions in virulent *M. bovis* and *M. tuberculosis* prototype strains which are deleted in the avirulent BCG strain. The deletion located in region 2 may not have arisen in the original BCG Pasteur strain as this region is only deleted in strains derived from the original Pasteur strain after 1925. Region 3 is present in virulent MTB and MBV lab prototype strains (H37Rv, Erdman ) and is highly polymorphic and at least partially deleted in the majority of MTB clinical isolates tested. Region 1 is apparently conserved and intact in all virulent MBV and MTB strains tested to date while all avirulent BCG strains tested to date are missing approximately 9 kb from region 1.

Example 2

Screening and Identification of an Avirulent Mycobacterium

The $^{32}$P labeled subtraction probe obtained in Example 1, was used to probe EcoRI and BamHI restricted chromosomal DNAs from BCG Connaught, *Mycobacterium bovis*, and various strains of *Mycobacterium tuberculosis* in a Southern blot. The hybridization was performed at 70° C. in 6× SSC overnight.

Figure 8:
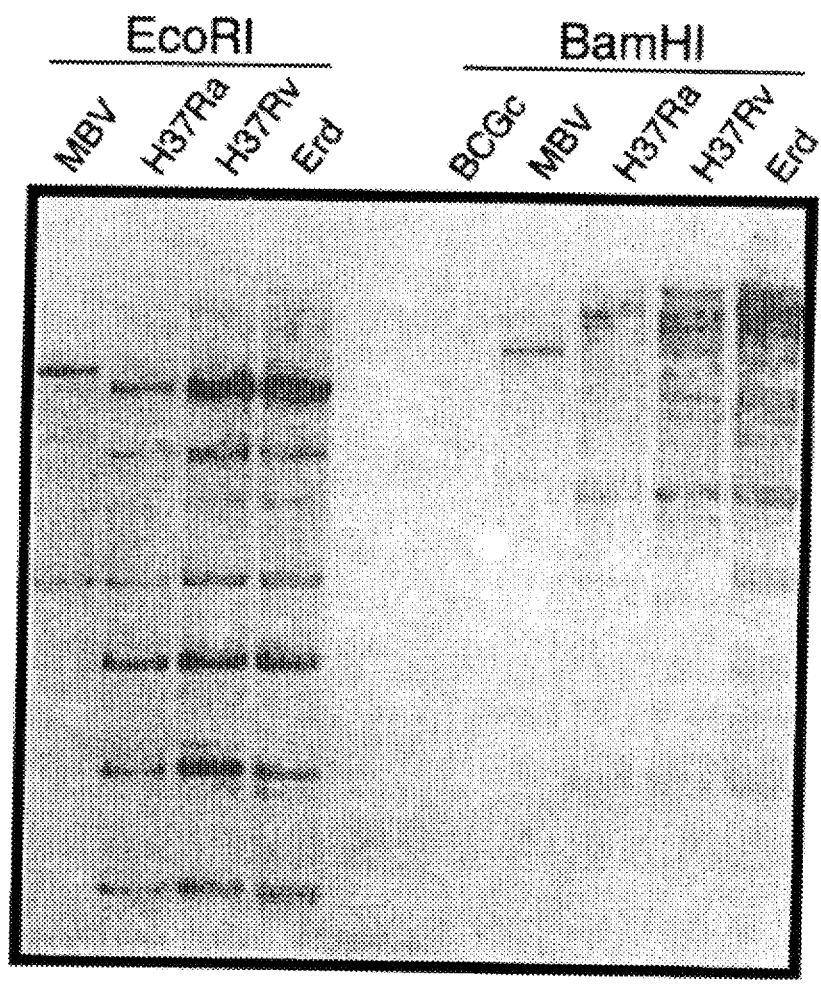
FIG. 8 shows EcoRI and BamHI restricted chromosomal DNAs from *Mycobacterium bovis*, BCG Connaught, and *Mycobacterium tuberculosis* strains H37Ra, H37Rv, and Erdman probed with $^{32}P$ labeled BCG subtracted probe.

The resulting Southern blot is illustrated in FIG. 8. The probe showed no labeling of BCG reflecting the presence of all three deletions, while the other strains were labeled.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. An isolated marker for an avirulent mycobacterium, said marker comprising a first nucleic acid that specifically hybridizes under stringent conditions with a second nucleic acid or a complement of said second nucleic acid where said second nucleic acid or complement of said second nucleic acid is selected from the group consisting of BCGΔ1a (SEQ ID NO: 1), BCGΔ1b (SEQ ID NO: 2), BCGΔ2a (SEQ ID NO: 3), BCGΔ2b (SEQ ID NO: 4), BCGΔ3a (SEQ ID NO: 5), BCGΔ3b (SEQ ID NO: 6), BCGΔ1ab (SEQ ID NO: 7), BCGΔ2ab (SEQ ID NO: 8), BCGΔ3ab (SEQ ID NO: 9), BCGΔ1 (between nucleotide 2327 and nucleotide 11126 of SEQ ID NO: 16), BCGΔ3 (between nucleotide 1406 and nucleotide 10673 of SEQ ID NO: 18), ORF 2B2 (nucleotides 3003-3590 of SEQ ID NO: 17), ORF 2C (nucleotides 5187-6134 of SEQ ID NO: 17), ORF 2D (nucleotides 6561-7217 of SEQ ID NO: 17), ORF 2E (nucleotides 8036-8560 of SEQ ID NO: 17), ORF 2F (nucleotide 9941-10909 of SEQ ID NO: 17), ORF 2H (nucleotides 11965-13407 of SEQ ID NO: 17), ORF 2I (nucleotides 13376-14221 of SEQ ID NO: 17), ORF 2J (nucleotides 7211-8259 of SEQ ID NO: 17), ORF 2K (nucleotides 4327-4992 of SEQ ID NO: 17), and ORF 2L (nucleotides 4521-5117 of SEQ ID NO: 17);

wherein said marker specifically hybridizes under stringent conditions to a nucleic acid from BCG, but not to a nucleic acid from *Mycobacterium tuberculosis* or *Mycobacterium bovis*, or where said marker specifically hybridizes under stringent conditions to a nucleic acid from *Mycobacterium tuberculosis* or *Mycobacterium bovis*, but not to a nucleic acid from BCG.

2. The marker of claim 1, wherein said marker comprises a subsequence of a nucleic acid where said nucleic acid is selected from the group consisting of BCGΔ1a (SEQ ID NO: 1), BCGΔ1b (SEQ ID NO: 2), BCGΔ2a (SEQ ID NO: 3), BCGΔ2b (SEQ ID NO: 4), BCGΔ3a (SEQ ID NO: 5), BCGΔ3b (SEQ ID NO: 6), BCGΔ1ab (SEQ ID NO: 7), BCGΔ2ab (SEQ ID NO: 8), BCGΔ3ab (SEQ ID NO: 9), BCGΔ1 (between nucleotide 2327 and nucleotide 11126 of SEQ ID NO: 16), BCGΔ3 (between nucleotide 1406 and nucleotide 10673 of SEQ ID NO: 18), ORF 2A (nucleotides 1829-2386 of SEQ ID NO: 17); ORF 2B1 (nucleotides 2862-4298 of SEQ ID NO: 17), ORF 2B2 (nucleotides 3003-3590 of SEQ ID NO: 17), ORF 2C (nucleotides 5197-6134 of SEQ ID NO: 17), ORF 2D (nucleotides 6561-7217 of SEQ ID NO: 17), ORF 2E (nucleotides 8036-8560 of SEQ ID NO: 17), ORF 2F (nucleotides 9941-10909 of SEQ ID NO: 17), ORF 2H (nucleotides 11965-13407 of SEQ ID NO: 17), ORF 2I (nucleotides 13376-14221 of SEQ ID NO: 17), ORF 2J (nucleotides 7211-8259 of SEQ ID NO: 17), ORF 2K (nucleotides 4327-4992 of SEQ ID NO: 17), and ORF 2L (nucleotides 4521-5117 of SEQ ID NO: 17).

3. The marker of claim 1, wherein said marker is selected from the group consisting of BCGΔ1a (SEQ ID NO: 1), BCGΔ1b (SEQ ID NO: 2), BCGΔ2a (SEQ ID NO: 3), BCGΔ2b (SEQ ID NO: 4), BCGΔ3a (SEQ ID NO: 5), BCGΔ3b (SEQ ID NO: 6), BCGΔ1ab (SEQ ID NO: 7), BCGΔ2ab (SEQ ID NO: 8), BCGΔ3ab (SEQ ID NO: 9), BCGΔ1 (between nucleotide 2327 and nucleotide 11126 of SEQ ID NO: 16), BCGΔ3 (between nucleotide 1406 and nucleotide 10673 of SEQ ID NO: 18), ORF 2A (nucleotides 1829-2386 of SEQ ID NO: 17); ORF 2B1 (nucleotides 2862-3298 of SEQ ID NO: 17), ORF 2B2 (nucleotides 3003-3590 of SEQ ID NO: 17), ORF 2C (nucleotides 5187-6134 of SEQ ID NO: 17), ORF 2D (nucleotides 6561-7217 of SEQ ID NO: 17), ORF 2E (nucleotides 8036-8560 of SEQ ID NO: 17), ORF 2F (nucleotides 9941-10909 of SEQ ID NO: 17), ORF 2H (nucleotides 11965-13407 of SEQ ID NO: 17), ORF 2I (nucleotides 13376-14221 of SEQ ID NO: 17), ORF 2J nucleotides 7211-8259 of SEQ ID NO: 17), ORF 2K (nucleotides 4327-4992 of SEQ ID NO: 17), and ORF 2L (nucleotides 4521-5117 of SEQ ID NO: 17).

4. The marker of claim 1, wherein said marker comprises a nucleic acid having at least 90 percent sequence identity with a sequence selected from the group consisting of BCGΔ1a (SEQ ID NO: 1), BCGΔ1b (SEQ ID NO: 2), BCGΔ2a (SEQ ID NO: 3), BCGΔ2b (SEQ ID NO: 4), BCGΔ3a (SEQ ID NO: 5), BCGΔ3b (SEQ ID NO: 6), BCGΔ1ab (SEQ ID NO: 7), BCGΔ2ab (SEQ ID NO: 8), BCGΔ3ab (SEQ ID NO: 9), BCGΔ1 (between nucleotide 2327 and nucleotide 11126 of SEQ ID NO: 16), BCGΔ3

(between nucleotide 1406 and nucleotide 10673 of SEQ ID NO: 18), ORF 2A (nucleotides 1829–2386 of SEQ ID NO: 17); ORF 2B1 (nucleotides 2862–3298 of SEQ ID NO: 17), ORF 2B2 (nucleotides 3003–3590 of SEQ ID NO: 17), ORF 2C (nucleotides 5187–6134 of SEQ ID NO: 17), ORF 2D (nucleotides 6561–7217 of SEQ ID NO: 17), ORF 2E (nucleotides 8036–8560 of SEQ ID NO: 17), ORF 2F (nucleotides 9941–10909 of SEQ ID NO: 17), ORF 2H (nucleotides 11965–13407 of SEQ ID NO: 17), ORF 2I (nucleotides 13376–14221 of SEQ ID NO: 17), ORF 2J (nucleotides 7211–8259 of SEQ ID NO: 17), ORF 2K (nucleotides 4327–4992 of SEQ ID NO: 17), and ORF 2L (nucleotides 4521–5117 of SEQ ID NO: 17).

5. The marker of claim 1, wherein said marker comprises a radioactive nucleotide probe.

6. The marker of claim 1, wherein said second nucleic acid or complement of said second nucleic acid is BCGΔ1.

7. The marker of claim 1, wherein said second nucleic acid or complement of said second nucleic acid is BCGΔ3.

8. The marker of claim 1, wherein said second nucleic acid or complement of said second nucleic acid is BCGΔ1a (SEQ ID NO: 1).

9. The marker of claim 1, wherein said second nucleic acid or complement of said second nucleic acid is BCGΔ1b (SEQ ID NO: 2).

10. The marker of claim 1, wherein said second nucleic acid or complement of said second nucleic acid is BCGΔ2a (SEQ ID NO: 3).

11. The marker of claim 1, wherein said second nucleic acid or complement of said second nucleic acid is BCGΔ2b (SEQ ID NO: 4).

12. The marker of claim 1, wherein said second nucleic acid or complement of said second nucleic acid is BCGΔ3a (SEQ ID NO: 5).

13. The marker of claim 1, wherein said second nucleic acid or complement of said second nucleic acid is BCGΔ3b (SEQ ID NO: 6).

14. The marker of claim 1, wherein said second nucleic acid or complement of said second nucleic acid is BCGΔ1ab (SEQ ID NO: 7).

15. The marker of claim 1, wherein said second nucleic acid or complement of said second nucleic acid is BCGΔ2ab (SEQ ID NO: 8).

16. The marker of claim 1, wherein said second nucleic acid or complement of said second nucleic acid is BCGΔ3ab (SEQ ID NO: 9).

17. The marker of claim 1, wherein said second nucleic acid or complement of said second nucleic acid is ORF 1A (nucleotides 889–2433 of SEQ ID NO: 16).

18. The marker of claim 1, wherein said second nucleic acid or complement of said second nucleic acid is ORF 1B (nucleotides 3130–4203 of SEQ ID NO: 16).

19. The marker of claim 1, wherein said second nucleic acid or complement of said second nucleic acid is ORF 1C (nucleotides 5075–6046 of SEQ ID NO: 16).

20. The marker of claim 1, wherein said second nucleic acid or complement of said second nucleic acid is ORF 1D (nucleotides 6954–8612 of SEQ ID NO: 16).

21. The marker of claim 1, wherein said second nucleic acid or complement of said second nucleic acid is ORF 1E (nucleotides 9663–10619 of SEQ ID NO: 16).

22. The marker of claim 1, wherein said second nucleic acid or complement of said second nucleic acid is ORF 1E (nucleotides 9663–10619 of SEQ ID NO: 16).

23. The marker of claim 1, wherein said second nucleic acid or complement of said second nucleic acid is ORF 2B2 (nucleotides 3003–3590 of SEQ ID NO: 17).

24. The marker of claim 1, wherein said second nucleic acid or complement of said second nucleic acid is ORF 2C (nucleotides 5187–6134 of SEQ ID NO: 17).

25. The marker of claim 1, wherein said second nucleic acid or complement of said second nucleic acid is ORF 2D (nucleotides 6561–7217 of SEQ ID NO: 17).

26. The marker of claim 1, wherein said second nucleic acid or complement of said second nucleic acid is ORF 2E (nucleotides 8036–8560 of SEQ ID NO: 17).

27. The marker of claim 1, wherein said second nucleic acid or complement of said second nucleic acid is ORF 2F (nucleotide 9941–10909 of SEQ ID NO: 17).

28. The marker of claim 1, wherein said second nucleic acid or complement of said second nucleic acid is ORF 2H (nucleotides 11965–13407 of SEQ ID NO: 17).

29. The marker of claim 1, wherein said second nucleic acid or complement of said second nucleic acid is ORF 2I (nucleotides 13376–14221 of SEQ ID NO: 17).

30. The marker of claim 1, wherein said second nucleic acid or complement of said second nucleic acid is ORF 2J (nucleotides 7211–8259 of SEQ ID NO: 17).

31. The marker of claim 1, wherein said second nucleic acid or complement of said second nucleic acid is ORF 2K (nucleotides 4327–4992 of SEQ ID NO: 17).

32. The marker of claim 1, wherein said second nucleic acid or complement of said second nucleic acid is ORF 2L (nucleotides 4521–5117 of SEQ ID NO: 17).

33. The marker of claim 1, wherein said second nucleic acid or complement of said second nucleic acid is ORF 3A (nucleotide 613–11755 of SEQ ID NO: 18).

34. The marker of claim 1, wherein said second nucleic acid or complement of said second nucleic acid is ORF 3B (nucleotide 1214–2560 of SEQ ID NO: 18).

35. The marker of claim 1, wherein said second nucleic acid or complement of said second nucleic acid is ORF 3C (nucleotide 2320–3332 of SEQ ID NO: 18).

36. The marker of claim 1, wherein said second nucleic acid or complement of said second nucleic acid is ORF 3D (nucleotide 4007–4930 of SEQ ID NO: 18).

37. The marker of claim 1, wherein said second nucleic acid or complement of said second nucleic acid is ORF 3E (nucleotide 4795–5337 of SEQ ID NO: 18).

38. The marker of claim 1, wherein said second nucleic acid or complement of said second nucleic acid is ORF 3F (nucleotide 5639–6214 of SEQ ID NO: 18).

39. The marker of claim 1 wherein said second nucleic acid or complement of said second nucleic acid is ORF 3G (nucleotide 7253–7762 of SEQ ID NO: 18).

40. The marker of claim 1, wherein said second nucleic acid or complement of said second nucleic acid is ORF 3H (nucleotide 7868–9197 of SEQ ID NO: 18).

41. The marker of claim 1, wherein said second nucleic acid or complement of said second nucleic acid is ORF 3I (nucleotide 10146–11810 of SEQ ID NO: 18).

42. The marker of claim 1, wherein said second nucleic acid or complement of said second nucleic acid is ORF 3K (nucleotide 10893–11594 of SEQ ID NO: 18).

43. The marker of claim 1, wherein said second nucleic acid or complement of said second nucleic acid is ORF 3L (nucleotide 9488–10147 of SEQ ID NO: 18).

44. A recombinant cell transfected with a first nucleic acid wherein said first nucleic acid hybridizes under stringent conditions with a second nucleic acid or a complement of said second nucleic acid where said second nucleic acid or complement of said second nucleic acid is selected from the group consisting of BCGΔ1a (SEQ ID NO: 1), BCGΔ1b (SEQ ID NO: 2), BCGΔ2a (SEQ ID NO: 3), BCGΔ2b (SEQ ID NO: 4), BCGΔ3a (SEQ ID NO: 5), BCGΔ3b (SEQ ID NO: 6), BCGΔ1ab (SEQ ID NO: 7), BCGΔ2ab (SEQ ID NO: 8), BCGΔ3ab (SEQ ID NO: 9), BCGΔ1 (between nucleotide 2327 and nucleotide 11126 of SEQ ID NO: 16), BCGΔ3 (between nucleotide 1406 and nucleotide 10673 of SEQ ID NO: 18), ORF 2B2 (nucleotides 3003-3590 of SEQ ID NO: 17), ORF 2C (nucleotides 5187-6134 of SEQ ID NO: 17), ORF 2D (nucleotides 6561-7217 of SEQ ID NO: 17), ORF 2E (nucleotides 8036-8560 of SEQ ID NO: 17), ORF 2F (nucleotide 9941-10909 of SEQ ID NO: 17), ORF 2H (nucleotides 11965-13407 of SEQ ID NO: 17), ORF 2I (nucleotides 13376-1422 of SEQ ID NO: 17), ORF 2J (nucleotides 7211-8253 of SEQ ID NO: 17), ORF 2K (nucleotides 4327-4992 of SEQ ID NO: 17), and ORF 2L (nucleotides 4521 . 5117 of SEQ ID NO: 17).

45. The recombinant cell of claim 44, wherein the cell is a Mycobacterium.

46. The cell of claim 44, wherein the cell expresses a polypeptide encoded by an intact open reading frame selected from the group consisting of an open reading frame from BCGΔ1 or BCGΔ3.

47. The cell of claim 44, wherein said cell is a mycobacterium having one or more deletions in the genomic regions selected from the group consisting of BCGΔ1 (between nucleotide 2327 and nucleotide 11126 of SEQ ID NO: 16), BCGΔ3 (between nucleotide 1406 and nucleotide 10673 of SEQ ID NO: 18), ORF 2B2 (nucleotides 3003-3590 of SEQ ID NO: 17), ORF 2C (nucleotides 5187-6134 of SEQ ID NO: 17), ORF 2D (nucleotides 6561-7217 of SEQ ID NO: 17), ORF 2E (nucleotides 8036-8560 of SEQ ID NO: 17), ORF 2F (nucleotide 9941-10909 of SEQ ID NO: 17), ORF 2H (nucleotides 11965-13407 of SEQ ID NO: 17), ORF 2I (nucleotides 13376-14221 of SEQ ID NO: 17), ORF 2J (nucleotides 7211-8259 of SEQ ID NO: 17), ORF 2K (nucleotides 4327-4992 of SEQ ID NO: 17), and ORF 2L (nucleotides 4521-5117 of SEQ ID NO: 17); wherein said deletions result in the attenuation of an otherwise virulent strain of mycobacterium and wherein said deletions are present in up to two of said regions.

48. The cell of claim 47, whereto said deletions comprise a deletion selected from the group consisting of BCGΔ1, and BCGΔ3.

49. The cell of claim 44, wherein said second nucleic acid or complement of said second nucleic acid is BCGΔb 1a (SEQ ID NO: 1).

50. The cell of claim 44, wherein said second nucleic acid or complement of said second nucleic acid is BCGΔ1b (SEQ ID NO: 2).

51. The cell of claim 44, wherein said second nucleic acid or complement of said second nucleic acid is BCGΔ2a (SEQ ID NO: 3).

52. The cell of claim 44, wherein said second nucleic acid or complement of said second nucleic acid is BCGΔ2b (SEQ ID NO: 4).

53. The cell of claim 44, wherein said second nucleic acid or complement of said second nucleic acid is BCGΔ3a (SEQ ID NO: 5).

54. The cell of claim 44, wherein said second nucleic acid or complement of said second nucleic acid is BCGΔ3b (SEQ ID NO: 6).

55. The cell of claim 44, wherein said second nucleic acid or complement of said second nucleic acid is BCGΔ1ab (SEQ ID NO: 7).

56. The cell of claim 44, wherein said second nucleic acid or complement of said second nucleic acid is BCGΔ2ab (SEQ ID NO: 8).

57. The cell of claim 44, wherein said second nucleic acid or complement of said second nucleic acid is BCGΔ3ab (SEQ ID NO: 9).

* * * * *

UNITED STATES PATENT AND TRADEMARK OFFICE
CERTIFICATE OF CORRECTION

PATENT NO. : 5,700,683
DATED : December 23, 1997
INVENTOR(S) : Charles K. Stover, et. al.

It is certified that error appears in the above-identified patent and that said Letters Patent is hereby corrected as shown below:

Column 6, line 32, delete "an" and insert therefor --art--.
Column 10, line 11, delete "BCG-△1" and insert therefor --BCG△1--.
Column 10, line 45, delete "TALBE" and insert therefor --TABLE--.
Column 10, line 53, Seq. ID 4, delete
"gcccacccggtcgagcaccc|CGATGATCTFCTGTTTGACC" and insert therefor --
gcccacccggtcgagcaccc|CGATGATCTTCTGTTTGACC--.
Column 12, line 42, delete "et al," and insert therefor --et al.,--.

Column 73, line 16 (Claim 6), delete "market" and insert --marker--.
Column 74, line 36 (Claim 35), delete "2320" and insert --2820--.
Column 75, line 12 (Claim 44), delete "1422 and insert --1421--.
Column 75, line 13 (Claim 44), delete "8253" and insert --8259--.
Column 75, line 15 (Claim 44), delete "4521 5117" and insert --4521-5117--.

Signed and Sealed this

Ninth Day of March, 1999

Attest:

Attesting Officer

Q. TODD DICKINSON

Acting Commissioner of Patents and Trademarks

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

CTGGTCGACG ATTGGCACAT GCAGCCGTGG GTGCCGCCGG    40

( 2 ) INFORMATION FOR SEQ ID NO:2:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GTGTCTTCAT CGGCTTCCAC CCAGCCGCCC GGATCCAGCA    40

( 2 ) INFORMATION FOR SEQ ID NO:3:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

CAACTCCACG GCGACCACCC GCGCCCCCGC TCGCACTAGA                                40

( 2 ) INFORMATION FOR SEQ ID NO:4:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

GCCCACCCGG TCGAGCACCC CGATGATCTT CTGTTTGACC                                40

( 2 ) INFORMATION FOR SEQ ID NO:5:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

CACCTCGACC ACGGCCAACC GTGGACCTGT GAGATACACT                                40

( 2 ) INFORMATION FOR SEQ ID NO:6:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

TCAGCAGTCC ACGGCCAACC CCGCACCAAC ACCTTCCACC                                40

( 2 ) INFORMATION FOR SEQ ID NO:7:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

CTGGTCGACG ATTGGCACAT CCAGCCGCCC GGATCCAGCA                                40

( 2 ) INFORMATION FOR SEQ ID NO:8:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

CAACTCCACG GCGACCACCC CGATGATCTT CTGTTTGACC                                40

( 2 ) INFORMATION FOR SEQ ID NO:9:

( i ) SEQUENCE CHARACTERISTICS:
   ( A ) LENGTH: 40 base pairs
   ( B ) TYPE: nucleic acid
   ( C ) STRANDEDNESS: single
   ( D ) TOPOLOGY: linear ( i i ) MOLECULE TYPE: DNA (genomic)

( x i ) SEQUENCE DESCRIPTION: SEQ ID NO:9:

CACCTCGACC ACGGCCAACC CCGCACCAAC ACCTTCCACC    40

( 2 ) INFORMATION FOR SEQ ID NO:10:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:10:

TCGACGATTG GCACAT    16

( 2 ) INFORMATION FOR SEQ ID NO:11:

( i ) SEQUENCE CHARACTERISTICS:
      ( A ) LENGTH: 19 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:11:

TCCCTCCCTG TATTTGTAT    19

( 2 ) INFORMATION FOR SEQ ID NO:12:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:12:

CGTTCTTCGG AGGTTTC    17

( 2 ) INFORMATION FOR SEQ ID NO:13:

( i ) SEQUENCE CHARACTERISTICS:
      ( A ) LENGTH: 14 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:13:

GGCGGCTGGG TGGA    14

( 2 ) INFORMATION FOR SEQ ID NO:14:

( i ) SEQUENCE CHARACTERISTICS:
      ( A ) LENGTH: 24 base pairs
      ( B ) TYPE: nucleic acid
      ( C ) STRANDEDNESS: single ( D ) TOPOLOGY: linear ( i i ) MOLECULE TYPE: DNA (genomic)

( x i ) SEQUENCE DESCRIPTION: SEQ ID NO:14:

GACACTCTCG AGACATCACC GTCC 24

( 2 ) INFORMATION FOR SEQ ID NO:15:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:15:

GATCGGACGG TGATGTCTCG AGAGTG 26

( 2 ) INFORMATION FOR SEQ ID NO:16:

( i ) SEQUENCE CHARACTERISTICS:
    ( A ) LENGTH: 16885 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:16:

```
GAATTCCTGC GCACCCTGAT CCTGTCGCTG GTGGCAATGA CTCATCCAGA TCAGGTGAAT     60
CTCCTGCTCA CCGACTTCAA AGGTGGTTCA ACCTTCCTGG GAATGGAAAA GCTTCCGCAC    120
ACTGCCGCTG TCGTCACCAA CATGGCCGAG GAAGCCGAGC TCGTCAGCCG GATGGGCGAG    180
GTGTTGACCG GAGAACTCGA TCGGCGCCAG TCGATCCTCC GACAGGCCGG GATGAAAGTC    240
GGCGCGGCCG GAGCCCTGTC CGGCGTGGCC GAATACGAGA AGTACCGCGA ACGCGGTGCC    300
GACCTACCCC CGCTGCCAAC GCTTTTCGTC GTCGTCGACG AGTTCGCCGA GCTGTTGCAG    360
AGTCACCCGG ACTTCATCGG GCTGTTCGAC CGGATCTGCC GCGTCGGGCG GTCGCTGAGG    420
GTCCATCTGC TGCTGGCTAC CCAGTCGCTG CAGACCGGCG GTGTTCGCAT CGACAAACTG    480
GAGCCAAACC TGACATATCG AATCGCATTG CGCACCACCA GCTCTCATGA ATCCAAGGCG    540
GTAATCGGCA CACCGGAGGC GCAGTACATC ACCAACAAGG AGAGCGGTGT CGGGTTTCTC    600
CGGGTCGGCA TGGAAGACCC GGTCAAGTTC AGCACCTTCT ACATCAGTGG GCCATACATG    660
CCGCCGGCGG CAGGCGTCGA AACCAATGGT GAAGCCGGAG GGCCCGGTCA ACAGACCACT    720
AGACAAGCCG CGCGCATTCA CAGGTTCACC GCGGCACCGG TTCTCGAGGA GGCGCCGACA    780
CCGTGACCCG CGCCGGCGAC GATGCAAAGC GCAGCGATGA GGAGGAGCGG CGCCAACGGC    840
CCGCGCCGGC GACGATGCAA AGCGCAGCGA TGAGGAGGAG CGGCGCGCAT GACTGCTGAA    900
CCGGAAGTAC GGACGCTGCG CGAGGTTGTG CTGGACCAGC TCGGCACTGC TGAATCGCGT    960
GCGTACAAGA TGTGGCTGCC GCCGTTGACC AATCCGGTCC GCTCAACGA GCTCATCGCC   1020
CGTGATCGGC GACAACCCCT GCGATTGCC CTGGGATCA TGGATGAACC GCGCCGCCAT   1080
CTACAGGATG TGTGGGGCGT AGACGTTTCC GGGGCCGGCG GCAACATCGG TATTGGGGGC   1140
GCACCTCAAA CCGGGAAGTC GACGCTACTG CAGACGATGG TGATGTCGGC CGCCGCCACA   1200
CACTCACCGC GCAACGTTCA GTTCTATTGC ATCGACCTAG GTGGCGGCGG GCTGATCTAT   1260
CTCGAAAACC TTCCACACGT CGGTGGGGTA GCCAATCGGT CCGAGCCCGA CAAGGTCAAC   1320
```

```
CGGGTGGTCG CAGAGATGCA AGCCGTCATG CGGCAACGGG AAACCACCTT CAAGGAACAC    1380
CGAGTGGGCT CGATCGGGAT GTACCGGCAG CTGCGTGACG ATCCAAGTCA ACCCGTTGCG    1440
TCCGATCCAT ACGGCGACGT CTTTCTGATC ATCGACGGAT GGCCCGGTTT TGTCGGCGAG    1500
TTCCCCGACC TTGAGGGGCA GGTTCAAGAT CTGGCCGCCC AGGGGCTGGG GTTCGGCGTC    1560
CACGTCATCA TCTCCACGCC ACGCTGGACA GAGCTGAAGT CGCGTGTTCG CGACTACCTC    1620
GGCACCAAGA TCGAGTTCCG GCTTGGTGAC GTCAATGAAA CCCAGATCGA CCGGATTACC    1680
CGCGAGATCC CGGCGAATCG TCCGGGTCGG GCAGTGTCGA TGGAAAAGCA CCATCTGATG    1740
ATCGGCGTGC CCAGGTTCGA CGGCGTGCAC AGCGCCGATA ACCTGGTGGA GGCGATCACC    1800
GCGGGGGTGA CGCAGATCGC TTCCCAGCAC ACCGAACAGG CACCTCCGGT GCGGGTCCTG    1860
CCGGAGCGTA TCCACCTGCA CGAACTCGAC CCGAACCCGC CGGGACCAGA GTCCGACTAC    1920
CGCACTCGCT GGGAGATTCC GATCGGCTTG CGCGAGACGG ACCTGACGCC GGCTCACTGC    1980
CACATGCACA CGAACCCGCA CCTACTGATC TTCGGTGCGG CCAAATCGGC CAAGACGACC    2040
ATTGCCCACG CGATCGCGCG CGCCATTTGT GCCCGAAACA GTCCCCAGCA GGTGCGGTTC    2100
ATGCTCGCGG ACTACCGCTC GGGCCTGCTG GACGCGGTGC CGGACACCCA TCTGCTGGGC    2160
GCCGGCGCGA TCAACCGCAA CAGCGCGTCG CTAGACGAGG CCGCTCAAGC ACTGGCGGTC    2220
AACCTGAAGA AGCGGTTGCC GCCGACCGAC CTGACGACGG CGCAGCTACG CTCGCGTTCG    2280
TGGTGGAGCG GATTTGACGT CGTGCTTCTG GTCGACGATT GGCACATGCA GCCGTGGGTG    2340
CCGCCGGGGG GATGCCGCCG ATGGCACCGC TGGCCCCGTT ATTGCCGGCG GCGGCAGATA    2400
TCGGGTTGCA CATCATTGTC ACCTGTCAGA TGAGCCAGGC TTACAAGGCA ACCATGGACA    2460
AGTTCGTCGG CGCCGCATTC GGGTCGGGCG CTCCGACAAT GTTCCTTTCG GGCGAGAAGC    2520
AGGAATTCCC ATCCAGTGAG TTCAAGGTCA AGCGGCGCCC CCTGGCCAG GCATTTCTCG    2580
TCTCGCCAGA CGGCAAAGAG GTCATCCAGG CCCCCTACAT CGAGCCTCCA GAAGAAGTGT    2640
TCGCAGCACC CCCAAGCGCC GGTTAAGATT ATTTCATTGC CGGTGTAGCA GGACCCGAGC    2700
TCAGCCCGGT AATCGAGTTC GGGCAATGCT GACCATCGGG TTTGTTTCCG GCTATAACCG    2760
AACGGTTTGT GTACGGGATA CAAATACAGG GAGGGAAGAA GTAGGCAAAT GGAAAAAATG    2820
TCACATGATC CGATCGCTGC CGACATTGGC ACGCAAGTGA GCGACAACGC TCTGCACGGC    2880
GTGACGGCCG GCTCGACGGC GCTGACGTCG GTGACCGGGC TGGTTCCCGC GGGGGCCGAT    2940
GAGGTCTCCG CCCAAGCGGC GACGGCGTTC ACATCGGAGG GCATCCAATT GCTGGCTTCC    3000
AATGCATCGG CCCAAGACCA GCTCCACCGT GCGGGCGAAG CGGTCCAGGA CGTCGCCCGC    3060
ACCTATTCGC AAATCGACGA CGGCGCCGCC GGCGTCTTCG CCTAATAGGC CCCCAACACA    3120
TCGGAGGGAG TGATCACCAT GCTGTGGCAC GCAATGCCAC CGGAGCTAAA TACCGCACGG    3180
CTGATGGCCG GCGCGGGTCC GGCTCCAATG CTTGCGGCGG CCGCGGGATG GCAGACGCTT    3240
TCGGCGGCTC TGGACGCTCA GGCCGTCGAG TTGACCGCGC GCCTGAACTC TCTGGGAGAA    3300
GCCTGGACTG GAGGTGGCAG CGACAAGGCG CTTGCGGCTG CAACGCCGAT GGTGGTCTGG    3360
CTACAAACCG CGTCAACACA GGCCAAGACC CGTGCGATGC AGGCGACGGC GCAAGCCGCG    3420
GCATACACCC AGGCCATGGC CACGACGCCG TCGCTGCCGG AGATCGCCGC CAACCACATC    3480
ACCCAGGCCG TCCTTACGGC CACCAACTTC TTCGGTATCA ACACGATCCC GATCGCGTTG    3540
ACCGAGATGG ATTATTTCAT CCGTATGTGG AACCAGGCAG CCCTGGCAAT GGAGGTCTAC    3600
CAGGCCGAGA CCGCGGTTAA CACGCTTTTC GAGAAGCTCG AGCCGATGGC GTCGATCCTT    3660
GATCCCGGCG CGAGCCAGAG CACGACGAAC CCGATCTTCG GAATGCCCTC CCCTGGCAGC    3720
```

```
TCAACACCGG  TTGGCCAGTT  GCCGCCGGCG  GCTACCCAGA  CCCTCGGCCA  ACTGGGTGAG  3780
ATGAGCGGCC  CGATGCAGCA  GCTGACCCAG  CCGCTGCAGC  AGGTGACGTC  GTTGTTCAGC  3840
CAGGTGGGCG  GCACCGGCGG  CGGCAACCCA  GCCGACGAGG  AAGCCGCGCA  GATGGGCCTG  3900
CTCGGCACCA  GTCCGCTGTC  GAACCATCCG  CTGGCTGGTG  GATCAGGCCC  CAGCGCGGGC  3960
GCGGGCCTGC  TGCGCGCGGA  GTCGCTACCT  GGCGCAGGTG  GGTCGTTGAC  CCGCACGCCG  4020
CTGATGTCTC  AGCTGATCGA  AAAGCCGGTT  TGCCCCCTCG  GTGATGCCGG  CGGCTGCTGC  4080
CGGATCGTCG  GCGACGGGTG  GCGCCGCTCC  GGTGGGTGCG  GGAGCGATGG  GCCAGGGTGC  4140
GCAATCCGGC  GGCTCCACCA  GGCCGGGTCT  GGTCGCGCCG  GCACCGCTCG  CGCAGGAGCG  4200
TGAAGAAGAC  GACGAGGACG  ACTGGGACGA  AGAGGACGAC  TGGTGAGCTC  CCGTAATGAC  4260
AACAGACTTC  CCGGCCACCC  GGGCCGGAAG  ACTTGCCAAC  ATTTTGGCGA  GGAAGGTAAA  4320
GAGAGAAAGT  AGTCCAGCAT  GGCAGAGATG  AAGACCGATG  CCGCTACCCT  CGCGCAGGAG  4380
GCAGGTAATT  TCGAGCGGAT  CTCCGGCGAC  CTGAAAACCC  AGATCGACCA  GGTGGAGTCG  4440
ACGGCAGGTT  CGTTGCAGGG  CCAGTGGCGC  GGCGCGGCGG  GGACGGCCGC  CAGGCCGCG  4500
GTGGTGCGCT  TCCAAGAAGC  AGCCAATAAG  CAGAAGCAGG  AACTCGACGA  GATCTCGACG  4560
AATATTCGTC  AGGCCGGCGT  CCAATACTCG  AGGGCCGACG  AGGAGCAGCA  GCAGGCGCTG  4620
TCCTCGCAAA  TGGGCTTCTG  ACCCGCTAAT  ACGAAAGAA   ACGGAGCAAA  AACATGACAG  4680
AGCAGCAGTG  GAATTTCGCG  GGTATCGAGG  CCGCGGCAAG  CGCAATCCAG  GGAAATGTCA  4740
CGTCCATTCA  TTCCCTCCTT  GACGAGGGGA  AGCAGTCCCT  GACCAAGCTC  GCAGCGGCCT  4800
GGGGCGGTAG  CGGTTCGGAG  GCGTACCAGG  GTGTCCAGCA  AAAATGGGAC  GCCACGGCTA  4860
CCGAGCTGAA  CAACGCGCTG  CAGAACCTGG  CGCGGACGAT  CAGCGAAGCC  GGTCAGGCAA  4920
TGGCTTCGAC  CGAAGGCAAC  GTCACTGGGA  TGTTCGCATA  GGGCAACGCC  GAGTTCGCGT  4980
AGAATAGCGA  AACACGGGAT  CGGGCGAGTT  CGACCTTCCG  TCGGTCTCGC  CCTTTCTCGT  5040
GTTTATACGT  TTGAGCGCAC  TCTGAGAGGT  TGTCATGGCG  GCCGACTACG  ACAAGCTCTT  5100
CCGGCCGCAC  GAAGGTATGG  AAGCTCCGGA  CGATATGGCA  GCGCAGCCGT  TCTTCGACCC  5160
CAGTGCTTCG  TTTCGCCGG   CGCCCGCATC  GGCAAACCTA  CCGAAGCCCA  ACGGCCAGAC  5220
TCCGCCCCCG  ACGTCCGACG  ACCTGTCGGA  GCGGTTCGTG  TCGGCCCCGC  CGCCGCCACC  5280
CCCACCCCCA  CCTCCGCCTC  CGCCAACTCC  GATGCCGATC  GCCGCAGGAG  AGCCGCCCTC  5340
GCCGGAACCG  GCCGCATCTA  AACCACCCAC  ACCCCCCATG  CCCATCGCCG  GACCCGAACC  5400
GGCCCCACCC  AAACCACCCA  CACCCCCCAT  GCCCATCGCC  GGACCCGAAC  CGGCCCCACC  5460
CAAACCACCC  ACACCTCCGA  TGCCCATCGC  CGGACCTGCA  CCCACCCCAA  CCGAATCCCA  5520
GTTGGCGCCC  CCCAGACCAC  CGACACCACA  AACGCCAACC  GGAGCGCCGC  AGCAACCGGA  5580
ATCACCGGCG  CCCCACGTAC  CCTCGCACGG  GCCACATCAA  CCCCGGCGCA  CCGCACCAGC  5640
ACCGCCCTGG  GCAAAGATGC  CAATCGGCGA  ACCCCGCCC   GCTCCGTCCA  GACCGTCTGC  5700
GTCCCGGCC   GAACCACCGA  CCCGGCCTGC  CCCCAACAC   TCCGACGTG   CGCGCCGGGG  5760
TCACCGCTAT  CGCACAGACA  CCGAACGAAA  CGTCGGGAAG  GTAGCAACTG  GTCCATCCAT  5820
CCAGGCGCGG  CTGCGGGCAG  AGGAAGCATC  CGGCGCGCAG  CTCGCCCCCG  GAACGGAGCC  5880
CTCGCCAGCG  CCGTTGGGCC  AACCGAGATC  GTATCTGGCT  CCGCCCACCC  GCCCGCGCC   5940
GACAGAACCT  CCCCCAGCC   CCTCGCCGCA  GCGCAACTCC  GGTCGGCGTG  CCGAGCGACG  6000
CGTCCGACCC  CGATTTAGCC  GCCCAACATG  CCGCGGCGCA  ACCTGATTCA  ATTACGGCCG  6060
CAACCCACTG  GCGGTCGTCG  CCGCAAGCGT  GCAGCGCCGG  GATGCTCGAC  GCGACACAAG  6120
```

| | | | | | |
|---|---|---|---|---|---|
| AAATCCTTAA | GGCCGGCGGC | CAAGGGGCCG | AAGGTGAAGA | AGGTGAAGCC | CCAGAAACCG | 6180 |
| AAGGCCACGA | AGCCGCCCAA | AGTGGTGTCG | CAGCGCGGCT | GGCGACATTG | GGTGCATGCG | 6240 |
| TTGACGCGAA | TCAACCTGGG | CCTGTCACCC | GACGAGAAGT | ACGAGCTGGA | CCTGCACGCT | 6300 |
| CGAGTCCGCC | GCAATCCCCG | CGGGTCGTAT | CAGATCGCCG | TCGTCGGTCT | CAAAGGTGGG | 6360 |
| GCTGGCAAAA | CCACGCTGAC | AGCAGCGTTG | GGGTCGACGT | TGGCTCAGGT | GCGGCCGAC | 6420 |
| CGGATCCTGG | CTCTAGACGC | GGATCCAGGC | GCCGGAAACC | TCGCCGATCG | GGTAGGGCGA | 6480 |
| CAATCGGGCG | CGACCATCGC | TGATGTGCTT | GCAGAAAAAG | AGCTGTCGCA | CTACAACGAC | 6540 |
| ATCCGCGCAC | ACACTAGCGT | CAATGCGGTC | AATCTGGAAG | TGCTGCCGGC | ACCGGAATAC | 6600 |
| AGCTCGGCGC | AGCGCGCGCT | CAGCGACGCC | GACTGGCATT | TCATCGCCGA | TCCTGCGTCG | 6660 |
| AGGTTTTACA | ACCTCGTCTT | GGCTGATTGT | GGGGCCGGCT | TCTTCGACCC | GCTGACCCGC | 6720 |
| GGCGTGCTGT | CCACGGTGTC | CGGTGTCGTG | GTCGTGGCAA | GTGTCTCAAT | CGACGGCGCA | 6780 |
| CAACAGGCGT | CGGTCGCGTT | GGACTGGTTG | CGCAACAACG | GTTACCAAGA | TTTGGCGAGC | 6840 |
| CGCGCATGCG | TGGTCATCAA | TCACATCATG | CCGGGAGAAC | CCAATGTCGC | AGTTAAAGAC | 6900 |
| CTGGTGCGGC | ATTTCGAACA | GCAAGTTCAA | CCCGGCCGGG | TCGTGGTCAT | GCCGTGGGAC | 6960 |
| AGGCACATTG | CGGCCGGAAC | CGAGATTTCA | CTCGACTTGC | TCGACCCTAT | CTACAAGCGC | 7020 |
| AAGGTCCTCG | AATTGGCCGC | AGCGCTATCC | GACGATTTCG | AGAGGGCTGG | ACGTCGTTGA | 7080 |
| GCGCACCTGC | TGTTGCTGCT | GGTCCTACCG | CCGCGGGGGC | AACCGCTGCG | CGGCCTGCCA | 7140 |
| CCACCCGGGT | GACGATCCTG | ACCGGCAGAC | GGATGACCGA | TTTGGTACTG | CCAGCGGCGG | 7200 |
| TGCCGATGGA | AACTTATATT | GACGACACCG | TCGCGGTGCT | TTCCGAGGTG | TTGGAAGACA | 7260 |
| CGCCGGCTGA | TGTACTCGGC | GGCTTCGACT | TTACCGCGCA | AGGCGTGTGG | GCGTTCGCTC | 7320 |
| GTCCCGGATC | GCCGCCGCTG | AAGCTCGACC | AGTCACTCGA | TGACGCCGGG | GTGGTCGACG | 7380 |
| GGTCACTGCT | GACTCTGGTG | TCAGTCAGTC | GCACCGAGCG | CTACCGACCG | TTGGTCGAGG | 7440 |
| ATGTCATCGA | CGCGATCGCC | GTGCTTGACG | AGTCACCTGA | GTTCGACCGC | ACGGCATTGA | 7500 |
| ATCGCTTTGT | GGGGGCGGCG | ATCCCGCTTT | TGACCGCGCC | CGTCATCGGG | ATGGCGATGC | 7560 |
| GGGCGTGGTG | GGAAACTGGG | CGTAGCTTGT | GGTGGCCGTT | GGCGATTGGC | ATCCTGGGGA | 7620 |
| TCGCTGTGCT | GGTAGGCAGC | TTCGTCGCGA | ACAGGTTCTA | CCAGAGCGGC | CACCTGGCCG | 7680 |
| AGTGCCTACT | GGTCACGACG | TATCTGCTGA | TCGCAACCGC | CGCAGCGCTG | GCCGTGCCGT | 7740 |
| TGCCGCGCGG | GGTCAACTCG | TTGGGGGCGC | CACAAGTTGC | CGGCGCCGCT | ACGGCCGTGC | 7800 |
| TGTTTTTGAC | CTTGATGACG | CGGGGCGGCC | CTCGGAAGCG | TCATGAGTTG | GCGTCGTTTG | 7860 |
| CCGTGATCAC | CGCTATCGCG | GTCATCGCGG | CCGCCGCTGC | CTTCGGCTAT | GGATACCAGG | 7920 |
| ACTGGGTCCC | CGCGGGGGGG | ATCGCATTCG | GGCTGTTCAT | TGTGACGAAT | GCGGCCAAGC | 7980 |
| TGACCGTCGC | GGTCGCGCGG | ATCGCGCTGC | CGCCGATTCC | GGTACCCGGC | GAAACCGTGG | 8040 |
| ACAACGAGGA | GTTGCTCGAT | CCCGTCGCGA | CCCCGGAGGC | TACCAGCGAA | GAAACCCCGA | 8100 |
| CCTGGCAGGC | CATCATCGCG | TCGGTGCCCG | CGTCCGCGGT | CCGGCTCACC | GAGCGCAGCA | 8160 |
| AACTGGCCAA | GCAACTTCTC | ATCGGATACG | TCACGTCGGG | CACCCTGATT | CTGGCTGCCG | 8220 |
| GTGCCATCGC | GGTCGTGGTG | CGCGGCACT | TCTTTGTACA | CAGCCTGGTG | GTCGCGGGTT | 8280 |
| TGATCACGAC | CGTCTGCGGA | TTTCGCTCGC | GGCTTACGC | CGAGCGCTGG | TGTGCGTGGG | 8340 |
| CGTTGCTGGC | GGCGACGGTC | GCGATTCCGA | CGGGTCTGAC | GGCCAAACTC | ATCATCTGGT | 8400 |
| ACCCGCACTA | TGCCTGGCTG | TTGTTGAGCG | TCTACCTCAC | GGTAGCCCTG | GTTGCGCTCG | 8460 |
| TGGTGGTCGG | GTCGATGGCT | CACGTCCGGC | GCGTTTCACC | GGTCGTAAAA | CGAACTCTGG | 8520 |

```
AATTGATCGA CGGCGCCATG ATCGCTGCCA TCATTCCCAT GCTGCTGTGG ATCACCGGGG   8580
TGTACGACAC GGTCCGCAAT ATCCGGTTCT GAGCCGGATC GGCTGATTGG CGGTTCCTGA   8640
CAGAACATCG AGGACACGGC GCAGGTTTGC ATACCTTCGG CGCCCGACAA ATTGCTGCGA   8700
TTGAGCGTGT GGCGCGTCCG GTAAATTTG  CTCGATGGGG AACACGTATA GGAGATCCGG   8760
CAATGGCTGA ACCGTTGGCC GTCGATCCCA CCGGCTTGAG CGCAGCGGCC GCGAAATTGG   8820
CCGGCCTCGT TTTTCCGCAG CCTCCGGCGC CGATCGCGGT CAGCGGAACG GATTCGGTGG   8880
TAGCAGCAAT CAACAAGACC ATGCCAAGCA TCGAATCGCT GGTCAGTGAC GGGCTGCCCG   8940
GCGTGAAAGC CGCCCTGACT CGAACAGCAT CCAACATGAA CGCGGCGGCG GACGTCTATG   9000
CGAAGACCGA TCAGTCACTG GGAACCAGTT TGAGCCAGTA TGCATTCGGC TCGTCGGGCG   9060
AAGGCCTGGC TGGCGTCGCC TCGGTCGGTG GTCAGCCAAG TCAGGCTACC CAGCTGCTGA   9120
GCACACCCGT GTCACAGGTC ACGACCCAGC TCGGCGAGAC GGCCGCTGAG CTGGCACCCC   9180
GTGTTGTTGC GACGGTGCCG CAACTCGTTC AGCTGGCTCC GCACGCCGTT CAGATGTCGC   9240
AAAACGCATC CCCCATCGCT CAGACGATCA GTCAAACCGC CAACAGGCC  GCCCAGAGCG   9300
CGCAGGGCGG CAGCGGCCCA ATGCCCGCAC AGCTTGCCAG CGCTGAAAAA CCGGCCACCG   9360
AGCAAGCGGA GCCGGTCCAC GAAGTGACAA ACGACGATCA GGGCGACCAG GGCGACGTGC   9420
AGCCGGCCGA GGTCGTTGCC GCGGCACGTG ACGAAGGCGC CGGCGCATCA CCGGGCCAGC   9480
AGCCCGGCGG AGGCGTTCCC GCGCAAGCCA TGGATACCGG AGCCGGTGCC CGCCCAGCGG   9540
CGAGTCCGCT GGCGGCCCCC GTCGATCCGT CGACTCCGGC ACCCTCAACA ACCACAACGT   9600
TGTAGACCGG GCCTGCCAGC GGCTCCGTCT CGCACGCAGC GCCTGTTGCT GTCCTGGCCT   9660
CGTCAGGATG CGGCGGCCAG GGCCCGGTCG AGCAACCCGG TGACGTATTG CCAGTACAGC   9720
CAGTCCGCGA CGGCCACACG CTGGACGGCC GCGTCAGTCG CAGTGTGCGC TTGGTGCAGG   9780
GCAATCTCCT GTGAGTGGGC AGCGTAGGCC CGGAACGCCC GCAGATGAGC GGCCTCGCGG   9840
CCGGTAGCGG TGCTGGTCAT GGGCTTCATC AGCTCGAACC ACAGCATGTG CCGCTCATCG   9900
CCCGGTGGAT TGACATCCAC CGGCGCCGGC GGCAACAAGT CGAGCAAACG CTGATCGGTA   9960
GTGTCGGCCA GCTGAGCCGC CGCCGAGGGG TCGACGACCT CCAGCCGCGA CCGGCCCGTC  10020
ATTTTGCCGC TCTCCGGAAT GTCATCTGGC TCCAGCACAA TCTTGGCCAC ACCGGGATCC  10080
GAACTGGCCA ACTGCTCCGC GGTACCGATC ACCGCCCGCA GCGTCATGTC GTGGAAAGCC  10140
GCCCAGGCTT GCACGGCCAA AACCGGGTAG GTGGCACAGC GTGCAATTTC GTCAACCGGG  10200
ATTGCGTGAT CCGCGCTGGC CAAGTACACC TTATTCGGCA ATTCCATCCC GTCGGGTATG  10260
TAGGCCAGCC CATAGCTGTT GGCCACGACG ATGGAACCGT CGGTGGTCAC CGCGGTGATC  10320
CAGAAGAACC CGTAGTCGCC CGCGTTGTTG TCGGACGCGT TGAGCGCCGC CGCGATGCGT  10380
CGCGCCAACC GCAGCGCATC ACCGCGGCCA CGCTGGCGGG CGCTGGCAGC TGCAGTGGCG  10440
GCGTCGCGTG CCGCCCGAGC CGCCGACACC GGGATCATCG ACACCGGCGT ACCGTCATCT  10500
GCAGACTCGC TGCGATCGGG TTTGTCGATG TGATCGGTCG ACGGAGGGCG GGCAGGAGGT  10560
GCCGTCCGCG CCGAGGCCGC CCGCGTGCTC GGTGCCGCCG CCTTGTCCGA GGTAGCCACC  10620
TGCGTCCGCC CAGTGGCAGT ATGCGGACCC CGGAAAAAAA AAACTCGAGT GCGTTCTTCG  10680
GAGGTTTCCA ATTCTTGGAT TCCAGCACCC GCTCAGCGGT CTCGGCGACC AGACTGACAT  10740
TGGCCCCATG CGTCGCCGTG ACCAATGAAT TGATGGCGGT ATGGCGCTCA TCAGCATCCA  10800
GGCTAGAGTC ATTCTCCAGG ATATCGATCT CCCGTTGAGC GCCATCCACA TTATTGCCGA  10860
TATCGGATTT AGCTTGCTCA ATCAACCCGG CAATATGCCT GTGCCAGGTA ATCACCGTGG  10920
```

| | | | | | |
|---|---|---|---|---|---|
| CGAGATAATC | CTGCAGCGTC | ATCAATTGAT | TGATGTTTGC | ACCCAGGGCG | CCGTTGGCAG | 10980
| CATTGGCGGC | GCCGCCGGAC | CATAGGCCGC | CTTCGAAGAC | GTGGCCTTTC | TGCTGGCGGC | 11040
| AGGTGTCCAA | TACATCGGTG | ACCCTTTGCA | AAACCTGGCT | ATATTCCTGG | GCCCGGTCAT | 11100
| AGAAAGTGTC | TTCATCGGCT | TCCACCCAGC | CGCCCGGATC | CAGCATCTGT | CTGGCATAGC | 11160
| TGCCCGTCGG | CCTGGTAATA | CTCATCCCCT | ACTGCCCTCC | CCAAACCGCC | AGATCGCCTC | 11220
| GCGGATCACC | GTCCGGTTGG | CCTCCGGCAT | TTCACGCCGG | CTCGGCCGCT | GGATCCACCC | 11280
| CGCGCCGGTA | TTCGCAGTAA | CCCGTTGAAT | CCGCGCGCAT | GATGCACCGC | TTGGGCGATC | 11340
| AGCCGGGTGG | TCACCTCGCT | TGCGCTGGCC | GCGCTGTCGC | ACGGGCGCT | CGGTGGTAAC | 11400
| GGACGTCATA | ATTAACCAGC | GTAACCGAAC | CTAAGACCAG | CTAGCTGCGG | CAATATTGGC | 11460
| GACCAGGACT | ATGGCGCCCT | CCGAACCCGG | CCGATCCATG | TCAAAACATT | GACAATGCGT | 11520
| ACTCACGCCG | TGTCGGGCGC | GCTGAATGAC | CGCATTGCGG | CGCTCATTCG | GTGCGTAGTC | 11580
| GCTACCACCG | CAACAATGGG | CTTAGGCCAT | TCCTTCGTTC | ATCGCGCGGG | ACATGGCCGA | 11640
| TAACGCAGCG | GTCAGCTGCT | CGCCCGCCGC | GTCGTTATAC | GCGGACGCCG | CGGCCTGCGC | 11700
| ATTGTGCAGC | GCCTCGTTGA | CCCGCTGAGC | CGCCGCCTCG | GCACCCAGCT | TCTTCAGCAA | 11760
| ACCATCTTCG | ATGCGCAGGC | CGGTGAGCCA | CTGGTGCCCA | TTGATCGTCA | CTTCGACGGT | 11820
| CTCGGCTTCG | TCGGTGGCGC | GGAAGGATCC | GTTGTTCATC | TGATTGAGCG | TCCCGTCTAG | 11880
| GGCCGACTGA | AACCGCGCCG | CCAGCGTCAA | CGCCCGGGCG | ACATGCGGGT | CCAATTCGTC | 11940
| CATGCTCACT | TCGACTCCTT | ACTGTCCTGG | CGCCGACGGT | TACCAATGAC | GGCCTCGGTC | 12000
| CATGCCCGAT | CCTCGGTGTA | GAGCGCCTCG | TCTTCCTGCT | GAGAACCCTT | GGACTTGGCG | 12060
| CCCCCTTGTC | CCTGATGCGC | GGCACCCATC | GGCATTCCA | TGCCACCGCC | GCCCAGCGCG | 12120
| GCGCCGCCGC | CGGCCCTTCC | CTGGCCTAAG | CCGGCAATGT | CACCAGCGCC | AGCGGGCCGC | 12180
| ACCGATTCGG | CGCCCCCGAT | CGCGGATCCC | AACGGCGCCG | ACGGCACCCC | GCCGCCTCCA | 12240
| CCGCCACCGA | GCGATGCCGC | TTTGACCGCC | ACGTCGCCCG | ACAGCGCTGC | GGCTTCCCGC | 12300
| CCAGCCGACG | TCAGCTGCGC | CGCCGTGTCA | GCCGGGAGGC | CACCACCCGG | CGATCCGGTA | 12360
| GGCGGAACCA | TCGGTGCGGC | TGGCATCCCG | GTACCGGGAG | TCACACCGGA | GCCGTCAGAC | 12420
| GGCGGCATCA | GGAAGCCAGG | GATCAATCCC | TGCTCTTGCG | GAGGCGGGGC | GGGTCGATCT | 12480
| TGATGGCGGG | GGGGAGGCTT | CGGCGGGTTT | ACCGGTTCCA | GGGCTGCCTT | GTTGTTGTAT | 12540
| TCGGTCAGCA | CCTTCTCCGA | CCTCTGCTGA | TACTCCGCGT | ACACCGGGAG | AATTTGGTCG | 12600
| CGGGCCGAAG | GGTTTTCCGC | GTAAAGCCGT | TCGAGCCCGA | CTATGTCTTC | ATAAGTCGGA | 12660
| TGTTCCCGCC | TAGCCCACAC | GTGCAGCTGC | GCGACATATT | GAGCCTGCTT | GGCCATCGCA | 12720
| GCGCTCAATT | TGGCCATGTG | GAGTATCCAT | TGCCGGTGTT | GATCGAGCGA | AGCCTCGCAA | 12780
| GCGGTAGCCG | CATCGCCTTC | CCAGTTGTCA | AACCCCGGA | ACCGCTTGAC | GTCGCCTTGC | 12840
| AGCGTCAGGT | TGAAAGTGTT | CCACCCATCC | GCAAAGTGCG | CGAGCGATGC | GCCTTGGTCG | 12900
| CCCGTTTCGA | GCTTCCTTGC | CGCTTCTTTG | AGATCCATGA | AGTTGGGTTC | ACCGGCCGTG | 12960
| GCCACCCTCG | GCGTATCGGT | TAGTTCGGCC | GAACTGTCCC | CTCCGACGGC | CCCGGCCGAT | 13020
| TCTGCCTGCA | CAGTTCCTTC | GCCGTCGTTG | TCCAGCGCGG | TCGCAGCCTC | CTCATCAACC | 13080
| TCGCCATACG | CCTTGGCCGC | GTTGCGCAGC | GAGGTCGCCA | GACGCTGCCG | CTCTTTGGCA | 13140
| CCGGCCGCCA | GGTATTCCCG | CATGTTGTCG | GCGGACAATA | CCAGCTGTTG | GGCGGCGTTT | 13200
| TTAGCCGCCG | TGAGTTCGCA | CGGTGTGATG | GGGACATCAG | TCGGTGGGTC | CGCCATCGGG | 13260
| GCCTCCACCT | CGTTGGCCCT | GTTCAAAATC | TCTTGCTGAT | CCACCGTCAC | GGTCTGCGAC | 13320

-continued

```
TGCGTCATAT CGGATCATCC TCCTTAGTGC TATAGCCATT ATCGTCGCTA AACTGAAAGG    13380
TTCCTGCACT AATTTGATGC CGCCCGTTCA TGCCGGCATC GCGAACGGAT CGCCCTACTT    13440
CGGCAGCGCC ATCTGGTAGC GGCTTTCCTC GGGTGGGGAA ACCCGGCGAA TCGGCAGCTG    13500
CCGATGCCGC GGGGTACCGA TCACATTGTG CCGCAGAATC ACCCGGTCAA TACCGGGATG    13560
CGGGCCGAGA TAGGTCGTCG CATTCGGCCA CGCCACCTTT ACCTCCTGCC CGATGTGTGC    13620
GCCGATCAAC CGGGCAAATT CCTCGAACTG TGGCCCGACT GTGACCATCG CACCTGCCGC    13680
CGCCGCACGC ACCACGAACT GGGTGAATGT CTGAGCGTCA CCCAGGTTGA GGGCGATGTC    13740
GACATCGTCG AAGGGCATGT AGACCGGGCA TCGGTTCACC GTCTCGCCGA CCAGTACCCC    13800
AGCTGACCCG ATCGGCAGCT GGCAGTGGCG GTTGGCCACC AGATGCTGGC CTTGCAGCGC    13860
GGGCCGCTGC CCGCCAAATA GGCGGGCGAA GCCCTGGGT GTCTTGGGCT TGTCCGCCGT     13920
GGTCAGCAAC ACCGTGGACT GCGGGGCCAT CCCCGGCGCG ACCCGGACTC TGGTGATGGT    13980
GTGGTCCGCG CGCGCCGACC ACCATACATC CGGACCTCCG GGCGCCGCGT AGGCGGCAGT    14040
GTAGGCATCG CGCCCCTTGA TCATCGACCA TTTCTCCCGC ACAAAGCCGA TGTCGGTGGC    14100
GTGGTCGTAG TCATCGAAGC TGCGGCCACA CACCGCGTCG ACACCATGGC TAGCCAGTCG    14160
ATCGGCAATG CGCGTCGCGG ACGCCACCAA ATACCGGGCC AGTCCTGCGA CGCCTTCATC    14220
GCGGCGCTGC GCCGATTTGC GGGTGCGTTC CGGGTCGGCG CGCAGCACGA TCCAGGTCCG    14280
GCGGTTCGCC GGCGCCGGGT CTGTCCCGAT CACCTGCTGA TACAGACTCA CCACGTCCGG    14340
CGCTGCGGTA TTGCCGACGC GGTAGCCGGC TGAGACGATA TCGGCCTCCA AGTCGGGACA    14400
GTGCACCGAC AGGAGCTCCT CCACCAGTCC GGTGTCCAGC ATGTCGTCGG TGTGGGCTTG    14460
CCCGTCGACG ATGACCGTCG GCGTGAATGG TCGGGAATG AGCTCGATTA CGGCGACCAG     14520
AAACTCGCCT TGCCAGCGCA CCGCAACGTG ATCTCCTGGC TTCACGGTGG CCCCGACCAC    14580
AGGTTCTGAC GAGGAATCCG GGGGCCGTCG GCGCCGCCGC AACCACGCGT ACACCGCCGC    14640
CACCCAGCCG GTGATCCGGC GGCCGTAGAA AGTGACCGTG GCCACGATGA CGCCCAACGA    14700
GGCCAGCGCA ATCCCCGCCC ACCAGTAGCG CGTCTCCAAG AATGCGATGA TGCATGGCGG    14760
GGCCAACGCG GAGGCAAGCA AGGCGTGCCC GGTGCTGAAC CGCAGCCCTA AAGGATTTCT    14820
CATCGGCGGC TCAGCGCCCG TCTAGCCAGC GCGCCCAGGC CCAGGGCCAA CGTAAGGCCG    14880
ACGGCCACCA ACGCCACAGC CGTAATCGGG CGACGATCGG GACCCGGCTC CACCACCGGG    14940
GGTGGAAGTC GTCTGACGTT GTATGGCGCC GAAGCAGGGC CGGGCGGAAT GTCCCACGTC    15000
AGCGCGGCCA CCGCATCGAT GACGCCGGCG CCGACCAGGT CGTCGACCCC GCCCCCGGGG    15060
TGTCTCGCGG TGGCGGTGAT CCGGTGGATG ATCTGCGCCG GCGTCAGGTC GGGGAACCGC    15120
TGCCGAAGCA GGGCCGCCAG ACCCGACACA TATGCCGCGG CAAACGAGGT GCCGGCGATG    15180
GGTACCGGCC CCTCCCGGCC TTGCAACGCA TTCACCGGTT CACCGGTGTC GCCGAGCGCG    15240
ACGATGTTTT CTGCGGGCGC GGCCACGTCC ACCCACGGTC CGTGCATCGA GAACGAGCTG    15300
GGCATCCCGG TCTGGCCGAT ACCGCCGACG CTTAACACCA GCGGTGCGTA CCACGCCGGG    15360
GTGACAACGG TCTGCACATT GTTCCAGCCG CGTGGGTCGC CGGGTGTGGA CGGGTCCGGC    15420
GCCGGATTCT GTACGCAATC GCCACCGGTG TTGCCGGCCG CGACCACCAC CACCACGCCT    15480
TTGACGTTGA CCGCATAGTC GATGGATGCA CCCAGTGAGG TTTCATCGAT CGGCCTGCTC    15540
ACCTTGTAGC AGGCGGCTTC ACTGATGTTG ATCACACCCA CGCCGAGGTT GGCGGCGTGC    15600
ACCACGGCGC GGGCAAGACT GCGGATGGAA CCGGCGGCCG GGGTGGCGTT GGGGTCATTC    15660
GGGTTGGCTT GTGAGCCGAC CGGTTCGAAG GCCTCAGACG TCTGACGTAG CGAGAGCAGT    15720
```

-continued

| | | | | | |
|---|---|---|---|---|---|
| CGAGCGTCGG | GCGCGACGCC | GACGAACCCG | TCGGTGGGCG | CGGGCCGGCC | CGCGATGATG | 15780 |
| GATGCTGTGA | GAGTCCCATG | GGCATCACAG | TCAGACAGGC | CGTTACCGGC | CTGGTCGACG | 15840 |
| AAATCGCCGC | CAGGTTCCGC | CGGGACCCGT | GGCGAAGCGT | CGACACCGGT | GTCGATCACC | 15900 |
| GCCACCGTCA | CCCCGGCCCC | GGTCGCGAAC | TTGTGGGCAT | CGGCCACGCC | CAGATACGTG | 15960 |
| TTGCTCCACG | GCGGATCGTG | GAACCCGGAC | CCCGGCAGCG | TGGTGGGCGA | CGCGCACAAA | 16020 |
| ACGCGCTGTT | CGGTAGGCTG | ATCCGGGCCC | GCCACGTCGG | GCGGCAACGC | GCCCGGATCG | 16080 |
| ATCGGCGGTG | GCGTGATGGC | CGATGCGGGC | GACGCGGTGA | GCAACGCCAG | CGCCACCGTG | 16140 |
| ATCAGAAAGA | TACGGTGCAC | TCCCAGAACA | CTCCATTCGT | TGAGATTCAT | TGCGATTCAT | 16200 |
| TGAGCTGCGT | TGCTACCTTG | GGCCACTTGA | CGGACCTGTG | TGCATTTTAG | ACGTAACGGC | 16260 |
| TGGGCAAACA | ACGCTGTCAC | GCCTGGGCTG | GTCCGCCGCG | CCGACCAGGG | CGCGTAGGCG | 16320 |
| CTGTACCTGG | ACCACGCCGG | GACTCAACGG | TTTTGCTACC | GCACTAGCCG | ATATGCGGCT | 16380 |
| GCTACCAAAC | GATCGCGGCC | ATGTCTCGGT | TGTCTGAGCA | CACGCTGCGT | ATCGCGGCAT | 16440 |
| CGATGTCGGT | GGCGGTGATG | ATCTGCAGAT | CCTGAACCGA | TACCGGTTGG | CCCGCACGTT | 16500 |
| TTTGCGCAAC | CACCCGGGTG | TCCCGGAACC | CTTCGGCGCG | TTCGATCACG | TTGCGGGCGA | 16560 |
| ACCGACCGTT | TTGCATAGCG | TCGATACCGT | GCTGCCCACT | AGGGGTGGTG | TAGTTACGGA | 16620 |
| TGGTGGTGAC | CGCGTCGAGG | AATACCTCCC | GTGCGGCGTC | ATCGAGCTGG | CTGGCGCGCG | 16680 |
| GTGTAGCGTA | GCGGTGTCCA | ATCTCGACGA | TCTCCACCGG | CGAATAAGAC | TCGAACCGCA | 16740 |
| GCTTTCGGTT | GAACCGGCCA | GCCAAACCCG | GGTTCACGGT | GAGGAATTCG | GTACCCCGGG | 16800 |
| TTCGAAATCG | ATAACTTGGA | TCCGGAGAGC | TCCCAACGCG | TTGGATGCAT | AGCTTGAGTA | 16860 |
| TTCTATAGTG | TCACCTAAAT | ACTTG | | | | 16885 |

( 2 ) INFORMATION FOR SEQ ID NO:17:

( i ) SEQUENCE CHARACTERISTICS:
        ( A ) LENGTH: 15239 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

| | | | | | |
|---|---|---|---|---|---|
| GGATCCTCGG | ACTGGCCGCG | GTCGTGCTTG | TGCACGAGTT | CACCGAGGTC | ATCGTCATCG | 60 |
| CCAACGGCGT | GCGGGCCGGA | CGCATCAAAC | CACTTGCCGG | GCCACCCAAG | ACACCTGATC | 120 |
| GGACTATCCC | GGGGTAGCGA | CGCGCGGAAT | CGTGGAGTGT | GTTGGACCA | GCAATAGCGT | 180 |
| CACTGTGACG | AAACAGCCGC | CGTCTTCTGG | AAGTTATACC | CGGTTATACT | ATCTGTATGA | 240 |
| AGACAGCTAT | TTCTCTGCCG | GATGAGACGT | TCGATCGGGT | ATCGCGGCGT | GCGAGTGAGC | 300 |
| TCGGCATGAG | TCGGTCCGAG | TTCTTCACGA | AGGCTGCGCA | GCGCTACCTG | CACGAGCTGG | 360 |
| ACGCCCAATT | GCTCACGGGC | CAGATCGACA | GGGCTCTAGA | GAGCATCCAT | GGCACCGACG | 420 |
| AAGCGGAGGC | CCTCGCCGTG | GCCAACGCAT | ACCGCGTGCT | AGAAACCATG | GACGATGAGT | 480 |
| GGTGATTAGT | CGTGCCGAGA | TCTACTGGGC | TGACCTCGGG | CCGCCATCAG | GCAGTCAGCC | 540 |
| GGCGAAGCGC | CGCCCGGTGC | TCGTAATCCA | GTCAGATCCG | TACAACGCAA | GTCGCCTTGC | 600 |
| CACTGTGATC | GCAGCGGTGA | TCACGTCCAA | TACGGCGCTG | GCGGCAATGC | CCGGCAACGT | 660 |
| GTTCTTGCCC | GCGACCACAA | CGCGACTGCC | ACGTGACTCG | GTCGTCAACG | TCACGGCGAT | 720 |
| TGTCACGCTC | AACAAGACTG | ACCTCACCGA | CCGAGTTGGG | GAGGTGCCAG | CGAGCTTGAT | 780 |
| GCACGAGGTT | GACCGAGGAC | TTCGTCGCGT | ACTGGACCTT | TGACACTGCG | CCACGCGACA | 840 |

```
ATTCGTCACG GTGACGTTCC TGCTTGGTGT AAGCCCCCCC GCCGGGGGAA CTACTCGCCG    900
GAGGTGGTGT TGTGGGCAGG CTTGAGGGCA AGGTTGCATT CATTACGGGC GTGGCTCGGG    960
GTCAAGGCCG TTCGCATGCG GTCCGCCTAG CCGACGGCCA AGCGCGTGCG CTCGGCAAGG   1020
TCGATGTTGA GGCGTGCGGT GCGCTCGTTG GTGAGGTAGA AGTGTGGGGC CGTGACGTGC   1080
GTGACGATCG ACGGGTGTTT GTCGAGAGTC CTGCCGACGA GTTCGGCGCG TGCCGCCGCG   1140
TCGCGCGTCA GGGCATCCGT GTCGTAGGGC TGCCCGTTTC ACAGAGGGAA CTTGTCGAGC   1200
CCGAAGCCGG GTGCGCGGCG AGGCGCTCGG CTGCTGGCTC CCAGTAGACA TCTAGGCCTG   1260
CGTCGACTGC GGCTGCGGCA GCGTCGTGCT GGTGACGAGT GGCGTTGGTG TCCAGCGTGA   1320
TCGCAGTGGT GCCGGCGTGG TCGCGGGACA GGAAGTCCTC GACCGGTTTG TGATCACCCG   1380
GCCCGAGCCG AAACTGAATG CCCATCGTCG TGAAGTTCCT CTCGCATCGA CGCCTCGGTT   1440
CGTGTCATAA TACATGACAA ATCAATAGAC AAAAGGAAGA CAGGCTGCCC ATGGGAGTAA   1500
ATGTGCTCGC CTCGACCGTG TCGGGTGCGA TCGAGCGCTT GGGATTGACC TACGAGGAAG   1560
TCGGTGACAT CGTCGATGCC TCGCCGCGTT CCGTGGCGCG ATGGACCGCA GGTCAGGTGG   1620
TTCCCCAACG CCTCAACAAG CAACGACTTA TCGAGCTGGC CTATGTCGCC GACGCCCTCG   1680
CGGAAGTGCT GCCGCGTGAC CAGGCGAACG TGTGGATGTT TTCGCCGAAT CGGTTACTGG   1740
AACACCGCAA GCCTGCCGAC CTCGTGCGAG ACGGCGAGTA CCAACGCGTG TTGGCGCTCA   1800
TCGACGCGAT GGCGGAGGGA GTGTTCGTGT GAGCGATGCC CTCGATGAAG GGCTCGTCCA   1860
GCGTATCGAC GCACGCGGAA CAATTGAGTG GTCGGAAACG TGCTACCGGT ATACCGGCGC   1920
GCACCGTGAC GCCTTGTCCG GTGAGGGCGC GCGCAGATTC GGAGGCAGGT GGAATCCGCC   1980
GCTGCTCTTT CCGGCGATCT ATCTTGCTGA TTCCGCCCAA GCCTGCATGG TTGAGGTGGA   2040
ACGGGCGGCG CAAGCGGCTT CAACGACCGC AGAGAAGATG CTCGAGGCGG CCTACCGACT   2100
ACACACGATC GACGTCACGG ACCTGGCCGT CCTCGATCTG ACAACCCCGC AAGCTCGGGA   2160
AGCCGTGGGG CTCGAGAACG ACGACATCTA TGGCGACGAC TGGTCAGGGT GCCAGGCGGT   2220
CGGACATGCG GCCTGGTTCT TGCACATGCA AGGTGTCCTC GTGCCGGCGG CGGGCGGTGT   2280
CGGCCTCGTT GTCACCGCGT ATGAACAGCG AACTCGGCCG GGCCAACTAC AACTGCGACA   2340
AAGCGTCGAT CTGACGCCTG CTCTTTACCA AGAACTTCGA GCCACGTAGC TGGCCAGCTT   2400
GGCGCAGAGA AGGATGCCGC TGTGCCATGG TCATCGTAAG GAGCAACTCG CATCACTTAT   2460
AAGCCGATAA GCGACATTAT GTCAAGTGAA GCTGGTCGTA TTGGGTTAGC TGCGCCGTTT   2520
GTGCTAGCGG GCACGCTCCT TGTGCGTGCT GCGGCAGCGA GCGTGTCGTC AAAGGTTGCG   2580
AGGCTTGCCT GGTGATGAAT TGCCACATCC GGCACGCAGC AATCAGGTAG TTTTAGCCCG   2640
CTGCTAGCGC GTAGTTCGGC GAGACGCAGC AGCTCGCCAT CGTCGTACGG CGCAACGACG   2700
CTACCCGCGG AACGCGGATC GTCGAGCATC GATGATCAGG CGCCGCAATA ATTTGGAACG   2760
GGGCTCGCCA GGCCATCGCT GGGCGGCCCG GTCCAATGCC TGAGCTACCT CCGGGGTTTC   2820
GGTTATTTGG TAGCGCGGAC GAGTGGTCGA CATAGAACGA AGTGTGCCAC TTCTAGCAAA   2880
GGTGGTACAC CTACTGGCGG CCGCGGGTTT ACCGCCCCTG CCAGTCACCG CACTTCCGGC   2940
GGCGGACGAC GAGCACCGCG GAATCCACAT GCGGCGGTGG CAGGAACGCG CGCCGTGGCA   3000
GCATGAGGCC GACGGTCAGG GTGAACCTTC GCGCGTTGCG AGAAGCGAAT TTACATACGA   3060
GGGCTCGCTG CAGCACGAGA TCGGCCGCGA CAAGCCCGCT GTTGGGTGCC AGCAGCGTCC   3120
GCAGCAGGCG GGACGAAATC CCGTACGGCG GGTTCGCCAC AACCCGGAAC GGCCGGCCGG   3180
GCAACCGGAT CGAGGCGGCG TCCGCGTGCA CCACGGTAAT GCCAGGGAAT CGCTCGCGGA   3240
```

-continued

```
GGACACCGAC TCGTCGCGGG TGCAACTCCA CGGCGACCAC CCGCGCCCCC GCTCGCACTA    3300
GATGCGCCGT CAGTGCCCCT TCGCCGGCGC CGATGTCAAA CACGAGCTCA CCGGACCGCA    3360
CTGCGGCCGC GCTGACTACC CGCGCTGCCC ATTCGTCATG GAGCCGGTGC CAGCCCCATG    3420
CCCGTCGCGA CCGTCCGAGG GCGGACACGA CGTACCGTCA CTGCGTAGAT GCCCACGCGC    3480
CCGACCGTAG CCCGCCACCG GCACTGCGAT CAATCCAATT TCTCGGTTCA GGCAACCTTC    3540
TGGTCATCAC CAGCCCCAGG GCTCTGGCGC CGTCCGCATC AACTCCGAGA TGACGTTGGC    3600
CGTGACGACC CACTAGACCC ACCTGGCAGT AGCCGCATTG TCGCAGTCGG CGAGCCTCAG    3660
TGCGCAGTCG CGTCTAGGTG CAAGGATATT GCCCGTTGAG CAGACAACTC GACGGCGGCG    3720
AGTAAGAACC GGTCAGCCCG CCTCTTAGGC CGCCCGTGGC TGAACCACCG GGGGCAATGA    3780
TGCGATTCCA ATTCGCTGGG CTGAGAACGT AGTGCGTGCC AGATCGTGCA ACGGTGCTAT    3840
TCCATGTGTG CAAGACGGAT TCTCCTGCCG GCAAGTCGAA TTCAAGCTTC CAATCGGTTA    3900
GCGGCGCCGT GCTCGAGTTT GTGATGGTGA AGCGGGCGAT GAAACCGGTC TGCCACGTCG    3960
ATGTCACCGA CAACGTCGCC CTGGCCGTCG CCGCACTAGC GACCGGGGTG ATGGCGAGTC    4020
CGAGGATGGC AACTATCAAT GCCGACACGG TTGCGTGAAG CGCTGTCCGC CAGCGCCTCA    4080
CGTAAATGTT CAGTCCGGCC ATGACAGCCA ACACTAATGC CAATGAGGCG ATATCGGCCG    4140
TCTCCTCGCG AGCAAGCTAC AGCAACTTTG CTCAACCGCA ACCGTGATGA AATTTGGCCT    4200
CGACCCACCC TGAACCAGAT ATCGGCCCGG CCGAACGCGA ACTTGCGGAC GGGGAAGGCC    4260
AGACAGCCTC GACCCCACTC CCCCGATTAG CGCCGTTCAC CGTTCGCGAC CGGTATCAAC    4320
GGGCTACAGC TCCAACACGA TCCGTAGGGC CGCGTCACGC CGAATGTGCA CTGGTGGCGC    4380
CGACACGCCC GGGCGAGGCC GCCGTCGGCG TGTCAGCTGG TGACTGAGTT GTGCAGACTG    4440
ACCGCGCGCC CTCCTGCCGA ACGGTATGTG CCCATCGACG ATCACGTGGT CCAACCCGCG    4500
TGTGCACACG TGCTGTACTA GGTCACGGTC AGCGAGATTC CCAGCGCAAC CATCATGACC    4560
GCGATCAGGC CGTCGAGGAT TCTCCACGAG CCGGGGTTGG TGAACAGCCC GCGCAACCGG    4620
CCGGCTCCGA ACCCGAGGGT GGCGAACCAT ACCGCACTGG CTGTGACCGC GCCGAGGCCG    4680
AACAGCCAGC GCTGGTCGCT GTGCTCGTTG GCCAGCGCGC CTAGCAACAC GACGGTGTCG    4740
AGGTAGACGT GTGGGTTGAG GAACGTGAAT GCCGCACAGG TCACCAGGAC CTCGGCTAAG    4800
CGAACCGGCG TGGCGCCAGA TGGGATCAGC GCAACAGGTC GCCACGCCCG CCGGGCCGCA    4860
AGTAGCCCGT AGCCGATTAG GAAGGCGGCG CCGCCAAACT TGACGACATT GAGCGCACGC    4920
GGATGTGCGC CGATCAATGC GCCGAACCCC GCGATACCGG CGGCGATCAG CACGATGTCG    4980
GACACCGTGC ACAGCGCCAC CACCGGCAGC ACGTGCTCAC GCTGGATTCC CTGCCGCAGC    5040
ACGAATGCGT TCTGCGCGCC AATCGCGGCG ATCAGCGTGA AGCAGGCCAG GAAGCCGACG    5100
ACCAGTGGTG AGTTCACGCA ATCGACACTA GGCAGTTTGT ATGGGTCAGT ATAGCTAATA    5160
ATTCTTCATT TACATTAGCA TTATTAATGT GCAGTGCGAC GCTCCGCAGA TGGTCTACAC    5220
CTGAGATGGT GGATCCGCAG CTTGACGGTC CACAGCTGGC CGCATTGGCT GCCGTGGTCG    5280
AACTGGGCAG CTTCGATGCG GCCGCGGAGC GCCTACATGT CACCCCTCG GCTGTCAGTC    5340
AGCGCATCAA GTCGTTGGAG CAGCAGGTCG GCCAGGTGCT GGTGGTCAGG GAAAAGCCAT    5400
GTCGGGCGAC GACCGCAGGT ATCCCGCTGT TGCGGTTGGC CGCGCAAACA GCGTTGCTCG    5460
AGTCCGAGGC GCTCGCTGAA ATGGGTGGCA ACGCGTCGCT GAAACGCACG CGGATCACCA    5520
TTGCGGTAAA CGCCGATTCC ATGGCGACAT GGTTTTCGGC CGTGTTCGAC GGTCTCGGCG    5580
ACGTCCTGCT CGACGTTCGG ATCGAGGACC AGGACCATTC CGCGCGGCTG CTACGGGAGG    5640
```

-continued

```
GTGTGGCGAT GGGCGCGGTG ACCACCGAGC GGAACCCGGT GCCGGGCTGC CGGGTGCACC      5700
CGCTGGGTGA AATGCGCTAC CTACCAGTGG CCAGCAGGCC ATTCGTCCAG CGCCATCTAT      5760
CCGACGGGTT CACTGCCGCC GCGGCGGCTA AAGCTCCGTC ACTGGCGTGG AATCGTGACG      5820
ATGGGCTGCA GGACATGTTG GTGCGTAAGG CCTTTCGTCG CGCCATCACC AGACCGACGC      5880
ACTTTGTCCC GACCACAGAG GGCTTCACCG CCGCAGCGCG CGCCGGGCTG GATGGGGCA       5940
TGTTCCCCGA GAAGCTGGCA GCATCTCCGC TTGCCGATGG ATCGTTCGTA CGGGTCTGCG      6000
ACATACACCT CGACGTCCCT CTCTATTGGC AATGCTGGAA ACTGGACAGT CCGATCATCG      6060
CGCGAATTAC CGACACGGTG AGGGCGGCGG CAAGCGGTCT GTACCGGGGC CAGCAACGCC      6120
GCCGCCGACC GGGTTGACCG ACGCCAGCAT GTTGTTGTGT CAGCGCGGCT TGGTCTCGAT      6180
GTCCCGGCCT TGCTGGACCC GCTTCCTCAA ACAGGTTGAA CTTAACGACT CAGACGGAAA      6240
CGCTTGAACC GCGACGTCGC TCCGGACACC AATTTGACTC GGCTCTTTGG CAATTGAAGG      6300
TGAGCTGCGA GCAGCCGGGT GACCGCATCG TTGGCCTTGC CATCAATCGC CGGCTCGCGG      6360
ACGTAGATAA TCAGCTCACC GTTGGGACCG ACCTCGACCA GGGGTCCTTT GTGACTGCCG      6420
GGCTTGACGC GGACGACCAC AGAGTCGGTC ATCGCCTAAG GCTACCGTTC TGACCTGGGG      6480
CTGCGTGGGC GCCGACGACG TGAGGCACGT CATGTCTCAG CGGCCCACCG CCACCTCGGT      6540
CGCCGGCAGT ATGTCAGCAT GTGCAGATGA CTCCACGCAG CCTTGTTCGC ATCGTTGGTG      6600
TCGTGGTTGC GACGACCTTG GCGCTGGTGA GCGCACCCGC CGGCGGTCGT GCCGCGCATG      6660
CGGATCCGTG TTCGGACATC GCGGTCGTTT TCGCTCGCGG CACGCATCAG GCTTCTGGTC      6720
TTGGCGACGT CGGTGAGGCG TTCGTCGACT CGCTTACCTC GCAAGTTGGC GGGCGGTCGA      6780
TTGGGGTCTA CGCGGTGAAC TACCCAGCAA GCGACGACTA CCGCGCGAGC GCGTCAAACG      6840
GTTCCGATGA TGCGAGCGCC CACATCCAGC GCACCGTCGC CAGCTGCCCG AACACCAGGA      6900
TTGTGCTTGG TGGCTATTCG CAGGGTGCGA CGGTCATCGA TTTGTCCACC TCGGCGATGC      6960
CGCCCGCGGT GGCAGATCAT GTCGCCGCTG TCGCCCTTTT CGGCGAGCCA TCCAGTGGTT      7020
TCTCCAGCAT GTTGTGGGGC GGCGGGTCGT TGCCGACAAT CGGTCCGCTG TATAGCTCTA      7080
AGACCATAAA CTTGTGTGCT CCCGACGATC CAATATGCAC CGGAGGCGGC AATATTATGG      7140
CGCATGTTTC GTATGTTCAG TCGGGGATGA CAAGCCAGGC GGCGACATTC GCGGCGAACA      7200
GGCTCGATCA CGCCGGATGA TCAAAGACTG TTGTCCCTAT ACCGCTGGGG CTGTAGTCGA      7260
TGTACACCGG CTGGAATCTG AAGGGCAAGA ACCCGGTATT CATCAGGCCG GATGAAATGA      7320
CGGTCGGGCG GTAATCGTTT GTGTTGAACG CGTAGAGCCG ATCACCGCCG GGCTGGTGT      7380
AGACCTCAAT GTTTGTGTTC GCCGGCAGGG TTCCGGATCC GATGACATAT GACGGGATGG      7440
TTCCCGTTAC CCCACCGGAA TCGATGATCG AGGGACGGG TATGGGAGTC CCACCATCGA       7500
TCTTTACGTA CAGGGTGGTG ATCGGCGATC CGACGACCTC GACGTTGGGC GCAGGTAGCG      7560
GGTTGGGACC GAACACGAGC TCACCTGCGG GTGCGTCGAT GAGCACTCCC TGGTTGAGGT      7620
CACCCGGTAA CGCCATCGTC GGAATGCTGG GGCCTGGTCC CACCGCATTG GACCCAACTC      7680
CCAGAACGCC GTCCACGCCG ACGGCACCGA AATAGGCTTC GAACGGGTT GTTGTCGGAT       7740
CGGCCAGCAA GGCGCTGAAG TAGGTCGAAA TGGCGAAGGG GGACGTTGGG ATGGACAAGA     7800
GGACGACATT AACGGTGGTC GGCGCGGTGA CGATGCCATT CCCGAAGTCC ACCGTCGTGG      7860
TATACGTGGC GAAGATGTAG TACAGCCCCC CGCTGTAACC GCTGATGCTC AATCCGGTTG      7920
GGAGGCCCAT GTGAAGCACT CCCAGGATTC CCCGACATC CTCAGGTGAG ACAACAAGAT       7980
CAGCGGATCC GGTGTCGACC AGAATGGTTG ACGTCGGTCC GCCGTTGACG TTGGCATGTA      8040
```

-continued

```
CCGTCGGCTC TGTGACATGA ATTATCTCCA GCGGGACGGT TCTGCCGTCG CCGCCTGGCC   8100
CACTGACGCC GTATCCGCCA TACAACAGGC CGCCGCGGCC TCCGGCGCCG CCCGTGCCAC   8160
GATCGACACC GACTCCATCA CCGAGGCCGC CGGCTCCGCC GTTCGCTCCC CAGCCCAAAA   8220
GTCCTGTGGC ACCGCCGGTT CCGCCGGCTC CACCACTCAT GCCGGGATG CTCGACGCGC    8280
CCCCGGGCCC GCCGATCCCG CCGTTGCCGA GCAGCCAGCC ACCGTTTGCC GCCGGCTCCC   8340
CCGGGGGCGT TGGGGCCGCC GGCTCCCCCG GCGCCGCCAT TGCCGATCAA CGCCGCGGAA   8400
CCGCCGGCAC CGCCGCCGAC CCCCGACGCC GTCGCGGAAT AACCGTTGCC GCCGTTGCCG   8460
TACAGCAGCC CACCCGCCCC GCCATTCGGA CTCGTTGCCG TCCCGGGTGC TCCGTCGCCG   8520
ATTAGCGGAC GCCCCAACAA CGTTTCGGTT GGTGCATTGA CCGCGCCCAG CAGATCGTGC   8580
TGCGCGGTCT GCAACTGTGA CGCGATGGTG GCCTCCGCGG CCGCATACGA TCCTGACGCC   8640
GAGTTCAGCG TCTGCACGAA CTGTTGATGG AAAGCGCTCG CCTGCGCGCT GACCGCTTGA   8700
TATTCCTGAC CGAACCTGGC AAACAGCGCT GCCACCGCCG CCGATACCTC ATCAGCGCCA   8760
GCGGCCGCAA GCGCGGTGGT CGAGGCGGCA GCCGCGGCAT TCGCCGCGCG CAGTGTGGAA   8820
CCTATGTTCT CCACATCCGC TGCCGCGGAC GTCAAGAACT CGGGAACCAC GACCAGAAAT   8880
GACACGCCGC CCCTCCGCCT CGATCACCAT CCCTGCGCGC ATACAGCGTA TCCAGACGCT   8940
GCCTTTGACA TCTCGGATTT TCAGTAGCTA CCGCACGGCA CAGCACGCGT TAGGTAGATA   9000
GTGGCTATTT GCTGGTACCA TCTACCTGTG GCGCTGAATA TCAAAGACCC TGAGGTAGAC   9060
CGACTAGCCG CCGAACTCGC TGACCGGCTG CACACCAGCA AGACTGCCGC CATCCGGCAT   9120
GCCCTGTCTG CCCAGCTGGC GTTTTTGGAG TCGCGCGCCG GCGACCGTGA GGCACAACTT   9180
CTCGACATCT TGCGTACCGA AATCTGGCCC CTGCTTGCCG ACCGCTCCCC CATCACCAAG   9240
CTCGAGCGCG AACAAATCCT CGGCTACGAC CCCGCAACCG GAGTCTGAGC ACCGCAATGA   9300
TCGTGGACAC AAGCGCCGTG GTGGCCCTGG TTCAAGGCGA GCGGCCGCAC GCCACCCTGG   9360
TCGCGGCCGC CCTGGCCGGC GCCCATAGCC CCGTCATGTC TGCACCCACC GTCGCCGAAT   9420
GCCTGATTGT CTTGACCGCC CGTCACGGCC CCGTTGCGCG CACGATCTTC GAACGACTTC   9480
GCAGCGAAAT CGGCTTGAGC GTGTCATCTT TCACCGCCGA GCATGCCGCT GCCACGCAAC   9540
GAGCCTTTCT GCGATACGGC AAGGGGCGCC ACCGCGCGGC TCTCAACTTC GGAGACTGTA   9600
TGACGTACGC GACCGCCCAG CTGGCCACC AACCACTGCT GGCCGTCGGC AACGACTTCC    9660
CGCAAACCGA CCTTGAGTTC CGCGGCGTCG TCGGCTACTG GCCAGGCGTC GCGTAACCGT   9720
ATGCGCGGTG ATCGCTGTTT GTAATGAGTT CAGCGACACG AAGAATAAAA TATGGGTAGC   9780
CGAAATCACT AAGCTACAGT GCTGGTGCAC GCCATGAAAG ACCGTCAATG ACAAGGAGGA   9840
CGGCCGAAAT GCCCAAGGAC CGACTGCCGG ACTTGACGCC CACAGGAGCG TACGCACCGG   9900
CCAACAGCGG CATGACCATG GCAAGGCAGG ACGGCCCTCG ATGACCGGCA AGCGCGTTGA   9960
GCGGGTGCAC GCAATCAATT GGAACCGGTT GCTCGATGCT AAAGATTTGC AGGTCTGGA    10020
ACGTTTGACC GGTAACTTTT GGTTGCCGGA AAAGATTCCG CTCTCCAACG ACCTGGCATC   10080
TTGGCAAACG TTGAGTTCCA CCGAGCAGCA GACGACGATC CGGGTGTTCA CCGGCTTGAC   10140
CCTGCTCGAC ACCGCGCAGG CGACGGTGGG AGCAGTGGCC ATGATCGACG ACGCGGTCAC   10200
CCCCCACGAA GAGGCGGTCC TGACCAACAT GGCGTTCATG GAGTCAGTGC ACGCCAAGAG   10260
CTACAGCTCG ATCTTCTCGA CCCTGTGCTC GACCAAGCAG ATCGACGATG CCTTCGACTG   10320
GTCGGAACAG AACCCTTACC TGCAGCGAAA AGCGCAGATC ATCGTCGACT ACTACCGCGG   10380
TGACGACGCG CTCAAGCGCA AAGCATCGTC GGTAATGCTG GAGTCCTTCC TGTTCTACTC   10440
```

```
CGGCTTCTAC CTGCCCATGT ACTGGTCGTC GCGGGGTAAG CTCACCAACA CCGCCGATCT    10500
GATCCGGCTG ATCATCCGAG ATGAAGCCGT CCACGGCTAC TACATCGGCT ACAAATGTCA    10560
ACGAGGTTTG GCCGACCTGA CCGACGCCGA GCGGGCCGAC CACCGCGAAT ACACCTGCGA    10620
GCTGCTGCAC ACGCTCTACG CGAACGAGAT CGACTATGCG CACGACTTGT ACGACGAGTT    10680
GGGCTGGACC GACGACGTTT TGCCCTACAT GCGTTACAAC GCCAACAAGG CGCTAGCCAA    10740
CCTGGGATAC CAGCCTGCAT TCGATCGTGA CACCTGCCAG GTGAACCCGG CCGTGCGCGC    10800
AGCTCTCGAC CCCGGTGCAG GGAGAACCA CGACTTTTTC TCCGGCTCCG GAAGCTCATA     10860
CGTAATGGGC ACCCACCAAC CACCACCGA CACCGACTGG GACTTCTAAC CGCCCAGCGC     10920
GTCGGGGGCG TCGAGCACCA CGCGACACCG GCCCGATCG ATCTGCTAGC TTGAGTCTGG     10980
TCAGGCATCG TCGTCAGCAG CGCGATGCCC TATGTTTGTC GTCGACTCAG ATATCGCGGC    11040
AATCCAATCT CCCGCCTGCG GCCGGCGGTG CTGCAAACTA CTCCCGGAGG AATTTCGACG    11100
TGCGCATCAA GATCTTCATG CTGGTCACGG CTGTCGTTTT GCTCTGTTGT TCGGGTGTGG    11160
CCACGGCCGC GCCCAAGACC TACTGCGAGG AGTTGAAAGG CACCGATACC GGCCAGGCGT    11220
GCCAGATTCA AATGTCCGAC CCGGCCTACA ACATCAACAT CAGCCTGCCC AGTTACTACC    11280
CCGACCAGAA GTCGCTGGAA AATTACATCG CCCAGACGCG CGACAAGTTC CTCAGCGCGG    11340
CCACATCGTC CACTCCACGC GAAGCCCCT ACGAATTGAA TATCACCTCG GCCACATACC     11400
AGTCCGCGAT ACCGCCGCGT GGTACGCAGG CCGTGGTGCT CAAGGTCTAC CAGAACGCCG    11460
GCGGCACGCA CCCAACGACC ACGTACAAGG CCTTCGATTG GGACCAGGCC TATCGCAAGC    11520
CAATCACCTA TGACACGCTG TGGCAGGCTG ACACCGATCC GCTGCCAGTC GTCTTCCCCA    11580
TTGTGCAAGG TGAACTGAGC AAGCAGACCG GACAACAGGT ATCGATAGCG CCGAATGCCG    11640
GCTTGGACCC GGTGAATTAT CAGAACTTCG CAGTCACGAA CGACGGGGTG ATTTTCTTCT    11700
TCAACCCGGG GGAGTTGCTG CCCGAAGCAG CCGGCCCAAC CCAGGTATTG GTCCACGTT     11760
CCGCGATCGA CTCGATGCTG GCCTAGACTC GCGAGGACCG CGCGGTGGTC ACTGCGCGGA    11820
TTTGGGGCGG CGGAAGTGAG TGTTCGGTGC GCCCACTGCG GTGACTCACC TGCAGCGCCG    11880
GCATCGACAG GCCGGGAGCT CAAGAATCGT CGCTAGAGAA TCTATGGTGC GTTAGAGGAT    11940
TCCCTGCTAG ACAGCCTTGG TGCGGTGGTC GGCCCGCGGA CGAGAGGATA TGCGATCCAC    12000
AAGCTGGGTT TCTGCAGCGT CGTCATGCTC GGGATCAACT CGATAATCGG CGCCGGTATC    12060
TTCCTAACTC CAGGTGAGGT GATCGGGCTC GCAGGACCCT TCGCGCCGAT GGCCTATGTT    12120
TTAGCTGGCA TTTTCGCGGG TGTCGTGGCG ATCGTCTTCG CGACGGCGGC AAGGTACGTC    12180
AGAACAAACG GTGCCTCCTA CGCCTACACA ACGGCCGCAT TGGGCGCCG GATCGGCATC     12240
TATGTCGGTG TCACCCACGC CATTACCGCG TCCATCGCTT GGGGGGTGTT GGCTTCTTTT    12300
TTCGTCTCGA CGCTGTTGCG AGTGGCCTTC CCCGACAAGG CCTGGGCCGA CGCCGAGCAA    12360
CTGTTCAGTG TGAAGACGCT GACGTTTCTC GGCTTTATCG GCGTGCTGTT GGCCATCAAC    12420
CTCTTCGGCA ACCGGGCGAT CAAGTGGGCC AACGGAACGT CAACGGTAGG CAAGGCATTC    12480
GCGCTCTCGG CATTCATTGT CGGCGGGCTG TGGATCATCA CCACCCAGCA CGTGAACAAC    12540
TACGCAACGG CGTGGTCGGC ATACAGCGCG ACCCCGTACT CGTTGCTTGG CGTCGCCGAA    12600
ATTGGCAAGG GCACGTTCTC GAGTATGGCG CTGGCCACGA TTGTCGCGTT GTACGCATTC    12660
ACCGGTTTCG AATCGATCGC GAACGCCGCC GAAGAAATGG ACGCGCCGGA CCGGAACCTG    12720
CCGAGAGCTA TACCGATCGC GATCTTCTCG GTTGGCGCGA TCTACTTGCT CACCCTAACG    12780
GTAGCGATGC TGCTCGGATC GAACAAGATC GCCGCGTCGG GCGACACCGT GAAACTGGCC    12840
```

-continued

```
GCGGCCATCG GAAACGCTAC CTTCCGAACG ATCATCGTCG TCGGAGCCCT GATATCGATG    12900
TTCGGCATCA ATGTCGCGGC CTCGTTCGGT GCACCGCGGC TTTGGACCGC GTTAGCGGAC    12960
AGCGGGGTTC TGCCGACACG CTTGTCACGC AAGAACCAAT ACGACGTGCC GATGGTCTCC    13020
TTCGCAATTA CGGCGTCGTT GGCGCTCGCA TTCCCGTTGG CGCTGCGGTT CGACAACCTG    13080
CACCTGACCG GCCTGGCGGT GATCGCCCGA TTCGTCCAGT TCATCATCGT GCCGATCGCT    13140
CTCATCGCAT TGGCGAGGTC TCAGGCAGTA GAACATGCTG CTGTGCGGCG AAATGCGTTC    13200
ACCGACAAGG TGTTACCGCT TGTTGCGATC GTGGTCTCGG TTGGGCTGGC AGTGTCCTAC    13260
GACTACCGCT GCATCTTTCT AGTGCGGGGT GGTCCGAACT ACTTCTCGAT TGCTTTGATC    13320
GTGATCACGT TCATCGTGGT ACCGGCGATG GCTTATCTGC ACTACTACCG AATCATTCGC    13380
CGGGTTGGCG ATCGGCCGAG CACTCGCTAG ATTCCGTTGG CGCTGAGCTC GAACGGGAGA    13440
ACACAACGGC GAGCGATGGC GGGAATAGCC TGGTCGGTGC GGGCAAGATT TCAACCTGCA    13500
TTCCCGGATC GGCGGCGCGG GCAAGCGTCT GCAACGCCGA GGGACTGTAG GCACGTAGTG    13560
CGCTGATAAA GCCGTCGTGC ATGCTCGAGC GCATCGACGA CCATGGCAGC AGCAGTAGGT    13620
GGAGCGGCAG TAGCAGCACC GAAGAGAGCG TGAACGACAG CGGTTTCTGC CGTTTGAGGT    13680
CGATGATCAG AAAGCGCTTC CCCACCCGGG TGGCCTCGGC GATCGCTTTG CAGGCGACCG    13740
TAGGCGGCAG GTGGTGAAAT GCCAGCGCGA AGACCGCCAG GTCATAGCTG TGGTCGTGGC    13800
CGTCGATTGC GGTGGCGTCG ATCACTTGGG TGCGTGCTCG CGGATGTGTT CCCAGCTCTC    13860
CCGCGGCGAT GTTGGCCACC GAGGTGGGAT CTAGATCGCT GATCGTCACC GTCGCTGTCG    13920
GGTGTAGCTC GAGGATTTTC GCTGAGAGCT TGCCATGGCC CGCACCAAGT TCCAGGATTC    13980
GCGGGTTGGG AATGTCAGAA ACAAGTTTCA GGGCTATCCG GGCGTACTTC TCGTGCAGGT    14040
TGGTCAGGGT GCCCACCCGG TCGAGCACCC CGATGATCTT CTGTTTGACC TCATCGGGCA    14100
CATCGTCGCG GTCGAGGTAC TCCAGTGCGT CGGTCTGGAA TCGACGATCC AGCCAAGACG    14160
CGTCGGGGCC ACCCCGTGGC ATCGTGGCGA TCGCCTGCTC GCGGATGTTC GCCTCACCCA    14220
TGGCAGCTCT TCCCCTCTCG ACGTCCGTG TTCGCAATGC TATGAGACCG CTGACCGGGC    14280
TCCCCAGCCC GCCGGTCGCG CGTGCTTAGC TACGTAGCAG AGGGGCCGTC ACTTCGAGGG    14340
CTGCCGCCAC TCGGTGATCT TGCGGCCCAA TGAATCGGCC GCGTTCGAGG CTGCCCGTCC    14400
CACGGCTTTG GTTCACGGTG AAGATCGCAC AGCCGGTGCC GGAAAAGTCC GCGGCACCGA    14460
TGTCGGTCAG CAAGACGTTG AAGAGAAACC CCGAGATCAC CGCCCATGGG ATCGTCATCA    14520
ACACCCCAGG CAGCGTCGAC ACCCGCGCCA CGAACCAGCA CTGAAGTAGG TATTCACGCC    14580
ACGCGAAAGG CGGCTTGAAC ATGCACACGG ACGTGTCGAG CGTCATCGCG AAGAAATCGC    14640
CCAGCGCGCC CACCGGCCGC AAGACCGGAT CAGCGACCCG ACCGGCCGCC TTGTCGGCCA    14700
CGATTACCAT GGCGCGGCGC ACCAGCTGGA TTCGATGCTG GGCCGTTGGG TGAGGTGGCG    14760
CACGCTGGCC CCCCGGACAG GTCGACGATC GGTGACATTG GTGAGCGTAC GCGGCAGAGA    14820
CCGCTGATGT CCATAGCCAA TACGCGATTG CTTGGACAAC TGATCGGTAA ATAGCAATGC    14880
AAACTGGCAT ATATTGGCTA TGATGTATCT TGCTAGTATC CTATAGCGCG GGCGATGTG    14940
CTCTGCTGCC TTGGCGGCCG ACAGGCGCAT CACCGGTCAA GCCGTTGGCT CGAGTCACGC    15000
TGGCGAGGCA CCACGATCAG GCATCAACAG CGCGCCCGAC GGGCGGTGAT CGGATGCCGC    15060
ATCCTGACCG CCTCGATTCG GGCCCGCCGA CCAGAGCCTT CGCGACCGGC GAGGTTGCCA    15120
CCATGGTCGT CGAAGCAACT TGCTGCTAAC GAGCCTGTAG TTTGCCAGC CCCCACTCGC    15180
GCTTTGTCTG CAGGTTTTCA GGCTCAGCGA CGGCTCATGT CGTTGCGCAC GGCGAATTC    15239
```

( 2 ) INFORMATION FOR SEQ ID NO:18:

( i ) SEQUENCE CHARACTERISTICS:
        ( A ) LENGTH: 12412 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

```
GAATTCACTT AGCTAACACC AGTTCTAGCA GCTGTCGGCG CGACTTCTTG TCAGTGCCCG      60
ACGTTATGAT TCGAACATGT TAGCGAATAG CCGGGAGGAG CTTGTCGAGG TCTTTGATGC     120
GCTGGATGCC GAGCTGGACC GCTTGGACGA GGTGTCTTTT GAGGTGTTGA CCACCCCGGA     180
ACGGCTGCGG TCTCTGGAAC GTCTGGAATG CTTGGTGCGC CGGCTACCGG CGGTCGGGCA     240
CACGTTGATC AACCAACTCG ACACCCAAGC CAGCGAGGAA GAACTGGGCG GCACGCTGTG     300
CTGCGCGCTG GCCAACCGGT TACGCATCAC CAAGCCCGAC GCCGCCCTAC GCATCGCCGA     360
CGCCGCCGAT CTCGGACCTC GTCCGAGCAC TCACCGGCGA ACCGCTAGCC CCACAGTTTG     420
ACCGCCACCG CCACCGCCCA ACGCCAGGGC CTGATCGGCG AAGGCGCACA TCAAAGTGAT     480
TCGCGCCCTT TTTCGGCCCA ACCTGCCCGC CGCGGTGGAT GTGTCCAAAC CCGCCAGGCC     540
GCCGAAGCCC GACCTGGCCG CAAACCGCTC AAATATCGTC CCGACGAGCT GGCCCGCTAC     600
GCCCAGCGGG TCATGGACTG GCTACACCCC GACGGCGACC TCACCGACAC CGAACGCGCC     660
CGCAAACGCG GCATCACCCT GAGCAACCAG CAATACGACG GCATGTCACG GCTAAGTGGC     720
TACCTGACCC CCCAAGCGCG GGCCACCTTT GAAGCCGTGC TAGCCAAACT GGCCGCCCCC     780
GGCGCGACCA ACCCCGACGA CCACACCCCG GTCATCGACA CCACCCCCGA TGCGGCCGCC     840
ATCGACCGCG ACACCCGCAG CCAAGCCCAA CGCAACCACG ACGGGCTGCT GGCCGGGCTG     900
CGCGCGCTGA TCGCCTCCGG GGAACTGGGC CAACACAACG GTCTTCCCGT CTCGATCGTG     960
GTCACCACCA CCCTGACCGA CCTGCAAACC GGCGCCGGCA AGGGCTTCAC CGGCGGCGGC    1020
ACCCTGCTAC CCATGGCCGA TGTGATCCGC ATGACCAGCC ACGCCCACCA CTACTCCCCC    1080
GCAAGCGGGA GGTACCCCCA GGCGATCTTC GACCACGGCA CACCCTGGC GCTGTATCAC    1140
ACCAAACGCC TAGCCTCCCC GGCCCAGCGG ATCATGCTGT CGCCAACGA CCGCGGCTGC    1200
ACCAAACCCG GCTGTGACGC ACCGGCCTAC CACAGCCAAG CCCACCACGT CACCGGCTGG    1260
ACCAGCACCG GACGCACCGA CATCACCGAC CTCACCCTGG CCTGCGACCC CGACAACCGA    1320
CTCGCCGAAA AAGGCTGGAC CACCCGCAAA AACACCCACG GCCACACCGA ATGGCTACCA    1380
CCACCCCACC TCGACCACGG CCAACCGTGG ACCTGTGAGA TACACTACAC CTGTGCGTGC    1440
TGCTGTCTAC CTCCGAATCT CAGAAGACCG CTCCGGCGAA CAGCTCGGCG TGGCCCGCCA    1500
ACGCGAGGAC TGCCTAAAGC TGTGCGGGCA GCGAAAATGG GTGCCCGTCG AGTACCTCGA    1560
CAACGACGTC AGCGCATCAA CCGGCAAGCG CCGCCCCGCC TACGAGCAGA TGTTGGCCGA    1620
CATCACCGCC GGCAAGATCG CCGCCGTGGT GGCCTGGGAC CTGGACCGGC TCCATCGCCG    1680
TCCCATCGAG CTGGAAGCCT TCATGTCATT AGCCGACGAG AAGCGGCTGG CCCTGGCCAC    1740
CGTCGCCGGC GACGTTGACC TGGCGACACC CCAGGGCCGG CTAGTCGCCC GCCTGAAGGG    1800
GTCGGTGGCC GCTCACGAAA CCGAGCACAA GAAGGCACGA CAGCGCCGCG CCGCCCGCCA    1860
GAAAGCTGAA CGCGGCCACC CCAACTGGTC GAAAGCCTTC GGCTACCTGC CCGGCCCCAA    1920
CGGTCCCGAA CCCGACCCCC GGACAGCGCC GCTGGTCAAA CAGGCCTACG CCGACATCCT    1980
```

-continued

| | | | | | |
|---|---|---|---|---|---|
| CGCCGGGGCG | TCCCTGGGCG | ACGTGTGCCG | CCAGTGGAAC | GACGCCGGGG | CGTTCACCAT | 2040 |
| CACCGGCCGC | CCGTGGACGA | CTACAACGCT | GTCGAAATTC | TTGCGCAAAC | CCCGCAACGC | 2100 |
| CGGACTACGC | GCATATAAGG | GTGCCCGCTA | CGGCCCGGTG | GACCGCGACG | CGATTGTCGG | 2160 |
| CAAGGCCCAG | TGGTCGCCGC | TGGTGGACGA | GGCGACGTTC | TGGGCCGCCC | AGGCCGTGCT | 2220 |
| GGACGCCCCC | GGCCGCGCCC | CCGGCCGCAA | AAGCGTGCGC | CGCCACCTGC | TGACCGGGCT | 2280 |
| GGCAGGCTGC | GGCAAATGCG | GCAACCACCT | GGCCGGCAGC | TACCGCACCG | ACGGCCAGGT | 2340 |
| CGTCTACGTG | TGCAAGGCGT | GCCACGGGGT | GGCCATCCTG | GCCGACAACA | TCGAACCGAT | 2400 |
| CCTGTATCAC | ATCGTGGCCG | AGCGGCTGGC | CATGCCCGAC | GCCGTTGACT | TGTTGCGCCG | 2460 |
| GGAGATTCAC | GACGCCGCCG | AAGCCGAAAC | CATCCGCCTG | GAACTGGAAA | CCCTCTACGG | 2520 |
| GAGCTGGACA | GGCTCGCCGT | CGAACGCGCC | GAAGGGCTAC | TGACCGCGCG | CCAGGTGAAG | 2580 |
| ATCAGCACCG | ACATCGTCAA | CGCCAAGATA | ACGAAACTTC | AGGCCCGCCA | ACAGGATCAG | 2640 |
| GAACGGCTCC | GAGTGTTCGA | CGGGATACCG | TTGGAACAC | CGCAAGTCGC | CGGGATGATA | 2700 |
| GCCGAGCTGT | CGCCGGACCG | GTTCGCGCC | GTCCTCGACG | TCCTCGCTGA | AGTCGTTGTC | 2760 |
| CAGCCGGTCG | GCAAGAGCGG | CAGGATATTC | AATCCCGAAC | GGGTGCAGGT | GAATTGGCGA | 2820 |
| TGAGCCGGCA | CCACAACATC | GTGATCGTCT | GTGACCACGG | CCGCAAAGGC | GATGGCCGCA | 2880 |
| TCGAACACGA | GCGCTGCGAT | CTTGTCGCGC | CGATCATTTG | GGTCGACGAG | ACCCAGGGCT | 2940 |
| GGTTACCGCA | GGCGCCAGCG | GTGGCAACAT | TACTCGACGA | CGACAACCAG | CCGCGAGCCG | 3000 |
| TTATTGGCTT | GCCGCCCAAC | GAGTCTCGCC | TACGACCTGA | AATGCGCCGC | GACGGGTGGG | 3060 |
| TGCGGCTGCA | CTGGGAATTC | GCCTGCCTGA | GGTACGGCGC | CGCCGGCGTG | CGCACGTGCG | 3120 |
| AGCAGCGGCC | CGTGCGGGTT | CGCAACGGCG | ACCTGCAAAC | ACTGTGCGAG | AACGTTCCGC | 3180 |
| GGCTACTGAC | CGGACTGGCC | GGCAACCCCG | ACTACGCACC | GGGTTTTGCG | GTGCAGTCGG | 3240 |
| ACGCGGTGGT | CGTCGCCATG | TGGCTGTGGC | GCACGCTCTG | CGAAAGCGAC | ACGCCGAACA | 3300 |
| AACTACGCGC | CACCCCAACG | CGTGGTAGCT | GCTAGACTCC | GACGTAGCCG | GCTTCGACTC | 3360 |
| CGGGGTTTTG | GTGTCCCCAA | GGAGTCGCAC | GTGTCGACCA | TCTACCATCA | TCGCGGCCGC | 3420 |
| GTAGCCGCAC | TGTCTCGTTC | CCGCGCATCC | GACGATCCCG | AGTTCATCGC | CGCGAAAACC | 3480 |
| GATCTCGTTG | CCGCGAACAT | CGCGGACTAC | CTCATCCGCA | CCCTCGCCGC | AGCGCCGCCC | 3540 |
| CTGACTGACG | AGCAGCGCAC | CCGGCTGGCC | GAGCTGCTGC | GCCCCGTGCG | GCGGTCAGGC | 3600 |
| GGTGCCCGAT | GACCGCCGGC | GCCGGCGGGT | CGCCGCCGAC | GCGACGATGC | TCGGCCACGG | 3660 |
| AGGACCGGGC | ACCCGCGACA | GTCGCCACAC | CGTCTAGCGC | CGATCCTACC | GCGTCACGCG | 3720 |
| CCGTGTCGTG | GTGGTCGGTG | CACGAGCATG | TCGCGCCGGT | CCTGGATGCT | GCCGGGTCGT | 3780 |
| GGCCGATGGC | CGGCACACCG | GCCTGGCGTC | AGCTCGACGA | CGCCGATCCT | CGCAAATGGG | 3840 |
| CCGCGATCTG | CGACGCAGCC | CGGCACTGGG | CTCTGAGGGT | AGAGACGTGC | CAGGAGGCGA | 3900 |
| TGGCGCAGGC | GTCACGTGAC | GTATCTGCGG | CCGCCGACTG | GCCCGGCATC | GCCGCGAGA | 3960 |
| TCGTCCGACG | GCGCGGCGTG | TACATCCCGC | GGGCGGGGGT | GGCGTGATGG | CCGACATCCC | 4020 |
| CTACGGCACC | GACTATCCCG | ACGCCCCTG | GATCGACCGG | GACGGGCACG | TGCTCATCGA | 4080 |
| CGACGGTGGC | AAACCGACGC | AAGTTCATCG | CGGCCAAGCC | CGAATCGCCT | ACCGGCTAGC | 4140 |
| CGAACGTTAC | CAGGACAAGC | TGCTGCACGT | GGCCGGGATC | GGCTGGCACT | CCTGGGACGG | 4200 |
| CAGACGCTGG | GCAGCCGACG | ACCGCGGCGA | AGCCAAACGT | GCAGTGCTGG | CAGAGCTGCG | 4260 |
| CCAAGCGCTC | TCAGACAGCC | TCAACGACAA | GGAATTACGC | GCCGACGTCC | GAAAATGCGA | 4320 |
| ATCGGCGTCC | GGCGTGGCCG | GCGTGCTCGA | CCTGGCCGCC | GCACTGGTAC | CATTCGCCGC | 4380 |

-continued

```
GACGCTAGCC GACCTCGACA GCGACCCGCA CTTGCTCAAC GTCGCGAATG GGACGCTGGA    4440
CCTGCACACG CTCAAATTGC GGCCCCACGC GCCCGCTGAC CGCATCACAA AGATATGCCG    4500
CGGTGCCTAC CAGTCCGACA CCGAATCGCC TCTCTGGCAA GCGTTCTTGA CCCGCGTTCT    4560
GCCCGATGAA GGTGTGCGCG GGTTCGTGCA ACGCCTGGCC GGCGTCGGCC TACTAGGCAC    4620
CGTCCGCGAA CATGTCCTGG CGATTCTTAT CGGTGTAGGT GCCAACGGAA AATCTGTGTT    4680
CGACAAGGCG ATTCGCTATG CCCTTGGCGA TTATGCCTGC ACCGCTGAGC CTGACCTTTT    4740
CATGCACCGG GAAAACGCTC ACCCAACAGG CGAAATGGAC CTCCGCGGCG TGCGATGGGT    4800
AGCGGTATCC GAGAGCGAAA AAGATCGCCG GCTGGCCGAA TCAACGATAA AACGGCTGAC    4860
TGGCGGCGAC GCCATCCGCG CCCGAAAGAT GCGGCAAGAC TTCGTGGAAT TCGAGTGGTG    4920
CCGTTTGAAG TAGTGATTCC TGCCGACGAG CAGGACCGGG AACTGGACGC ACGGTTGCAG    4980
TTGGAGGCCG ACAGCATCCT GTCCTGGGCG GTGGCCGGAT GGAGCGACTA TCAGCGAATC    5040
GGACTATCCC AGCCGGACGC GGTGCTCGCG GCAACGTCGA ATTACCGCGA GGACTCCGAC    5100
ACGATAAAGA GGTTCATCGA CGACGAATGC GTCACCAGCT CGCCGGTGCT GAAAGCCACT    5160
ACTACGCATC TGTTCGAGGC GTGGCAAAGG TGGCGGGTGC AAGAAGGCGT ACCCGAAATC    5220
TCGCGCAAAG CGTTCGGCCA GTCGCTCGAC ACCCACGGAT ACCCGGTCAC TGACAAGGCC    5280
CGTGATGGTC GTTGGCGGGC CGGAATAGCG GTGAGAGGGG CCGATGATTT CGATGATTAG    5340
CACACCTAAC GTGACGCATG TGACGCATTT CCAGGTTCGC CTACGCGCGC GCACGTATGG    5400
CGGTTATACC GCGCAAACGT CACATGCGTC ACGGCCTGCC GTGCCGTTCT GCCCAGGATG    5460
CGGTACCTAC CTGGCCGTTC ACGGCCGCCA CCGGGCGGAC TGTACCGCCA AACCAGCAAA    5520
CACCGGCGGT GCCGCATGAC CGCTGTCGCG ATCACCCCGG CATCCGGCGG TCGGCACAGC    5580
GTCCGATTCG CCTACGACTC TGCGATCGTG TCGTTGATCA AGTCCTCGAT CCCCGCCTAT    5640
GCCCGCTCCT GGTCCGCGCA CACCCGCTGC TGGTTCATCG ACGCTGACTG GACCCCACTG    5700
CTGGCCGCCG AGCTGCGCTA CCACGGCCAC ACCGTCACCG GACCCGCCGA CCCGGCGCAA    5760
CAGCAGTGCA CCGACTGGGC CAAAGCGTTG TTCCGGGCGG TCGGACCCCA GCGGACACCC    5820
GCCGTGTACA GGGCTTTATC CAAAGTGCTG CACCCCGACG CCCCAACCGG ATGCCCGATA    5880
CTGCAACAGC AGCTCAATGC CGCCAGAACC GCACTTACCA ACCCTGCTTG AAAGGACACA    5940
AGCCATGGCT GAAACCCCCG ACCACGCCGA ACTGCGGCGA CGAATCGCCG ACATGGCTTT    6000
CAACGCCGAT GTCGGTATGG CGACCTGCAA ACGCTGTGGT GACGCCGTGC CGTACATCAT    6060
CCTGCCGAAC CTGCAGACCG GCGAACCCGT CATGGGTGTC GCCGACAACA AATGGAAGCG    6120
CGCGAACTGT CCCGTCGACG TCGGTAAGCC GTGCCCGTTC CTAATCGCCG AGGGTGTCGC    6180
CGACAGTACC GACGACACCA TAGAGGTCGA CCAGTGACCC CGATCAACCG GCCCCTGACC    6240
AACGACGAAC GACAACTGAT GCACGAGCTG GCAGTCCAGG TTGTCTGCTC GCAGACGGGT    6300
TGCTCACCCG ATGCGGCGGT CGAAGCACTC GAATCCTTCG CGAAAGACGG AACACTTATC    6360
CTCCGCGGCG ACACCGAGAA CGCCTACCTC GAAGCCGGAG GCAATGTTCT TGTCCATGCC    6420
GATCGTGACT GGCTTGCCTT CCACGCGTCG TATCCCGGCA CGACCCGCT GCGAGACGCC    6480
CGACCTATCG AGCAGGACGA CGACCAGGGG GCGGGTCGC CATCGTGACC AGGCCCAGCC    6540
CGGACACCGC CACGGTGCCG GCGCGCATGC ACGCTCATTA CCTAGACTAA AAATTGATGG    6600
GAGGACCGAT GCCAAGACCA CCGAAACCGG CCCGGCTCAA ACTGGTTGAG GGCCGCTCCC    6660
CCGGCCGCGA TTCCGGCGGC CGGAAAGTCC CCGAGTCGCC GAAGTTTATC CGTCAGGCAC    6720
CGGATGCCCC GGACTGGCTC GACGCCGAGG CGCTGGCCGA ATGGCGGCGC GTCGCACCGA    6780
```

```
CTTTGGAGCG GCTTGACCTG CTCAAACCTG AGGATCGGGC GCTCCTGTCC GCGTACTGCG    6840
AGACCTGGTC CGTCTACGTC GCGGCGGTTC AGCGGGTCCG CGCCGAAGGC CTCACAATTA    6900
CCTCACCGAA ATCCGGTGTC GTGCACCGGA ACCCGGCGGT GACGGTGCG GAGACGGCGC     6960
GCATGCATCT GCTGCGCTTG GCCTCCGAGT TTGGCCTGAC CCCGGCCGCC GAGCAGCGAC    7020
TGGCGGTGGC GCCGGGCGAC GACGGCGACG GGCTCAACCC GTTTGCCCCG GACCGGTGAT    7080
GACCTTTTGT GTGTGATACA ATCGAGTTTG GCATCTCGGC ATCCGCTGAC GCCGGGCAGT    7140
CGCCGCGGGG CGGCTGGAAC CCGGATAGCG GCCGCCATGC GCCACAAGCG ATTCCGCGCG    7200
TTTCTTGCGT CTGCTAGGTG GTGGCCGAAT TTGAGTAGC ATCCTTTTCC GCATGGCCGA     7260
GCTGCGGTCT GGCGAAGGCC GAACCGTGCA CGGCACCATC GTGCCCTACA CGAGGCGAC     7320
CACCGTCCGC GACTTCGACG GCGAGTTCCA GGAAATGTTC GCTCCTGGCG CTTTTCGGCG    7380
CTCCATCGCC GAGCGCGGCC ACAAATTGAA GCTGCTGGTC TCTCACGACG CTCGAACCCG    7440
CTACCCGGTG GGCCGGGCCG TTGAGTTGCG GGAGGAGCCT CACGGCTTGT TCGGGCGTT     7500
CGAGATTGCG GACACCCCGG ACGGCGACGA GGCTTTGGCG AACGTAAAAG CTGGTGTCGT    7560
CGACTCGTTT TCGGTGGGTT TCCGACCGAT CCGGACCGT CGCGAAGGGG ATGTGCTGGT     7620
GCGCGTCGAA GCGGCGCTGT TAGAGGTTTC CCTAACCGGC GTTCCGGCCT ATTCGGGGGC    7680
ACAAATCGCC GGGGTGCGCG CGGAATCGCT TACAGTCGTT TCCCGTTCGA CAGCCGAAGC    7740
CTGGCTGTCC CTACTCGATT GGTGAACAAT CTATGACCGA ATTCGACGAC ATCAAAAACC    7800
TCTCTTTACC TGAAACCCGT GACGCGGCGA AGCAGCTCCT CGACAGTGTC GCCGTGTGAC    7860
CTGACCGGTG AGGCGGCGCA GCGTTATTCA GGCGCTGACG CGCCACGCCG AGGAACTGCG    7920
GGCGGAGCAG CGCCGCCGCG GCCGCGAAGC CGAGGAGGAG CTGCGCCGCT ACCGGGCCGG    7980
TGAGCTGAGG GTGGTGCCCG GCGCTCCCAC CGGCGGCGAC GACGGCGACG CGCCGCCGGG    8040
CAACTCGTTG CGGGACACCG CGTTTCGCAC ACTGGATTCT TGTGTGCGAG ACGGCCTGAT    8100
GTCGTCGCGG GCGGCGGAGA CCGCGGAAAC CTTGTGCCGC ACCGGGCCGC CGCAGTCCAC    8160
CTCGTGGGCG CAGCGCTGGC TGGCGGCCAC CGGCAGCCGC GACTATTTGG GCGCGTTCGT    8220
CAAGCGGGTT TCCAATCCTG TTGCGGGGCA CACGGTTTGG ACCGACCGGG AAGCGGCCGC    8280
GTGGCGTGAG GCTGCCGCGG TGGCCGCCGA GCAGCGAGCG ATGGGCCTGG TGGACACCCA    8340
AGGCGGGTTT CTGATCCCGG CGGCGCTGGA CCCGGCGATC CTGCTGTCGG GTGATGGGTC    8400
GACGAACCCG ATTCGGCAGG TGGCGAGGGT GGTGCAAACG ACCTCCGAGA TTTGGCGGGG    8460
CGTGACTTCC GAAGGCGCCG AAGCTCGTTG GTACTCCGAA GCCAGGAGG TGTCCGACGA     8520
TTCGCCAGCG TTGGCCCAGC CGGCGGTGCC GAACTACCGT GGAAGCTGCT GGATTCCGTT    8580
CTCCATCGAG CTGGAGGGTG ACGCGGCGAG CTTCGTTGGC GAGATCGGCA AGATTCTCGC    8640
GGACAGCGTT GAGCAACTGC AGACCGCGGC GTTCGTCAAC GGCTCCGGCA ACGGCGAGCC    8700
CACCGGGTTC GTCAGCGCGC TAACCGGCAC CTCCGATCAG GTGGTCGTCG GCGCGGGGTC    8760
AGAAGCGATT GTGGCGGCGG ATGTTTACGC GTTGCAGTCG GCGCTGCCGC CAAGGTTCCA    8820
GGCCAGCGCC GCGTTCGCGG CGAACTTGTC CACCATCAAC ACGTTGCGGC AGGCGGAAAC    8880
TTCGAATGGC GCGCTGAAAT TCCCATCGCT GCACGACAGT CCGCCGATGC TAGCCGGGAA    8940
GTCTGTCCTG GAAGTCTCCC ACATGGACAC CGTTGATTCG GCGGTGACAG CGACGAATCA    9000
TCCACTGGTG CTTGGCGACT GGAAGCAATT CCTCATCGTC GACAGAGTTG GGTCCATGGT    9060
GGAGTTGGTG CCTCACCTGT TCGGGCCGAA TCGCCGGCCG ACCGGGCAGC GCGGATTCTT    9120
CGCCCTGGTTC AGGGTCGGAT CAGATGTGCT GGTGCGCAAC GCGTTTCGAG TTCTGAAGGT    9180
```

-continued

```
GGAGACTACC GCGTAGGTAG GATAGGGCCA GGCGTGGGCG GCCTCTGCTT AGGGGTGCCG    9240
GGCCGGCCAC GCCCGCCAAC TCCCCTGCGG GTTGCGTTGT CGATTCGTNN NNNNNNNNNN    9300
NNNNNNNNNN NNNNNNNNNN NNNNNNNNNN NNNNNNNNNN NNNNNNNNNN NNNNNNNNNN    9360
NNNNNNNNNN NNNNNNNNNN NNNNNNNNNN NNNNNNNNNN NNNNNNNNNN NNNNNNNNNN    9420
NNNNNNNNNN NNNNNNNNNN NNNNNNNNNN NNNNNNNNNN NNNNNNNNNN NNNNNNNNNN    9480
NNNNNNNNCC AAGCCAGAAT ATCGAGCCTG GCGGCCATGG TCGCCGCCTT CCTGTTGCCG    9540
CTGCTTGGCT TTCGGCCGTT CCAGCTCGGC GATCCGGCGG CCAGCGGCGC CATTTGTTTC    9600
TCCGCGAACA GGCGGATTTC TTTGTCGTCG CTGCGGGTTG CGTTGTCGAT TCGTTTGAGC    9660
CGCTTGTAGG TGCCGGCGGA GATGCCGAGG GCTGCGCCTA CCTCCTTGTC AGTGTGGCGC    9720
TGAGACGGCT TTGGTTCCAT GGGACCAAAG CCGGCATTGG TGATCGATGC ACCGAGGCGA    9780
CCACCCTCGC GTTGGCGCTC CTTGGCTTTC GGGCGTTCCA GCTCGGCGAT CCGGCGACCA    9840
GCGGCGCCAT TTGTTTCTCC GCGAACCGGC GGATTTCTTT GTCGTCGCTG TGGGTTGCGT    9900
TGTCGATTCG TTTGAGCCGC CGGTAGGTGC CGGCGGAGAT GCCGAGGGCT GCGCCGATAG    9960
CAGTGTCTGT TTCGTCGAA TGACGCTCTG ATTCTGGTTT GTAGCCCATG GGCCCCAAAC    10020
CAGAATATCG AGCCTGGCGG CCATGATCCT GCCCCTCGCG CTGCCGCTGC TTGGCTTTCG    10080
GCCGCTCCAG CTCCGCGATC CGGCGGCCAG CGGCGCCATT TGTTTCTCCG AGATAGCTTC    10140
CGGCCCATGG GCCGGAAGCT ATCCATGCCC CGCCCGTGGG ACCGCCCAGC GTCCTGTTGC    10200
CGCGGTGTTC ACCGTCAGCG CTCGTCTTCC GCTGGGCTTC CGCCGCCAAG CCCGATCATC    10260
CGGCTCCACG GCGGGGTGTC GTCGCCGTCG GGCTCGTCGT CGCCGGCGAG TCCGAGTTGC    10320
CGGTTGATGG CGGCTTGTTC CGGCCCGGAG CGGCCGGCCA GGATCGCCGG GCCGCACTCG    10380
TCGCCGCCGG CGGCGTCGGC GTGCTCGACG CTGATCCGCA GGAACGCTTC GAGCTCGCCG    10440
GTGTGCTCGT GCCGATTCAA CGCGGCCTGC AGCCGAACGA GCGCTTCCCT CACCTCCAAG    10500
GGCGCGTCCG GGAACCACGC CCGGATCGTC TCGGCCACCT GGTCGCGGTC GCAGACGGCG    10560
CGGTCACCGG TTTCCAGGTC GGTTACCGTC ACCAAGTGGT TGAAACGTGC TGGTGTGGTG    10620
GTCATGGTTG ATCTCCTGGC GTGGAATGTT CTTCAGCAGT CCACGGCCAA CCCCGCACCA    10680
ACACCTTCCA CCACCACGAG AAGCTGCTAC GCCACAACGA CGAGGACAAC CACGACGATC    10740
CGTGAGAATC GCCGCCCGCG AAGATCTTTG GACATCCCCA CATCGACGTG CGTCCTCGCC    10800
ACCTGGCCAG CACCCGCCCG AACCCGCGAG CTGGCCATTA AGACGAAGTT GCGATCAAAC    10860
CCCTTCGCCA TCAAGCTTTT TGGGCCCGCC TCACCCCAGC AGGTACTCGG CACGCGTGTT    10920
GCCGTCCCAG CGGCGCAAGC CGGCGAACCG ACCGTCAATC CGCGACGGCC GTCCGCAAT    10980
GCGCAGCGCC CGCCCCAATT GGTGACCACC GACCCGTCGG GCCAGGGTGA CATGGGCGGT    11040
CCACTGACCG GGCAGGCTGT TGGCCATCGG CGCGGGCGCC AGGTGCGGGC GCAGAGCCG    11100
GTGCACCTCG GCATGCAGGG CCAAAAGCTC GCTGGTCGGC ACCACCAGCC GGGTGAACAC    11160
GACATTGGCC CGCCCGAACA GCACCGGCGC GCCGATCACG CAGTCCAGCG GCAGCCGACG    11220
GGCAACCGCA CCCAGCGGCT CATCGACCTC CGGGGCGATC CGTTCGGCCA CCGCCAGCGA    11280
CACGTGCGGA CGGCTGGCCG GCGCCTGGCT GGGTATGCCG GCGGCGGCCA ACCCCGCCCA    11340
GATGCGCCGG ATCGCCGCCT CGGTATCGCT GTCGAAGACC AGCTCGATCG AATGCACCAT    11400
CAGCCGACCA GCCCGGCAAC CCAGTTGCGG TCGAACGCCC CGCGCTCAT CGCCGCGAAG    11460
TCCCCGGCAT CCAGCGACGC GGCCCCGGCG GGCAGAGCGG CCCGCACCGT AGCAATGCGC    11520
GCCAGCGCGG ACCGATTCGA GGCTGCCACC AACCCGGGCG GGTCCGGCCA GCTGCCGATC    11580
```

-continued

| | | | | | | |
|---|---|---|---|---|---|---|
|ACCAGCCCTG|CACATGAAAC|CTGTTGTGCA|GCAAGCGCTT|CCAACGTCAA|CTTGGTGTGG|11640|
|TTGAGGGTGC|CCAGGTCCGC|GGTGACCACC|ACCAAAGCCG|CGGCGGCCAC|GTCGACGGCG|11700|
|ACATCGCGCA|GCGTGACGCC|CGGCTCGGCG|AGTTCGACCA|GCAGCCCGCC|CGCCCCTCG|11760|
|ACGAGGGTCA|ACCGCCCGGG|ACGGTCCAGG|TCTGCGATCA|GCCGCACGAT|CTGATCGCGG|11820|
|GCGGGCAACG|CCATCCCGGC|GTGTTCGGCG|GCGGCGGCCG|GGGCCATCGG|CTGCGGATAT|11880|
|CGCGCCAAGC|CGGCCAGCTG|GGTCACCCCG|GCCAACCGGC|CGACCTCGGC|GAGGTCGTCG|11940|
|TCACCGCGGG|CGGTGCCGGT|CTGAACGGGC|TTGCACACCG|CCACGTCGAT|GCCGGCCTGA|12000|
|CGTGCGGCCG|ACGCCAGCGC|CGCGCAGACG|ACCGTCTTGC|CGACCCCGT|GCCGGTCCCG|12060|
|GTGACGACCA|GGATCGTCAA|CGGCGCGCCA|CGGCGAGAAC|ATCCGTCAGC|ACCCGCCGGG|12120|
|CCAGCTCGAG|CTCGCCGGCG|TTCAGCGATG|CGCGCGCGGT|CAGCCGCAGC|CGCGACGTAC|12180|
|CCGCGGGCAC|CGTCGGCGGC|CGGAAGCAGC|CCACCTTGAC|CCCGGCGTCC|AGGCAGGCCG|12240|
|CCGCGGCGGC|CACTGCCGAC|TCCGGCTCGC|CCAGGATCAC|CGACACCATC|GCCGAGTCCG|12300|
|GCACCGCAGC|CACACCGCAC|ATCCGCGCAA|GTTCACCAGC|GTGGTTGAGC|ACCGCCTGCG|12360|
|ATCGCCACGG|CTCGGCCTGC|AAGACGCGCA|GCGCGGCCCG|TGCGGCACCT|TC|12412|